(12) United States Patent
Luk et al.

(10) Patent No.: US 9,207,242 B2
(45) Date of Patent: Dec. 8, 2015

(54) CADHERIN-17 AS DIAGNOSTIC MARKER AND THERAPEUTIC TARGET FOR LIVER CANCER

(75) Inventors: John Moon Ching Luk, Mid Levels (HK); Nikki Pui Yue Lee, Pokfulam (HK); Lingxiao Liu, Shanghai (CN); Ronnie Tung Ping Poon, Sai Wan Ho (HK); Sheung Tat Fan, Mid levels (HK)

(73) Assignee: The University of Hong Kong, Hong Kong (HK)

( * ) Notice: Subject to any disclaimer, the term of this patent is extended or adjusted under 35 U.S.C. 154(b) by 128 days.

(21) Appl. No.: 12/569,386

(22) Filed: Sep. 29, 2009

(65) Prior Publication Data

US 2010/0092978 A1    Apr. 15, 2010

Related U.S. Application Data

(60) Provisional application No. 61/104,038, filed on Oct. 9, 2008.

(51) Int. Cl.
*G01N 33/574* (2006.01)
*C07K 16/28* (2006.01)
*C07K 16/30* (2006.01)

(52) U.S. Cl.
CPC .......... *G01N 33/57438* (2013.01); *C07K 16/28* (2013.01); *C07K 16/30* (2013.01); *G01N 33/57488* (2013.01)

(58) Field of Classification Search
None
See application file for complete search history.

(56) References Cited

U.S. PATENT DOCUMENTS

| | | | |
|---|---|---|---|
| 4,844,893 A * | 7/1989 | Honsik et al. ............... 424/85.2 |
| 5,597,725 A | 1/1997 | Suzuki | |
| 6,410,724 B1 | 6/2002 | Dejean et al. | |
| 6,569,996 B1 | 5/2003 | Blaschuk et al. | |
| 6,638,911 B1 | 10/2003 | Blaschuk et al. | |
| 6,682,901 B2 | 1/2004 | Blaschuk et al. | |
| 6,723,320 B2 | 4/2004 | Hofler et al. | |
| 6,962,969 B2 | 11/2005 | Blaschuk et al. | |
| 6,974,667 B2 | 12/2005 | Horne et al. | |
| 7,279,294 B2 | 10/2007 | Morin et al. | |
| 7,332,281 B2 | 2/2008 | Morris et al. | |
| 7,335,512 B2 | 2/2008 | Callewaert et al. | |
| 7,348,142 B2 | 3/2008 | Wang | |
| 7,368,548 B2 | 5/2008 | Dahary et al. | |
| 7,371,376 B1 | 5/2008 | Fendly | |
| 7,371,379 B2 | 5/2008 | Baughman et al. | |
| 7,371,574 B2 | 5/2008 | Liao et al. | |
| 2005/0202485 A1 | 9/2005 | Ye | |
| 2005/0203025 A1* | 9/2005 | Blaschuk et al. ............... 514/13 |
| 2007/0172857 A1 | 7/2007 | Daito et al. | |

FOREIGN PATENT DOCUMENTS

| | | |
|---|---|---|
| JP | 2007-175021 | 7/2007 |
| WO | WO 92/17608 | 10/1992 |
| WO | WO 00/26672 | 5/2000 |
| WO | WO 00/73803 | 12/2000 |
| WO | WO 01/62206 | 8/2001 |
| WO | WO 02/064798 | 8/2002 |
| WO | WO 02/097395 | 12/2002 |
| WO | WO 2005/042725 | 5/2005 |
| WO | WO 2007/109347 | 9/2007 |
| WO | WO2007141280 | * 12/2007 |

OTHER PUBLICATIONS

Angres et al Dev. Dyn. 221:182-193, 2001.*
Sigma antibody WH0011015M1 data sheet (2005).*
Spring prototol: Methods in Molecular Biology. vol. 271. p. 149-159. Pub. Date: May 12, 2004.*
Wang YongGang, PhD Thesis, 2010.*
Baumgartner, et al., "R. Heterotypic trans-interaction of LI- and E-cadherin and their localization in plasmalemmal microdomains", *J Mol Biol*, 378:44-54 (2008).
Berndorff, et al., "Liver-intestine cadherin: molecular cloning and characterization of a novel Ca2+-dependent cell adhesion molecule expressed in liver and intestine", *J Cell Biol*, 125:1353-1369 (1994).
Block, et al., "The degree of readiness of selected biomarkers for the early detection of hepatocellular carcinoma: notes from a recent workshop", *Cancer Biomark*, 4(1):19-33 (2008).
Blum, "Treatment of hepatocellular carcinoma", *Best Pract Res Clin Gastroenterol*, 19(1):129-45 (2005).
Bristeau, et al., "Conserved as well as divergent regulatory elements account for expression of the human and rodent phenylalanine hydroxylase genes", *Gene*, 274:283-291 (2001).
CDH17 cadherin 17 [Mus musculus] NCBI Accession No. NM_019753, pp. 1-5, Updated Mar. 4, 2010; Accessed Mar. 15, 2010.
CDH17 cadherin 17 [Rattus norvegicus] NCBI Accession No. NM_053977, pp. 1-3, Updated Jan. 20, 2010; Accessed Mar. 15, 2010.
CDH17 cadherin 17, LI cadherin (liver-intestine) [*Homo sapiens*] NCBI Accession No. NM_004063, pp. 1-6, Updated Mar. 7, 2010, Accessed Mar. 15, 2010.
Chen, et al., "Lentivirusmediated RNA interference targeting enhancer of zeste homolog 2 inhibits hepatocellular carcinoma growth through down-regulation of stathmin", *Hepatology*, 46:200-208 (2007).

(Continued)

*Primary Examiner* — Lei Yao
(74) *Attorney, Agent, or Firm* — Pabst Patent Group LLP

(57) ABSTRACT

Compositions and methods for diagnosing, treating and/or preventing cancers characterized by CDH17 overexpression based on the detection of CDH17 or the use of CDH17 as a target for therapeutic intervention or prophylactic intervention are provided. Methods for diagnosing and/or monitoring liver cancers using the expressing of CDH17 involve detecting and/or quantitating the CDH17 protein or encoding nucleic acids (DNA or RNA) in a biological sample such as urine from the subject. Methods for treating liver cancers using CDH17 as a target and of sensitizing cells with aberrant expression of CDH17 have also been developed. The methods include suppression or knockdown of the expression of CDH17 by administering an effective amount of a CDH17 inhibitor.

8 Claims, 5 Drawing Sheets

(56) References Cited

OTHER PUBLICATIONS

Cormier, et al.,"Management of hepatocellular carcinoma", *J Gastrointest Surg*, 10(5):761-80 (2006).
Curley, et al., "Radiofrequency ablation of hepatocellular cancer in 110 patients with cirrhosis", *Ann Surg*, 232(3):381-91 (2000).
Daniele, et al., "Alpha-fetoprotein and ultrasonography screening for hepatocellular carcinoma", *Gastroenterology*, 127(5 Suppl 1): S108-12 (2004).
Dantzig, et al., "Association of intestinal peptide transport with a protein related to the cadherin superfamily", *Science*, 264:430-433 (1994).
Debruyne and Delanghe, "Diagnosing and monitoring hepatocellular carcinoma with alphafetoprotein: new aspects and applications", *Clin Chim Acta*, 395:19-26 (2008).
Ding, et al., "Liver-intestine cadherin predicts microvascular invasion and poor prognosis of hepatitis B virus-positive hepatocellular carcinoma", *Cancer*, 115(20):4753-65 (Oct. 15, 2009).
Edamoto, et al., "Alterations of RB1, p53 and Wnt pathways in hepatocellular carcinomas associated with hepatitis C, hepatitis B and alcoholic liver cirrhosis", *Int J Cancer*, 106:334-341 (2003).
El-Serag and Mason, "Rising Incidence of Hepatocellular Carcinoma in the United States", *N Engl J Med*, 340:745-750 (1999).
El-Serag and Mason, "Trends in survival of patients with hepatocellular carcinoma between 1977 and 1996 in the United States", *Hepatology*, 33(1): 62-5 (2001).
El-Serag, et al., "Diagnosis and treatment of hepatocellular carcinoma", *Gastroenterology*, 134:1752-1763 (2008).
Fan, "Live donor liver transplantation in adults", *Transplantation*, 82(6): 723-32 (2006).
Ge, et al., "A clinicopathological study on the expression of cadherin-17 and caudal-related homeobox transcription factor (CDX2) in human gastric carcinoma", *Clin Oncol (R Coll Radiol)*, 20:275-283 (2008).
Goessling, et al., "Genetic interaction of PGE2 and Wnt signaling regulates developmental specification of stem cells and regeneration", *Cell*, 136:1136-1147 (2009).
Grotzinger, et al., "Li-cadherin: a marker of gastric metaplasia and neoplasia", *Gut*, 49:73-81 (2001).
Ito, et al., "Clinicopathological significant and prognostic influence of cadherin-17 expression in gastric cancer", *Virchows Arch.*, Oct, 447(4):717-22 (2005), Epub Oct. 19, 2005.
Kaposi-Novak, et al., "Met-regulated expression signature defines a subset of human hepatocellular carcinomas with poor prognosis and aggressive phenotype", *J Clin Invest*, 116:1582-1595 (2006).
Ko, et al., "Overexpression of LI-cadherin in gastric cancer is associated with lymph node metastasis", *Biochem Biophys Res Commun*, 319:562-568 (2004).
Kwak, et al., "The prognostic significance of E-cadherin and liver intestine-cadherin expression in colorectal cancer", *Dis Colon Rectum.*, Nov, 50(11):1873-80 (2007).
Lee, et al., "Genomic and proteomic biomarkers for diagnosis and prognosis of hepatocellular carcinoma", *Biomarkers Med*, 1:273-284 (2007).
Lee., et al., "Comparative proteomic analysis of mouse livers from embryo to adult reveals an association with progression of hepatocellular carcinoma" m *Proteomics*, 8:2136-2149 (2008).
Liu, et al., "Targeting Caderin-17 Inactivates Wnt Signaling and Inhibits Tumor Growth in Liver Carcinoma", *Hepatology*, 50(5):1453-63 (2009).
Llovet, "Updated treatment approach to hepatocellular carcinoma", *J Gastroenterol*, 40(3):225-35 (2005).
Llovet, et al. "Resection and liver transplantation for hepatocellular carcinoma", *Semin Liver Dis*, 25(2):181-200 (2005).
Lucka, et al., "Carcinoembryonic antigen-related cell-cell adhesion molecule C-CAM is greatly increased in serum and urine of rats with liver diseases", *FEBS Lett*, 438:37-40 (Oct. 1998).
Luk and Wong, "Monoclonal antibodies as targeting and therapeutic agents: prospects for liver transplantation, hepatitis and hepatocellular carcinoma", *Clin Exp Pharmacol Physiol*, 33(5-6):482-8 (2006).
Marrero, "Hepatocellular Carcinoma", *Curr Opin Gastroenterol*, 19(3):243-249 (2003).
Palmer, et al., "Gene- and immunotherapy for hepatocellular carcinoma", *Expert Opin Biol Ther*, 5(4):507-23 (2005).
Parasole, et al., "Prognostic value of serum biological markers in patients with hepatocellular carcinoma", *Clin Cancer Res*, 7:3504-3509 (2001).
Park, et al., "Expression of liver-intestine cadherin and its correlation with lymph node metastasis in gastric cancer: can it predict N stage preoperatively?", *Ann Surg Oncol*, 14(1):94-9 (Jan. 2007).
Parkin, et al., "Global Cancer Statistics, 2002", *CA Cancer J Clin*, 55: 74-108 (2005).
Poon and Fan, "Hepatectomy for hepatocellular carcinoma: patient selection and postoperative outcome", *Liver Transpl*, 10:S39-45 (2004).
Ruether, et al., "Inducible formation of liver tumors in transgenic mice", *Oncogene*, 8:87-93 (1993).
Spangenberg, et al., "Serum markers of hepatocellular carcinoma", *Semin Liver Dis*, 26(4):385-90 (2006).
Sun, et al., "Oncoproteomics of hepatocellular carcinoma: from cancer markers' discovery to functional pathways", *Liver Int*, 27(8):1021-38 (2007).
Takamura, et al., "Expression of liver-intestine cadherin and its possible interaction with galectin-3 in ductal adenocarcinoma of the pancreas", *Cancer Sci*, 94:425-43o (2003).
Takamura, et al., "Reduced expression of liver-intestine cadherin is associated with progression and lymph node metastasis of human colorectal carcinoma", *Cancer Lett.*, 212(2):253-9 (Aug. 30, 2004).
Wang, et al., "Alternative mRNA splicing of liver intestine-cadherin in hepatocellular carcinoma", *Clin Cancer Res*, 11:483-489 (Jan. 2005).
Wang, et al., "Liver intestine-cadherin (CDH17) haplotype is associated with increased risk of hepatocellular carcinoma", *Clin Cancer Res.*, 12(17):5248-52 (Sep. 1, 2006).
Wendeler, et al., "Intestinal LI-cadherin acts as a Ca2+-dependent adhesion switch", *J Mol Biol*, 370:220-230 (2007).
Wendeler, et al., "Unique gene structure and paralogy define the 7D-cadherin family", *Cell Mol Life Sci*, 63:1564-1573 (2006).
Wong, et al., "Identification of liver-intestine cadherin in hepatocellular carcinoma—a potential disease marker", *Biochem Biophys Res Commun.* 311(3):618-24 (Nov. 21, 2003).
Yuen and Lai, "Serological markers of liver cancer", *Best Pract Res Clin Gastroenterol*, 19(1):91-9 (2005).
Zender, et al., "An oncogenomics-based in vivo RNAi screen identifies tumor suppressors in liver cancer", *Cell*, 135:852-864 (2008).
Zender, et al., "Generation and analysis of genetically defined liver carcinomas derived from bipotential liver progenitors", *Cold Spring Harb Symp Quant Biol*, 70:251-261 (2005).
Zender, et al., "Identification and validation of oncogenes in liver cancer using an integrative oncogenomic approach", *Cell*, 125:1253-1267 (2006).
Wang, et al., "Anti-cadherin-17 antibody modulates beta-catenin signaling and tumorigenicity of hepatocellular carcinoma" , PLOS One, 8(9):1-6 (2013).

* cited by examiner

SEQUENCE LISTING

<160> NUMBER OF SEQ ID NOS: 6

<210> SEQ ID NO 1
<211> LENGTH: 215
<212> TYPE: PRT
<213> ORGANISM: Homo sapiens

<400> SEQUENCE: 1

```
Pro Leu Lys Pro Met Thr Phe Ser Ile Tyr Glu Gly Gln Glu Pro Ser
1               5                   10                  15

Gln Ile Ile Phe Gln Phe Lys Ala Asn Pro Pro Ala Val Thr Phe Glu
            20                  25                  30

Leu Thr Gly Glu Thr Asp Asn Ile Phe Val Ile Glu Arg Glu Gly Leu
        35                  40                  45

Leu Tyr Tyr Asn Arg Ala Leu Asp Arg Glu Thr Arg Ser Thr His Asn
    50                  55                  60

Leu Gln Val Ala Ala Leu Asp Ala Asn Gly Ile Ile Val Glu Gly Pro
65                  70                  75                  80

Val Pro Ile Thr Ile Lys Val Lys Asp Ile Asn Asp Asn Arg Pro Thr
                85                  90                  95

Phe Leu Gln Ser Lys Tyr Glu Gly Ser Val Arg Gln Asn Ser Arg Pro
            100                 105                 110

Gly Lys Pro Phe Leu Tyr Val Asn Ala Thr Asp Leu Asp Asp Pro Ala
        115                 120                 125

Thr Pro Asn Gly Gln Leu Tyr Tyr Gln Ile Val Ile Gln Leu Pro Met
    130                 135                 140

Ile Asn Asn Val Met Tyr Phe Gln Ile Asn Asn Lys Thr Gly Ala Ile
145                 150                 155                 160

Ser Leu Thr Arg Glu Gly Ser Gln Glu Leu Asn Pro Ala Lys Asn Pro
                165                 170                 175

Ser Tyr Asn Leu Val Ile Ser Val Lys Asp Met Gly Gly Gln Ser Glu
            180                 185                 190

Asn Ser Phe Ser Asp Thr Thr Ser Val Asp Ile Ile Val Thr Glu Asn
        195                 200                 205

Ile Trp Lys Ala Pro Lys Pro
    210                 215
```

<210> SEQ ID NO 2
<211> LENGTH: 97
<212> TYPE: DNA
<213> ORGANISM: Artificial Sequence
<220> FEATURE:
<223> OTHER INFORMATION: Synthetic shRNA for targeting CDH17 Exon 3

<400> SEQUENCE: 2
tgctgttgac agtgagcgac caagaaccga gtcaaattat tagtgaagcc acagatgtaa    60
taatttgact cggttcttgg ctgcctactg cctcgga    97

<210> SEQ ID NO 3
<211> LENGTH: 61
<212> TYPE: DNA
<213> ORGANISM: Artificial Sequence
<220> FEATURE:
<223> OTHER INFORMATION: Synthetic forward portion of the shRNA duplex
      for targeting CDH17 Exon 5

<400> SEQUENCE: 3
gatcccgcca gtccctatca ccatagagaa gcttgtctat ggtgataggg actggttttt    60

```
<210> SEQ ID NO 4
<211> LENGTH: 61
<212> TYPE: DNA
<213> ORGANISM: Artificial Sequence
<220> FEATURE:
<223> OTHER INFORMATION: Synthetic reverse portion shRNA duplex for
      targeting CDH17 exon 5

<400> SEQUENCE: 4
ctagaaaaaa ccagtcccta tcaccataga caagcttctc tatggtgata gggactggcg      60
g                                                                     61

<210> SEQ ID NO 5
<211> LENGTH: 19
<212> TYPE: DNA
<213> ORGANISM: Homo sapiens

<400> SEQUENCE: 5
caagaaccga gtcaaatta                                                   19

<210> SEQ ID NO 6
<211> LENGTH: 20
<212> TYPE: DNA
<213> ORGANISM: Homo sapiens

<400> SEQUENCE: 6
cagtccctat caccatagaa                                                  20
```

CADHERIN-17 AS DIAGNOSTIC MARKER AND THERAPEUTIC TARGET FOR LIVER CANCER

CROSS REFERENCE TO RELATED APPLICATIONS

This application claims priority to U.S. Ser. No. 61/104,038 filed Oct. 9, 2008.

FIELD OF THE INVENTION

This invention relates to compositions and methods for detecting and inhibiting cancer by targeting the expression, translation, and biological activity of liver-intestine cadherin (LI-cadherin), CDH17.

BACKGROUND OF THE INVENTION

Hepatocellular carcinoma (HCC), commonly referred to as liver cancer, is the sixth most common cancer worldwide in terms of numbers of cases (626,000 or 5.7% of new cancer cases in 2002). Parkin D M et al., *CA Cancer J Clin* 2005; 55:74-108. In the United States, the reported incidence has increased to 4.7/100,000 persons. HCC is a malignant tumor associated with high mortality and, because of the very poor prognosis, the number of deaths (598,000 in 2002) is almost the same each year as the number of new cases reported (Parkin D M et al., *CA Cancer J Clin* 2005; 55:74-108). The high mortality rate makes HCC the third most common cause of death from cancer. This unfortunate high rate of death is largely attributed to late diagnosis of this tumor as patients are usually in an advanced stage when first diagnosed.

HCC is often refractory to all current chemotherapies. Four major categories of treatment modalities are commonly offered to HCC patients: (1) surgical operations including tumor resection and liver transplantation; (2) percutaneous approaches, such as radiofrequency ablation; (3) transarterial interventions, such as embolization and chemoembolization; (4) molecular and medicinal therapies with the use of tagged antibody and drug medication. Unfortunately, there is no definite cure for HCC patients. Surgical resection is presently an effective means for removing tumor nodules; however, it is not applicable to late-staged HCC patients with large and multiple lesions and patients with distant metastases. Other treatment approaches, such as transarterial interventions, suffer from low response rate. Systemic chemotherapy has not been shown to be effective for the treatment of nonresectable HCC. Due to high recurrence rate after curative treatment, 5-year survival rate remains sub-optimal, at about 15%, for HCC patients after initial diagnosis. Ultimately, liver transplantation remains the best therapeutic intervention that offers the longest disease-free survival. Thus there remains a need for additional means for diagnosing, prognosing, and treating HCC.

Current surveillance program for diagnosing liver cancers relies mainly on detection of serum alpha-fetoprotein (AFP) and ultrasound imaging. However, serological level of AFP is inaccurate in detecting liver tumors, suffering from low sensitivity, when the cut-off level of AFP is at 20 ng/ml (Debruyne E N and Delanghe J R, *Clin Chim Acta,* 395: 19-26 (2008)), and non-specific in differentiating liver tumors from other malignancies as well (Marrero J A, *Curr Opin Gastroenterol* 19(3):243-249, 2003). Other imaging technologies, such as magnetic resonance imaging, angiography, computed tomography, are frequently employed to spot liver nodules, but these are usually only performed after other symptoms or positive screening have occurred. Current analyses often vary and are highly operator dependent.

Therefore, the objectives of the present invention are to provide an improved method of diagnosing liver cancer at an early stage and to identify new targets for liver cancer therapy.

SUMMARY OF THE INVENTION

Compositions and methods for diagnosing and treating liver cancers characterized by CDH17 overexpression based on the detection of CDH17 or the use of CDH17 as a target for therapeutic intervention or prophylactic intervention are provided.

Methods for diagnosing and/or monitoring liver cancers using the expression of CDH17 involve detecting and/or quantitating the CDH17 protein or encoding nucleic acids (DNA or RNA) in a biological sample such as serum from the subject. The methods include the steps of (a) contacting (reacting) the biological sample with an antibody specific for CDH17 which is directly or indirectly labeled with a detectable substance; and (b) detecting the detectable substance. The presence of CDH17 molecule in liver tissues denotes the incidence of liver cancer. A panel of mouse monoclonal antibodies specific for detecting human CDH17 has been developed and is used to detect the presence of CDH17 protein. The methods can be used to detect either soluble or truncated forms of CDH17 by using antibodies specific for the unique regions spanning domains 1 and 2 (D1-D2) of the truncated and secreted CDH17. In a preferred embodiment, the antibody is specific for SEQ ID NO: 1. In one embodiment, the method steps comprise: (a) contacting the biological sample with a binding agent that binds CDH17 protein to form a complex; (b) detecting the complex; and (c) correlating the detected complex to the amount of CDH17 protein in the sample, wherein the presence of elevated CDH17 protein is indicative of cancer. In a specific embodiment, the detecting of (b) further comprises linking or incorporating a label onto the agent, or using ELISA-based immunoenzymatic detection. Optionally, the method steps further comprise detecting a biomarker of cancer in the same biological sample or a different biological sample obtained from the subject, before, during, or after the detecting of CDH17. Optionally, the method steps further comprise comparing the level of CDH17 in the biological sample with the level of CDH17 present in a normal control sample, wherein a higher level of CDH17 in the biological sample as compared to the level in the normal control sample is indicative of cancer such as liver cancer.

The methods enable the use CDH17 as a tumor biomarker for liver cancers. In a preferred embodiment, the presence of CDH17 molecule in serum of HCC patients is detected, thereby providing a non-invasive serological assay for liver cancer, for use in patient surveillance programs, of at-risk populations, such as hepatitis carriers and cirrhotic patients.

In some embodiments, the subject has not yet been diagnosed with cancer. For example, the method can be used for the prognostic evaluation of a subject having, or suspected of having, cancer, comprising: a) determining the level of CDH17 in a biological sample obtained from the subject, such as urine, blood, or ascites fluid; b) comparing the level determined in step (a) to a range of CDH17 known to be present in a biological sample obtained from a normal subject that does not have cancer; and c) determining the prognosis of the subject based on the comparison of step (b), wherein a high level of CDH17 in step (a) indicates an aggressive form of cancer and, therefore, a poor prognosis. In other embodiments, the subject is suffering from cancer, such as liver cancer, and the detecting is performed at several time points at intervals, to monitor the subject before, during, or after treatment for the cancer.

Methods for treating liver cancers using CDH17 as a target and of sensitizing cells with aberrant expression of CDH17 have also been developed. The methods include suppression or knockdown of the expression of CDH17 by administering an effective amount of a CDH17 inhibitor. The suppression or knockdown of CDH17 reduces in size liver tumors derived from tumor cells that exhibit an increased expression of CDH17 and renders liver tumor cells more sensitive to certain chemotherapeutic drugs, such as Taxol, Epirubicin, and Carboplatin, and p53-based gene therapy. In one embodiment, the composition is a single-stranded short interfering ribonucleic acid (siRNA) molecule comprising about 19 to about 23 base pairs that down-regulates expression of the CDH17 gene. In another embodiment, the composition is an siRNA molecule comprising a region, for example, the antisense region of the siRNA construct, complementary to a sequence comprising a CDH17 and/or CDH17 gene sequence or a portion thereof. In another embodiment, a medicament comprising a siRNA molecule in a pharmaceutically acceptable carrier or diluent is provided. The CDH17 antagonist can suppress the expression of the CDH17 gene, inhibit the progression of HCC and sensitize the tumor cells to common chemotherapeutic treatment. In a preferred embodiment, CDH17 expression is inhibited using polynucleotide inhibitors which target SEQ ID NO: 5 or SEQ ID NO: 6. In another embodiment, the CDH17 antagonist is a monoclonal antibody specific for CDH17, which suppresses the expression and/or the activity of the overexpressed protein in the HCC cells.

DETAILED DESCRIPTION OF THE INVENTION

I. Definitions

Figure 1:
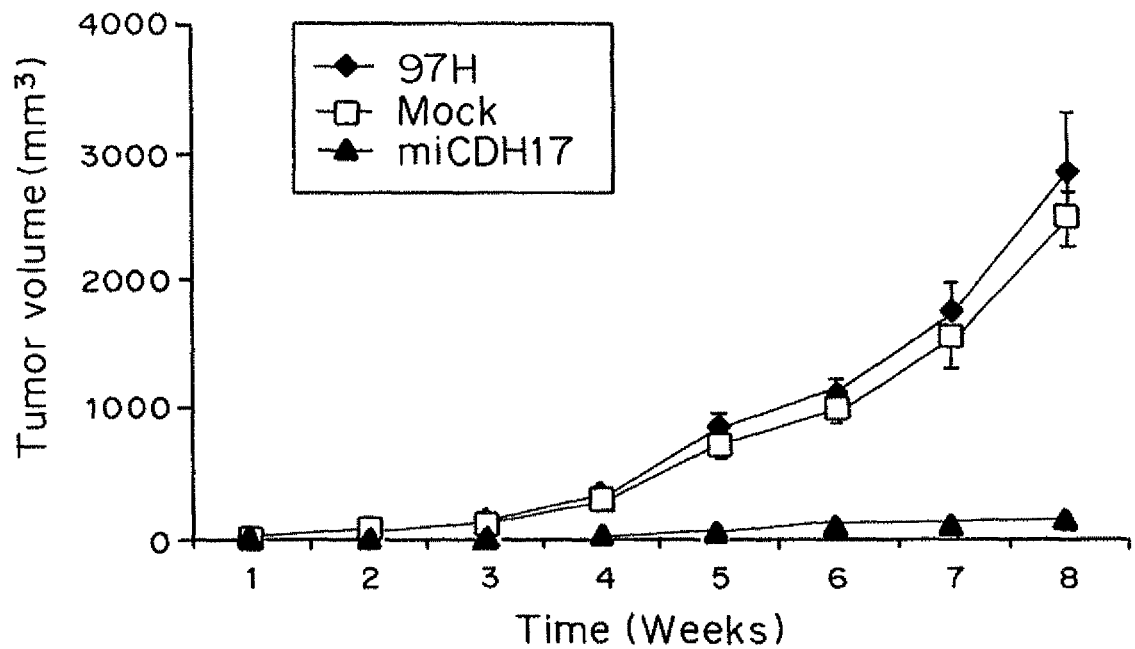
FIG. 1 is a graph showing the reduction over time (weeks) in size of tumor xenograft ($mm^3$) after silencing the expression of CDH17 in MHCC97-H (97H) liver tumor cells.

The terms "body fluid" and "bodily fluid", as used herein, refer to a composition obtained from a human or animal subject. Bodily fluids include, but are not limited to, urine, whole blood, blood plasma, serum, tears, semen, saliva, sputum, exhaled breath, nasal secretions, pharyngeal exudates, bronchoalveolar lavage, tracheal aspirations, interstitial fluid, lymph fluid, meningal fluid, amniotic fluid, glandular fluid, feces, perspiration, mucous, vaginal or urethral secretion, cerebrospinal fluid, and transdermal exudate. Bodily fluid also includes experimentally separated fractions of all of the preceding solutions or mixtures containing homogenized solid material, such as feces, tissues, and biopsy samples.

The term "ex vivo," as used herein, refers to an environment outside of a subject. Accordingly, a sample of bodily fluid collected from a subject is an ex vivo sample of bodily As used herein, the term "conjugate" refers to a compound comprising two or more molecules bound together, optionally through a linking group, to form a single structure. The binding can be made by a direct connection (e.g., a chemical bond) between the molecules or by use of a linking group.

As used herein, the terms solid "support", "substrate", and "surface" refer to a solid phase which is a porous or non-porous water insoluble material that can have any of a number of shapes, such as strip, rod, particle, beads, or multi-welled plate.

As used herein, the term "tumor" refers to all neoplastic cell growth and proliferation, whether malignant or benign, and all pre-cancerous and cancerous cells and tissues. For example, a particular cancer may be characterized by a solid mass tumor. The solid tumor mass, if present, may be a primary tumor mass. A primary tumor mass refers to a growth of cancer cells in a tissue resulting from the transformation of a normal cell of that tissue. In most cases, the primary tumor mass is identified by the presence of a cyst, which can be found through visual or palpation methods, or by irregularity in shape, texture or weight of the tissue. However, some primary tumors are not palpable and can be detected only through medical imaging techniques such as X-rays (e.g., mammography), ultrasound, CT, and MRI, or by needle aspirations. The use of these latter techniques is more common in early detection. Molecular and phenotypic analysis of cancer cells within a tissue will usually confirm if the cancer is endogenous to the tissue or if the lesion is due to metastasis from another site.

A "sample" (biological sample) can be any composition of matter of interest from a human or non-human subject, in any physical state (e.g., solid, liquid, semi-solid, vapor) and of any complexity. The sample can be any composition reasonably suspected of containing CDH17 that can be analyzed by the disclosed methods, devices, and kits. Preferably, the sample is a fluid (biological fluid). The sample may be contained within a test tube, culture vessel, multi-well plate, or any other container or supporting substrate. The sample can be, for example, a cell culture or human tissue. Fluid homogenates of cellular tissues are biological fluids that may contain CDH17 for detection according to the disclosed methods. Others are fluid tissues, for example, blood or urine.

The "complexity" of a sample refers to the relative number of different molecular species that are present in the sample.

As used herein, the terms "label" and "tag" refer to substances that may confer a detectable signal.

As used herein, the term "receptor" and "receptor protein" are used herein to indicate a biologically active proteinaceous molecule that specifically binds to (or with) other molecules such as CDH17.

As used herein, the term "ligand" refers to a molecule that contains a structural portion that is bound by specific interaction with a particular receptor protein.

As used herein, the term "antibody" refers to immunoglobulin molecules and immunologically active portions (fragments) of immunoglobulin molecules, i.e., molecules that contain an antibody combining site or paratope. The term is inclusive of monoclonal antibodies, polyclonal antibodies and fragments and single chain recombinant antibodies.

As used here, the terms "monoclonal antibody" or "monoclonal antibody composition" refer to an antibody molecule that contains only one species of antibody combining site capable of immunoreacting with a particular antigen.

A "coding sequence" or "coding region" is a polynucleotide sequence that is transcribed into mRNA and/or translated into a polypeptide. For example, a coding sequence may encode a polypeptide of interest. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

As used herein, the term "polypeptide" refers to any polymer comprising any number of amino acids, and is interchangeable with "protein", "gene product", and "peptide".

As used herein, the term "nucleoside" refers to a molecule having a purine or pyrimidine base covalently linked to a ribose or deoxyribose sugar. Exemplary nucleosides include adenosine, guanosine, cytidine, uridine and thymidine.

The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms. The terms "nucleic acid" or "nucleic acid sequence" encompass an oligonucleotide, nucleotide, polynucleotide, or a fragment of any of these, DNA or RNA of genomic or synthetic origin, which may be single-stranded or double-stranded and may represent a sense or antisense strand, peptide nucleic acid (PNA), or any DNA-like or RNA-like material, natural or synthetic in origin. As will be understood by those of skill in the art, when the nucleic acid is RNA, the deoxynucleotides A, G, C, and T are replaced by ribonucleotides A, G, C, and U, respectively.

As used herein, the term "RNA" or "RNA molecule" or "ribonucleic acid molecule" refers generally to a polymer of ribonucleotides. The term "DNA" or "DNA molecule" or deoxyribonucleic acid molecule" refers generally to a polymer of deoxyribonucleotides. DNA and RNA molecules can be synthesized naturally (e.g., by DNA replication or transcription of DNA, respectively). RNA molecules can be post-transcriptionally modified. DNA and RNA molecules can also be chemically synthesized. DNA and RNA molecules can be single-stranded (i.e., ssRNA and ssDNA, respectively) or multi-stranded (e.g., double stranded, i.e., dsRNA and dsDNA, respectively). The term "RNA" or "RNA molecule" or "ribonucleic acid molecule" can also refer to a polymer comprising primarily (i.e., greater than 80% or, preferably greater than 90%) ribonucleotides but optionally including at least one non-ribonucleotide molecule, for example, at least one deoxyribonucleotide and/or at least one nucleotide analog.

As used herein, the term "nucleotide analog", also referred to herein as an "altered nucleotide" or "modified nucleotide" refers to a non-standard nucleotide, including non-naturally occurring ribonucleotides or deoxyribonucleotides. Preferred nucleotide analogs are modified at any position so as to alter certain chemical properties of the nucleotide yet retain the ability of the nucleotide analog to perform its intended function.

As used herein, the term "RNA analog" refers to a polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. Exemplary RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference or otherwise reduce target gene expression.

As used here, the terms "monoclonal antibody" or "monoclonal antibody composition" refer to an antibody molecule that contains only one species of antibody combining site capable of immunoreacting with a particular antigen. A monoclonal antibody composition thus typically displays a single binding affinity for any antigen with which it immunoreacts.

As used herein, the term "ELISA" includes an enzyme-linked immunosorbent assay that employs an antibody or antigen bound to a solid phase and an enzyme-antigen or enzyme-antibody conjugate to detect and quantify the amount of an antigen (e.g., CDH17) or antibody present in a sample.

As used herein, the terms "subject", "patient", and "individual" are used interchangeably and intended to include such human and non-human mammalian species. Likewise, in vitro methods can be carried out on cells of such mammalian species. Host cells comprising exogenous polynucleotides as disclosed herein may be administered to the subject, and may, for example, be autogenic (use of one's own cells), allogenic (from one person to another), or transgenic or xenogenic (from one mammalian species to another mammalian species), relative to the subject.

A cell proliferative disorder as described herein may be a neoplasm. Such neoplasms are either benign or malignant. The term "neoplasm" refers to a new, abnormal growth of cells or a growth of abnormal cells that reproduce faster than normal. A neoplasm creates an unstructured mass (a tumor) which can be either benign or malignant. The term "benign" refers to a tumor that is noncancerous, e.g., its cells do not invade surrounding tissues or metastasize to distant sites. The term "malignant" refers to a tumor that is metastatic, invades contiguous tissue or no longer under normal cellular growth control.

As used herein, "a clinical response" is the response of a subject to modulation of the gene of interest. Criteria for determining a response to therapy are widely accepted and enable comparisons of the efficacy alternative treatments (see Slapak and Kufe, Principles of Cancer Therapy, in Harrisons's Principles of Internal Medicine, 13$^{th}$ edition, eds. Isselbacher et al., McGraw-Hill, Inc. 1994). A complete response (or complete remission) is the disappearance of all detectable malignant disease. A partial response is an approximately 50 percent decrease in the product of the greatest perpendicular diameters of one or more lesions. There can be no increase in size of any lesion or the appearance of new lesions. Progressive disease means at least an approximately 25 percent increase in the product of the greatest perpendicular diameter of one lesion or the appearance of new lesions. The response to treatment is evaluated after the subjects had completed therapy.

As used herein, the terms "administer", "introduce", "apply", "treat", "transplant", "implant", "deliver", and grammatical variations thereof, are used interchangeably to provide CDH17 inhibitors to target cells in vitro (e.g., ex vivo) or in vivo, or provide genetically modified (engineered) cells harboring the CDH17 inhibitors to a subject.

As used herein, the term "co-administration" and variations thereof refers to the administration of two or more agents simultaneously (in one or more preparations), or consecutively. For example, one or more types of genetically modified cells can be co-administered with other agents.

As used herein, the terms "label" and "tag" refer to substances that may confer a detectable signal. include, but are not limited to, enzymes such as alkaline phosphatase, glucose-6-phosphate dehydrogenase, and horseradish peroxidase, ribozyme, a substrate for a replicase such as QB replicase, promoters, dyes, fluorescers, such as fluorescein, isothiocynate, rhodamine compounds, phycoerythrin, phycocyanin, allophycocyanin, o-phthaldehyde, and fluorescamine, chemiluminescers such as isoluminol, sensitizers, coenzymes, enzyme substrates, radiolabels, particles such as latex or carbon particles, liposomes, cells, etc., which may be further labeled with a dye, catalyst or other detectable group.

As used herein, a semi-permeable membrane refers to a bio-compatible material which is impermeable to liquids and capable of allowing the transfer of gases through it. Such gases include, but are not limited to, oxygen, water vapor, and carbon dioxide. Semi-permeable membranes are an example of a material that can be used to form a least a portion of an enclosure defining a flow chamber cavity. The semi-permeable membrane may be capable of excluding microbial contamination (e.g., the pore size is characteristically small enough to exclude the passage of microbes that can contaminate the analyte, such as cells). In a particular aspect, a semi-permeable membrane can have an optical transparency and clarity sufficient for permitting observation of an analyte, such as cells, for color, growth, size, morphology, imaging, and other purposes well known in the art.

As used herein, the term "bind" refers to any physical attachment or close association, which may be permanent or temporary. The binding can result from hydrogen bonding, hydrophobic forces, van der Waals forces, covalent, or ionic bonding, for example.

As used herein, the term "diagnosis" or "diagnostic" generally includes determination of a subject's susceptibility to a disease or disorder, determination as to whether a subject is presently affected by a disease or disorder, prognosis of a subject affected by a disease or disorder (e.g., identification of pre-metastatic or metastatic cancerous states, stages of cancer, or responsiveness of cancer to therapy), and therametrics (e.g., monitoring a subject's condition to provide information as to the effect or efficacy of therapy).

As used herein, the term "particle" includes insoluble materials of any configuration, including, but not limited to, spherical, thread-like, brush-like, and irregular shapes. Particles can be porous with regular or random channels inside. Particles can be magnetic. Examples of particles include, but are not limited to, silica, cellulose, Sepharose beads, polystyrene (solid, porous, derivatized) beads, controlled-pore glass, gel beads, magnetic beads, sols, biological cells, subcellular particles, microorganisms (protozoans, bacteria, yeast, viruses, and other infectious agents), micelles, liposomes, cyclodextrins, and other insoluble materials.

The terms "operably-linked" or "operatively-linked" are used herein interchangeably to refer to an arrangement of flanking sequences wherein the flanking sequences so described are configured or assembled so as to perform their usual function. Thus, a flanking sequence operably-linked to a coding sequence may be capable of effecting the replication, transcription and/or translation of the coding sequence. For example, a coding sequence is operably-linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence, and the promoter sequence can still be considered "operably-linked" to the coding sequence. Each nucleotide sequence coding for a siRNA will typically have its own operably-linked promoter sequence.

The term "vector" is used to refer to any molecule (e.g., nucleic acid, plasmid, or virus) used to transfer coding information (e.g., a CDH17 polynucleotide inhibitor) to a host cell. The terms "expression vector" and "transcription vector" are used interchangeably to refer to a vector that is suitable for use in a host cell (e.g., a subject's cell) and contains nucleic acid sequences that direct and/or control the expression of exogenous nucleic acid sequences. Expression includes, but is not limited to, processes such as transcription, translation, and RNA splicing, if introns are present.

As used herein, the term "RNA interference" ("RNAi") refers to a selective intracellular degradation of RNA. RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of endogenous target genes, such as CDH17.

As used herein the terms "cancer", "tumor", and "carcinoma", are used interchangeably herein to refer to cells which exhibit relatively autonomous growth, so that they exhibit an aberrant growth phenotype characterized by a significant loss of control of cell proliferation. In general, cells of interest for detection or treatment in the present application include pre-cancerous (e.g., benign), malignant, metastatic, and non-metastatic cells. Detection of cancerous cell is of particular interest.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference.

As used herein, a siRNA having a "sequence sufficiently complementary to a target mRNA sequence to direct target-specific RNA interference (RNAi)" means that the siRNA has a sequence sufficient to trigger the destruction of the target mRNA (e.g., CDH17 mRNA) by the RNAi machinery or process. "mRNA" or "messenger RNA" or "transcript" is single-stranded RNA that specifies the amino acid sequence of one or more polypeptides. This information is translated during protein synthesis when ribosomes bind to the mRNA.

As used herein, the term "cleavage site" refers to the residues, e.g., nucleotides, at which RISC* cleaves the target RNA, e.g., near the center of the complementary portion of the target RNA, e.g., about 8-12 nucleotides from the 5' end of the complementary portion of the target RNA.

The term "dominant negative mutant" is art-recognized and refers to the mutant form of a wild-type protein that interferes with the function of the wild-type protein (e.g., by interacting with the wild-type protein). Thus, overexpression of the dominant negative mutant can be expected to interfere with the function of the wild-type version of the protein.

As used herein, the term "mismatch" refers to a base-pair consisting of noncomplementary bases, e.g., not normal complementary G:C, A:T or A:U base pairs.

As used herein, the term "isolated" molecule (e.g., isolated nucleic acid molecule) refers to molecules which are substantially free of other cellular material, or culture medium when produced by recombinant techniques, or substantially free of chemical precursors or other chemicals when chemically synthesized.

As used herein, the term "in vitro" has its art recognized meaning, e.g., involving purified reagents or extracts, e.g., cell extracts. The term "in vivo" also has its art recognized meaning, e.g., involving living cells in an organism, e.g., immortalized cells, primary cells, and/or cell lines, in an organism.

The terms "detecting" or "detect" include assaying or otherwise establishing the presence or absence of the target CDH17 (CDH17 encoding nucleic acid sequence or CDH17 gene product (polypeptide)), subunits thereof, or combinations of agent bound targets, and the like, or assaying for, interrogating, ascertaining, establishing, or otherwise determining one or more factual characteristics of liver cancer, metastasis, stage, or similar conditions. The term encompasses diagnostic, prognostic, and monitoring applications for CDH17 and other cancer biomarkers. The term encompasses quantitative, semi-quantitative, and qualitative detection methodologies. In embodiments involving detection of CDH17 protein (as opposed to nucleic acid molecules encoding CDH17 protein), the detection method is preferably an ELISA-based method. Preferably, the detection method provides an output (i.e., readout or signal) with information concerning the presence, absence, or amount of CDH17 in a sample from a subject. For example, the output may be qualitative (e.g., "positive" or "negative"), or quantitative (e.g., a concentration such as nanograms per milliliter).

II. CDH17 Compounds

The compositions and methods of use thereof are based on the discovery that levels of CDH17 are positively correlated with liver cancer and can be detected at low levels with sensitivity and selectivity.

CDH17 is a member of the cadherin family of transmembrane proteins often associated with cellular structural organization and cellular adhesion. The cadherin family is separated into members showing common organ or cellular specificities. The cadherin CDH17 is associated with the liver and gastrointestinal system. Overexpression of CDH17 has been demonstrated in HCC, enabling the use of the CDH17 molecule as a tumor biomarker for liver cancers in humans. CDH17 exists in a unique truncated form in the serum of patients with liver cancer. The cadherin-17 (CDH17), or LI cadherin (liver intestine-cadherin), gene is a member of the cadherin family of genes encoding calcium-dependent and membrane-associated glycoproteins. The expressed CDH17 protein consists of an extracellular region, containing 7 cadherin domains, a transmembrane region, and a cytoplasmic tail that differs from the conserved cadherin cytoplasmic domain. CDH17 exists as a peptide transporter of the gastrointestinal tract and pancreatic ducts. Also, CDH17 may play a role in the structural organization of liver and intestine.

The cadherin superfamily consists of several cadherin subfamilies, including type I and type II classical cadherins. The cadherins often play important roles in cell adhesion, ensuring that cells within tissues are bound together. They are dependent on calcium ($Ca^{2+}$) ions to function. The differing classes of cadherins are commonly designated with a one-letter prefix noting the type of tissue with which it is associated (see Table 1). Cadherins within one class will often bind to themselves (homotypic interactions). For example, an N-cadherin will bind to another N-cadherin molecule. In addition, cadherins will also mediate heterotypic interactions in some instances.

TABLE 1

| Cadherins - human |
| --- |
| CDH1 - E-cadherin (epithelial) |
| CDH2 - N-cadherin (neural) |
| CDH3 - P-cadherin (placental) |
| CDH4 - R-cadherin (retinal) |
| CDH5 - VE-cadherin (vascular endothelial) |
| CDH6 - K-cadherin (kidney) |
| CDH7 - cadherin-7 |
| CDH8 - cadherin-8 |
| CDH9 - cadherin-9 (T1-cadherin) |
| CDH10 - cadherin-10 (T2-cadherin) |
| CDH11 - OB-cadherin (osteoblast) |
| CDH12 - cadherin-12(N-cadherin 2) |
| CDH13 - T-cadherin (truncated)/H-cadherin (heart) |
| CDH15 - M-cadherin (muscle) |
| CDH16 - Ksp-cadherin (Kidney-specific) |
| CDH17 - LI cadherin (liver intestine) |
| CDH18 - cadherin-18, (synonym: CDH14) |
| CDH19 - cadherin-19 |
| CDH20 - cadherin-20 |

CDH17 has previously been implicated as a predictive protein for metastasis and prognosis in gastric cancer (Park S S et al., *Ann Surg Oncol* 2007; 14(1):94-9; Ito R et al., *Virchows Arch* 2005; 447(4):717-22). CDH17 expression has also been linked to prognosis in colorectal cancer (Kwak J M et al., *Dis Colon Rectum* 2007; 50(11):1873-80). Takamura et al. found that reduced expression of CDH17 correlated to progression of colorectal carcinoma and higher rates of metastasis (Takamura M et al., *Cancer Lett* 2004; 212(2):253-59).

CDH17 possessed a possible genetic risk association to HCC based upon two single nucleotide polymorphisms. Wang X Q et al., *Clin Cancer Res* 2006; 12(17):5248-52. Further, CDH17 was found to have aberrant splicing of its transcripts associated with HCC. Wang X Q et al., *Clin Cancer Res* 2005; 11:483-489. However, the overexpression and aberrant splicing of CDH17 in HCC, without more, did not offer a prospective use in the diagnosis or treatment of HCC. Of particular importance in evaluating the significance of such disclosures, serum levels of soluble intercellular adhesion molecule-1, soluble interleukin-2 receptor, interleukin-6, and anti-p53 were examined by an Italian laboratory and it was concluded that these markers were not useful for the diagnosis and did not correlate with prognosis of hepatocellular carcinoma (Parasole, et al., *Clin Cancer Res,* 7:3504-3509 (2001)). In addition, CDH17 was not found to be increased in the serum of rats affected with liver diseases (Lucka, et al., *FEBS Lett,* 438:37-40 (1998)).

I. CDH17 Inhibitors/Antagonists (A) Polynucleotide CDH 17 Inhibitors/Antagonists The CDH17 molecule can be used as a target for molecular therapy for liver cancers. Silencing the expression of CDH17 in liver cancer cells alleviates the tumor phenotypes. The suppression of CDH17 expression has also been found to render tumor cells more sensitive to certain chemotherapeutic drugs and p53-based gene therapy. Once diagnosed, CDH17-targeted therapy utilizing anti-CDH17 monoclonal antibodies or small interfering RNA (siRNA), for example, can inhibit tumor progression and sensitize the tumor cells to the current chemotherapeutic treatment modalities. In addition, treatment of HCC with CDH17 antagonists such as monoclonal antibodies or siRNA directed against CDH17 will improve the efficacy of currently limited HCC therapy.

A CDH17 antagonist suppressing the expression of CDH17 leads to a significant reduction of tumor size in nude mice, for which the tumor xenograft is derived from liver cancer cells having increased expression of CDH17. When the expression of CDH17 is suppressed in liver tumor cells that overexpress the cadherin, the tumor cells are rendered more sensitive to current therapies that involve the use of chemotherapeutic drugs and the application of gene therapy.

A CDH17 antagonist/inhibitor as used herein is a compound that specifically binds to CDH17, preferably human CDH17 or binds to a CDH17 polynucleotide or fragment thereof, and inhibits the activity and/or expression of CDH17 protein or polynucleotide. Examples thereof include ligands that bind CDH17 such as antibodies and antibody fragments, recombinant or native. Other examples include antisense oligonucleotides that bind to a CDH17 polynucleotide or fragment thereof. In a preferred embodiment, the CDH17 antagonist is a ShRNA.

(i) ShRNA

The polynucleotide CDH17 inhibitors can be small hairpin RNAs (shRNAs), and expression constructs engineered to express shRNAs. Transcription of shRNAs is initiated at a polymerase III (pol III) promoter, and is thought to be terminated at position 2 of a 4-5-thymine transcription termination site. Upon expression, shRNAs are thought to fold into a stem-loop structure with 3' UU-overhangs; subsequently, the ends of these shRNAs are processed, converting the shRNAs into siRNA-like molecules of about 21 nucleotides (Brummelkamp et al., *Science* 296:550-553 (2002); Lee et al., *Nature Biotechnol.* 20:500-505 (2002); Miyagishi and Taira, *Nature Biotechnol.* 20:497-500 (2002); Paddison et al., *Genes Dev.* 16:948-958 (2002); Paul et al., *Nature Biotechnol.* 20:505-508 (2002); Sui (2002) supra; Yu et al., *Proc. Natl. Acad. Sci.* USA 99(9):6047-6052 (2002).

In a preferred embodiment, the RNA hairpin sequence used to knockdown expression of CDH17 by targeting Exon 3 is TGCTGTTGACAGTGAGCGACCAAGAAC-CGAGTCAAATTATTAGT GAAGCCACAGATG-TAATAATTTGACTCGGTTCTTGGCTGCCTACTGCCT CGGA (SEQ ID NO: 2).

The forward portion of the shRNA duplex for targeting Exon 5 is GATCCCGCCAGTCCCTATCACCATA-GAGAAGCTTGTCTATGGTGA TAGGGACTGGTTTTTT (SEQ ID NO: 3) and the reverse portion of the shRNA duplex for targeting exon 5 is CTAGAAAAAACCAGTCCCTAT-CACCAT AGACAAGCTTCTCTATGGTGATAGGGACTG GCGG (SEQ ID NO: 4).

RNA Interference

RNAi is an efficient process whereby double-stranded RNA (dsRNA, also referred to herein as siRNAs or ds siR-NAs, for double-stranded small interfering RNAs) induces the sequence-specific degradation of targeted mRNA in animal and plant cells (Hutvagner and Zamore, *Curr. Opin. Genet. Dev.:* 12, 225-232 (2002); Sharp, *Genes Dev.,* 15:485-490 (2001)). In mammalian cells, RNAi can be triggered by 21-nucleotide (nt) duplexes of small interfering RNA (siRNA) (Chiu et al., *Mol. Cell.* 10:549-561 (2002); Elbashir et al., *Nature* 411:494-498 (2001)), or by micro-RNAs (miRNA), functional small-hairpin RNA (shRNA), or other dsRNAs which can be expressed in vivo using DNA templates with RNA polymerase III promoters (Zeng et al., *Mol. Cell* 9:1327-1333 (2002); Paddison et al., *Genes Dev.* 16:948-958 (2002); Lee et al., *Nature Biotechnol.* 20:500-505 (2002); Paul et al., *Nature Biotechnol.* 20:505-508 (2002); Tuschl, T., *Nature Biotechnol.* 20:440-448 (2002); Yu et al., *Proc. Natl. Acad. Sci.* USA 99(9):6047-6052 (2002); McManus et al., *RNA* 8:842-850 (2002); Sui et al., *Proc. Natl. Acad. Sci.* USA 99(6):5515-5520 (2002)), each of which are incorporated herein by reference in their entirety.

The scientific literature contains many reports of endogenous and exogenous gene expression silencing using siRNA, highlighting their therapeutic potential (Gupta, S. et al. *PNAS,* 2004, 101:1927-1932; Takaku, H. *Antivir Chem. Chemother,* 2004, 15:57-65; Pardridge, W. M. *Expert Opin. Biol. Ther.,* 2004, 4:1103-1113; Zheng, B. J. *Antivir. Ther.,* 2004, 9:365-374; Shen, W. G. *Chin. Med. J. (Engl),* 2004, 117:1084-1091; Fuchs, U. et al. *Curr. Mol. Med.,* 2004, 4:507-517; Wadhwa, R. et al. *Mutat. Res.,* 2004, 567:71-84; Ichim, T. E. et al. *Am. J. Transplant,* 2004, 4:1227-1236; Jana, S. et al. *Appl. Microbiol. Biotechnol.,* 2004, 65:649-657; Ryther, R. C. et al. *Gene Ther.,* 2005, 12:5-11; Chae, S-S. et al., *J. Clin. Invest.,* 2004, 114:1082-1089; Fougerolles, A. et al., *Methods Enzymol.,* 2005, 392:278-296), each of which is incorporated herein by reference in its entirety. Therapeutic silencing of endogenous genes by systemic administration of siRNAs has been described in the literature (Kim B. et al., *American Journal of Pathology,* 2004, 165:2177-2185; Soutschek J. et al., *Nature,* 2004, 432:173-178; Pardridge W. M., *Expert Opin. Biol. Ther.,* 2004, Jul., 4(7):1103-1113), each of which is incorporated herein by reference in its entirety.

Accordingly, the pharmaceutical composition contains an effective amount of such interfering RNA molecules that are targeted to CDH17 mRNA. The interfering RNA molecules are capable, when suitably introduced into or expressed within a cell that otherwise expresses CDH17 mRNA, of suppressing expression of the CDH17 gene by RNAi. The interfering RNA may be a double-stranded siRNA. An siRNA molecule may include a short 3' DNA sequence also. Alternatively, the nucleic acid may be a DNA (usually double-stranded DNA) which, when transcribed in a cell, yields an RNA having two complementary portions joined via a spacer, such that the RNA takes the form of a hairpin when the complementary portions hybridize with each other. In a mammalian cell, the hairpin structure may be cleaved from the molecule by the enzyme Dicer, to yield two distinct, but hybridized, RNA molecules.

(ii) siRNA Molecules

Short interfering RNAs (siRNAs) induce the sequence-specific suppression or silencing (i.e., reducing expression which may be to the extent of partial or complete inhibition) genes by the process of RNAi. Thus, siRNA is the intermediate effector molecule of the RNAi process. The interfering RNA that function as CDH17 inhibitors include dsRNA molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the CDH17 mRNA, and the other strand is identical or substantially identical to the first strand. The dsRNA molecules that function as CDH17 inhibitors can be chemically synthesized, or can be transcribed in vitro from a DNA template, or in vivo from, e.g., shRNA. The dsRNA molecules can be designed using any method known in the art, for instance, by using the following protocol:

1. Using any method known in the art, compare the potential targets to the appropriate genome database (human, mouse, rat, etc.) and eliminate from consideration any target sequences with significant homology to other coding sequences. One such method for sequence homology searches is known as BLAST, which is available at the National Center for Biotechnology Information (NCBI) web site of the National Institutes of Health. Also available on the NCBI webs site is the HomoloGene database, which is a publicly available system for automated detection of homologs among the annotated genes of several completely sequenced eukaryotic genomes and is readily utilized by those of ordinary skill in the art.

2. Select one or more sequences that meet your criteria for evaluation. Further general information regarding the design and use of siRNA can be found in "The siRNA User Guide," available at the web site of the laboratory of Dr. Thomas Tuschl at Rockefeller University (Elbashir et al., *EMBO J.*, 20:6877-6888 (2001).

3. Negative control siRNAs preferably have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Initially, basic criteria were defined for identification of efficient siRNA, such as GC content and position of the targeted sequence in the context of the mRNA (Elbashir S M. et al., *Methods,* 26:199-213 (2002)). Further progress was achieved more recently, when the assembly of the RNAi enzyme complex was described as being dependent on thermodynamic characteristics of the siRNA (Khrvorova A. et al., *Cell,* 115:209-216 (2003); Schwarz D. S. et al., *Cell,* 115:199-208 (2003)). The relative stability of both ends of the duplex was determined to have effects on the extent to which the individual strands enter the RNAi pathway. In addition, certain sequence motifs at defined positions of the siRNA were reported to influence its potency (Amarzguioui, et al., *Biochem. Biophys. Res. Commun.,* 316:1050-1058 (2004); Reynolds et al., *Nature Biotechnol.,* 22:326-330 (2004)). On this basis, sophisticated algorithms have been developed to increase the success rate of siRNA design and are available to those skilled in the art (Amarzguioui, et al., 2004; Reynolds, et al., 2004; and Ui-Tei, et al., *Nucl. Acids Res.,* 32:936-948 (2004), each of which is incorporated herein in its entirety). Other computational tools that may be used to select siRNAs in Yuan, et al., *Nucleic Acids Research,* Vol. 32, W130-W134, (2004) and Bonetta, *Nature Methods,* 1(1):79-86) (2004), each of which are incorporated by reference herein in their entirety.

Strategies for rational design of effective interfering RNA are disclosed in Gong, et al., *Trends in Biotechnol.,* 22(9):451 (2004); Schubert, et al., *J. Mol. Biol.,* 348:883-893 (2005); Pancoska, et al., *Nucleic Acids Res.,* 32(4):1469-1479 (2004); and Mittal, *Nat. Rev. Genet.,* 5(5):355-365 (2004) (each of which is incorporated herein by reference in its entirety).

Screening for the most efficient siRNAs using cell cultures may be carried out as disclosed for example in Yang D. et al., *Proc. Natl. Acad. Sci. USA,* 2002, 99:9942-9947; Myers J. W. et al., *Nat. Biotechnol.,* 2003, 21:324-328). The short RNAs produced as a result of these digestions have been found to be efficient in RNAi. Oligonucleotide arrays can also be used for the efficient preparation of defined mixtures of siRNAs for reducing the expression of exogenous and endogenous genes such as CDH17 (Oleinikov A. V. et al., *Nucleic Acids Research,* 2005, 33(10):e92).

Unmodified siRNAs and modified siRNAs can be used. Thus, siRNA derivatives that include siRNA having two complementary strands of nucleic acid, such that the two strands are crosslinked can be employed. For example, a 3' OH terminus of one of the strands can be modified, or the two strands can be crosslinked and modified at the 3' OH terminus. The siRNA derivative can contain a single crosslink (e.g., a psoralen crosslink). In some embodiments, the siRNa can be conjugated to another moiety, such as a nanoparticle, to enhance a property of the compositions, e.g., a pharmacokinetic parameter such as absorption, efficacy, bioavailability, and/or half-life. In these embodiments, the siRNA derivative would for example, have at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying siRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The conjugation can be accomplished by methods known in the art, e.g., using the methods known in the art as disclosed for example in Lambert et al., *Drug Deliv. Rev.* 47(1): 99-112 (2001); Fattal et al., *J. Control Release* 53(1-3):137-43 (1998); Schwab et al., *Ann. Oncol.* 5 Suppl. 4:55-8 (1994); and Godard et al., *Eur. J. Biochem.* 232(2):404-10 (1995).

The siRNA can also be labeled using any method known in the art; for instance, nucleic acids can be labeled with a fluorophore, e.g., Cy3, fluorescein, or rhodamine. The labeling can be carried out using a kit, e.g., the SILENCER siRNA labeling kit (AMBION). Additionally, the siRNA can be radiolabeled, e.g., using $^{3}$H, $^{32}$P, or other appropriate isotope.

Because RNAi is believed to progress via at least one single stranded RNA intermediate, the skilled artisan will appreciate that ss-siRNAs (e.g., the antisense strand of a ds-siRNA) can also be designed as described herein and utilized according to the claimed methodologies.

There are a number of companies that will generate interfering RNAs for a specific gene. Thermo Electron Corporation (Waltham, Mass.) has launched a custom synthesis service for synthetic short interfering RNA (siRNA). Each strand is composed of 18-20 RNA bases and two DNA bases overhang on the 3' terminus. Dharmacon, Inc. (Lafayette, Colo.) provides siRNA duplexes using the 2'-ACE RNA synthesis technology. Qiagen (Valencia, Calif.) uses TOM-chemistry to offer siRNA with high individual coupling yields (Li, et al., *Nat. Med.,* 11(9):944-951 (2005).

SiRNAs targeting CDH17 mRNA may be fused to other nucleotide molecules, or to polypeptides, in order to direct their delivery or to accomplish other functions. Thus, for example, fusion proteins comprising a siRNA oligonucleotide that is capable of specifically interfering with expression of CDH17 may comprise affinity tag polypeptide sequences, which refers to polypeptides or peptides that facilitate detection and isolation of the polypeptide via a specific affinity interaction with a ligand. The ligand may be any molecule, receptor, counter-receptor, antibody or the like with which the affinity tag may interact through a specific binding interaction as provided herein. Such peptides include, for example, poly-His or "FLAG" or the like, e.g., the antigenic identification peptides described in U.S. Pat. No. 5,011,912 and in Hopp et al., (*Bio/Technology* 6:1204, 1988), or the XPRESS epitope tag (INVITROGEN, Carlsbad, Calif.). The affinity sequence may be a hexa-histidine tag as supplied, for example, by a pBAD/His (INVITROGEN) or a pQE-9 vector to provide for purification of the mature polypeptide fused to the marker in the case of a bacterial host, or, for example, the affinity sequence may be a hemagglutinin (HA) tag when a mammalian host, e.g., COS-7 cells, is used. The HA tag corresponds to an antibody defined epitope derived from the influenza hemagglutinin protein (Wilson et al., 1984 *Cell* 37:767).

(iii) Antisense Oligonucleotides

An "antisense" nucleic acid sequence (antisense oligonucleotide) can include a nucleotide sequence that is complementary to a "sense" nucleic acid encoding a protein, e.g., complementary to the coding strand of a double-stranded cDNA molecule or complementary to the CDH17 mRNA. Antisense nucleic acid sequences and delivery methods are well known in the art (Goodchild, *Curr. Opin. Mol. Ther.*, 6(2):120-128 (2004); Clawson, et al., *Gene Ther.*, 11(17): 1331-1341 (2004)), which are incorporated herein by reference in their entirety. The antisense nucleic acid can be complementary to an entire coding strand of a target sequence, or to only a portion thereof. In another embodiment, the antisense nucleic acid molecule is antisense to a "noncoding region" of the coding strand of a nucleotide sequence within the CDH17 mRNA. An antisense oligonucleotide can be, for example, about 7, 10, 15, 20, 25, 30, 35, 40, 45, 50, 55, 60, 65, 70, 75, 80, or more nucleotides in length.

An antisense nucleic acid sequence can be designed such that it is complementary to the entire CDH17 mRNA sequence, but can also be an oligonucleotide that is antisense to only a portion of the CDH17 mRNA. For example, the antisense oligonucleotide can be complementary to a portion of the CDH17 enzymatic domain (inositol 5'-phosphatase domain) or a portion of the amino-terminal src-homology domain (SH2).

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

Other examples of useful antisense oligonucleotides include an alpha-anomeric nucleic acid. An alpha-anomeric nucleic acid molecule forms specific double-stranded hybrids with complementary RNA in which, contrary to the usual beta-units, the strands run parallel to each other (Gaultier et al., *Nucleic Acids. Res.* 15:6625-6641 (1987)). The antisense nucleic acid molecule can also comprise a 2'-o-methylribonucleotide (Inoue et al. *Nucleic Acids Res.* 15:6131-6148 (1987)) or a chimeric RNA-DNA analogue (Inoue et al. *FEBS Lett.*, 215:327-330 (1987)).

(iv) Ribozymes

Ribozymes are a type of RNA that can be engineered to enzymatically cleave and inactivate other RNA targets in a specific, sequence-dependent fashion. Ribozymes and methods for their delivery are well known in the art (Hendry, et al., *BMC Chem. Biol.*, 4(1):1 (2004); Grassi, et al., *Curr. Pharm. Biotechnol.*, 5(4):369-386 (2004); Bagheri, et al., *Curr. Mol. Med.*, 4(5):489-506 (2004); Kashani-Sabet M., *Expert Opin. Biol. Ther.*, 4(11):1749-1755 (2004), each of which are incorporated herein by reference in its entirety. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art.

A ribozyme having specificity for CDH17 mRNA can include one or more sequences complementary to a nucleotide sequence within the CDH17 mRNA, and a sequence having a known catalytic sequence responsible for mRNA cleavage (see U.S. Pat. No. 5,093,246 or Haselhoff, et al., *Nature* 334:585-591 (1988)). For example, a derivative of a Tetrahymena L-19 IVS RNA can be constructed in which the nucleotide sequence of the active site is complementary to the nucleotide sequence to be cleaved in the mRNA encoded by a uORF of an extended, overlapping 5'-UTR AS mRNA species (see, e.g., U.S. Pat. No. 4,987,071 and No. 5,116,742). Alternatively, CDH17 mRNA can be used to select a catalytic RNA having a specific ribonuclease activity from a pool of RNA molecules (Bartel, et al., *Science*, 261:1411-1418 (1993)).

(v) Vectors and Constructs

Also provided are vectors and constructs that include or encode polynucleotide CDH17 inhibitors (e.g., siRNA), and in particular to "recombinant nucleic acid constructs" that include any nucleic acid such as a DNA polynucleotide segment that may be transcribed to yield CDH17-specific siRNA polynucleotides inhibitors, host cells which are genetically engineered with vectors and/or constructs comprising the polynucleotide inhibitors and to the production of siRNA polynucleotides, polypeptides, and/or fusion proteins, or fragments or variants thereof, by recombinant techniques. siRNA sequences disclosed herein as RNA polynucleotides may be engineered to produce corresponding DNA sequences using well-established methodologies such as those described herein. Thus, for example, a DNA polynucleotide may be generated from any siRNA sequence described herein, such that the present siRNA sequences will be recognized as also providing corresponding DNA polynucleotides (and their complements).

A vector may comprise a recombinant nucleic acid construct containing one or more promoters for transcription of an RNA molecule, for example, the human U6 snRNA promoter (see, e.g., Miyagishi et al., *Nat. Biotechnol.* 20:497-500 (2002); Lee et al., *Nat. Biotechnol.* 20:500-505 (2002); Paul et al., *Nat. Biotechnol.* 20:505-508 (2002); Grabarek et al., *BioTechniques* 34:73544 (2003); see also Sui et al., *Proc. Natl. Acad. Sci.* USA 99:5515-20 (2002)). Each strand of a siRNA polynucleotide may be transcribed separately each under the direction of a separate promoter and then may hybridize within the cell to form the siRNA polynucleotide duplex. Each strand may also be transcribed from separate vectors (see Lee et al., supra). Alternatively, the sense and antisense sequences specific for a CDH17 mRNA sequence may be transcribed under the control of a single promoter such that the siRNA polynucleotide forms a hairpin molecule (Paul et al., supra). In such instance, the complementary strands of the siRNA specific sequences are separated by a spacer that comprises at least four nucleotides, but may comprise at least 5, 6, 7, 8, 9, 10, 11, 12, 14, 16, or 18 or more nucleotides as described herein. In addition, siRNAs transcribed under the control of a U6 promoter that form a hairpin may have a stretch of about four uridines at the 3' end that act as the transcription termination signal (Miyagishi et al., supra; Paul et al., supra). By way of illustration, if the target sequence is 19 nucleotides, the siRNA hairpin polynucleotide (beginning at the 5' end) has a 19-nucleotide sense sequence followed by a spacer (which as two uridine nucleotides adjacent to the 3' end of the 19-nucleotide sense sequence), and the spacer is linked to a 19 nucleotide antisense sequence followed by a 4-uridine terminator sequence, which results in an overhang. siRNA polynucleotides with such overhangs effectively interfere with expression of the target polypeptide. A recombinant construct may also be prepared using another RNA polymerase III promoter, the H1 RNA promoter, that may be operatively linked to siRNA polynucleotide specific sequences, which may be used for transcription of hairpin structures comprising the siRNA specific sequences or separate transcription of each strand of a siRNA duplex polynucleotide (see, e.g., Brummelkamp et al., *Science* 296:550-53 (2002); Paddison et al., supra). DNA vectors useful for insertion of sequences for transcription of an siRNA polynucleotide include pSUPER vector (see, e.g., Brummelkamp et al., supra); pAV vectors derived from pCWRSVN (see, e.g., Paul et al., supra); and pIND (see, e.g., Lee et al., supra), or the like.

The appropriate DNA sequence(s) may be inserted into the vector by a variety of procedures. In general, the DNA sequence is inserted into an appropriate restriction endonuclease site(s) by procedures known in the art. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described, for example, in Ausubel et al. (1993 Current Protocols in Molecular Biology, Greene Publ. Assoc. Inc. & John Wiley & Sons, Inc., Boston, Mass.); Sambrook et al. (2001 Molecular Cloning, Third Ed., Cold Spring Harbor Laboratory, Plainview, N.Y.); Maniatis et al. (1982 Molecular Cloning, Cold Spring Harbor Laboratory, Plainview, N.Y.); and elsewhere.

The DNA sequence in the expression vector is operatively linked to at least one appropriate expression control sequence (e.g., a promoter or a regulated promoter) to direct mRNA synthesis. Representative examples of such expression control sequences include LTR or SV40 promoter, the *E. coli* lac or trp, the phage lambda $P_L$ promoter and other promoters known to control expression of genes in prokaryotic or eukaryotic cells or their viruses. Promoter regions can be selected from any desired gene using CAT (chloramphenicol transferase) vectors or other vectors with selectable markers. Examples of Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art, and preparation of certain particularly preferred recombinant expression constructs comprising at least one promoter or regulated promoter operably linked to a polynucleotide of the invention is described herein.

In certain embodiments the vector may be a viral vector such as a mammalian viral vector (e.g., retrovirus, adenovirus, adeno-associated virus, lentivirus). For example, retroviruses from which the retroviral plasmid vectors may be derived include, but are not limited to, Moloney Murine Leukemia Virus, spleen necrosis virus, retroviruses such as Rous Sarcoma Virus, Harvey Sarcoma virus, avian leukosis virus, gibbon ape leukemia virus, human immunodeficiency virus, adenovirus, Myeloproliferative Sarcoma Virus, and mammary tumor virus.

The viral vector includes one or more promoters. Suitable promoters which may be employed include, but are not limited to, the retroviral LTR; the SV40 promoter; and the human cytomegalovirus (CMV) promoter described in Miller, et al., *Biotechniques* 7:980-990 (1989), or any other promoter (e.g., cellular promoters such as eukaryotic cellular promoters including, but not limited to, the histone, pol III, and beta-actin promoters). Other viral promoters that may be employed include, but are not limited to, adenovirus promoters, adeno-associated virus promoters, thymidine kinase (TK) promoters, and B19 parvovirus promoters. The selection of a suitable promoter will be apparent to those skilled in the art from the teachings contained herein, and may be from among either regulated promoters (e.g., tissue-specific or inducible promoters) or promoters as described above). A tissue-specific promoter allows preferential expression of the polynucleotide CDH17 inhibitor in a given target tissue, thereby avoiding expression in other tissues. Liver-specific promoters include the human phenylalanine hydroxylase (PAH) gene promoters (Bristeau et al., *Gene* 274:283-291, 2001), hB1F (Zhang et al., *Gene* 273:239-249, 2001), and the human C-reactive protein (CRP) gene promoter (Ruther et al., *Oncogene* 8:87-93, 1993).

(vi) Host Cells

Also provided are host cells containing the above described recombinant constructs. Polynucleotide CDH17 inhibitors can be expressed in mammalian cells, yeast, bacteria, or other cells under the control of appropriate promoters, providing ready systems for evaluation of siRNA polynucleotides that are capable of interfering with CDH17 expression as provided herein. Appropriate cloning and expression vectors for use with prokaryotic and eukaryotic hosts are described, for example, by Sambrook, et al., Molecular Cloning: A Laboratory Manual, Third Edition, Cold Spring Harbor Laboratory Press, N.Y., (2001).

Host cells are genetically engineered/modified (transduced, transformed or transfected) with the disclosed vectors and/or expression constructs for example, a cloning vector, a shuttle vector, or an expression construct. The vector or construct may be, for example, in the form of a plasmid, a viral particle, a phage, etc. The engineered host cells can be cultured in conventional nutrient media modified as appropriate for activating promoters, selecting transformants or amplifying particular genes such as genes encoding siRNA polynucleotides or fusion proteins thereof. The culture conditions for particular host cells selected for expression, such as temperature, pH and the like, will be readily apparent to the ordinarily skilled artisan.

The host cell can be a higher eukaryotic cell, such as a mammalian cell, or a lower eukaryotic cell, such as a yeast cell, or the host cell can be a prokaryotic cell, such as a bacterial cell. Representative examples of appropriate host cells but need not be limited to, bacterial cells, such as *E. coli, Streptomyces, Salmonella typhimurium*; fungal cells, such as yeast; insect cells, such as Drosophila S2 and Spodoptera Sf9; animal cells, such as CHO, COS or 293 cells; adenoviruses; plant cells, or any suitable cell already adapted to in vitro propagation or so established de novo.

Various mammalian cell culture systems can also be employed to produce polynucleotide CDH17 inhibitors from recombinant nucleic acid constructs disclosed herein. Thus, a method of producing a polynucleotide, such as an siRNA, by culturing a host cell comprising a recombinant nucleic acid construct that comprises at least one promoter operably linked to a polynucleotide CDH17 inhibitor is additionally provided. In certain embodiments, the promoter may be a regulated promoter as provided herein, for example a tetracycline-repressible promoter. In certain embodiments the recombinant expression construct is a recombinant viral expression construct as provided herein. Examples of mammalian expression systems include the COS-7 lines of monkey kidney fibroblasts, described by Gluzman, Cell 23:175 (1981), and other cell lines capable of expressing a compatible vector, for example, the C127, 3T3, CHO, HeLa, HEK, and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences, for example as described herein regarding the preparation of recombinant polynucleotide constructs. DNA sequences derived from the SV40 splice, and polyadenylation sites may be used to provide the required nontranscribed genetic elements. Introduction of the construct into the host cell can be effected by a variety of methods with which those skilled in the art will be familiar, including but not limited to, for example, liposomes including cationic liposomes, calcium phosphate transfection, DEAE-Dextran mediated transfection, or electroporation (Davis et al., 1986 Basic Methods in Molecular Biology), or other suitable technique.

The expressed polynucleotides may be useful in intact host cells; in intact organelles such as cell membranes, intracellular vesicles or other cellular organelles; or in disrupted cell preparations including but not limited to cell homogenates or lysates, microsomes, uni- and multilamellar membrane vesicles or other preparations. Alternatively, expressed polynucleotides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Finally, high performance liquid chromatography (HPLC) can be employed for final purification steps.

In general, the target nucleic acid is DNA or RNA. However, the disclosed methods may employ, for example, samples that contain DNA, or DNA and RNA, including messenger RNA, wherein DNA or RNA may be single stranded or double stranded, or a DNA-RNA hybrid may be included in the sample. A mixture of nucleic acids may also be employed. The specific nucleic acid sequence to be detected may be a fraction of a larger molecule or can be present initially as a discrete molecule, so that the specific sequence constitutes the entire nucleic acid. It is not necessary that the sequence to be studied be present initially in a pure form; the nucleic acid may be a minor fraction of a complex mixture, such as contained in whole human DNA. The nucleic acid-containing sample used for determination of the sensitivity of the target cells to radiation therapy may be extracted by a variety of techniques such as that described by Sambrook, et al. (Molecular Cloning: A Laboratory Manual, Cold Spring Harbor, N.Y., 1989; incorporated in its entirety herein by reference).

Cells expressing the target nucleic acid isolated from a subject can be obtained in a biological specimen from the subject. The cells, or nucleic acid, can be isolated from tumor tissue, blood, plasma, serum, lymph, lymph nodes, spleen, bone marrow, or any other biological specimen containing the target nucleic acid. Tumor tissue, blood, plasma, serum, lymph, spleen, and bone marrow are obtained by various medical procedures known to those of skill in the art.

(B) CDH17 Antibodies

In a preferred embodiment, an antibody used in the disclosed methods is CDH17 in a biological sample is a monoclonal antibody. More preferably, a monoclonal antibody for the region spanning domains 1 and 2 (D1-D2) of CDH17 is provided; this focuses the detection of CDH17 to the form of the protein readily secreted into the serum of patients having HCC.

A monoclonal antibody composition is typically composed of antibodies produced by clones of a single cell called a hybridoma that secretes (produces) only one type of antibody molecule. The hybridoma cell is formed by fusing an antibody-producing cell and a myeloma or other self-perpetuating cell line. Such antibodies were first described by Kohler and Milstein, Nature, 1975, 256:495-497, the disclosure of which is herein incorporated by reference. An exemplary hybridoma technology is described by Niman et al., Proc. Natl. Acad. Sci. U.S.A., 1983, 80:4949-4953. Other methods of producing monoclonal antibodies, a hybridoma cell, or a hybridoma cell culture are also well known. See e.g., Antibodies: A Laboratory Manual, Harlow et al., Cold Spring Harbor Laboratory, 1988; or the method of isolating monoclonal antibodies from an immunological repertoise as described by Sasatry, et al., Proc. Natl. Acad. Sci. USA, 1989, 86:5728-5732; and Huse et al., Science, 1981, 246:1275-1281. The references cited are hereby incorporated herein by reference.

In order to produce monoclonal antibodies, a host mammal is inoculated with a CDH17 protein or peptide and then boosted. Spleens are collected from inoculated mammals a few days after the final boost. Cell suspensions from the spleens are fused with a tumor cell in accordance with the general method described by Kohler and Milstein (Nature, 1975, 256:495-497). In order to be useful, a peptide fragment must contain sufficient amino acid residues to define the epitope of the CDH17 molecule being detected.

If the fragment is too short to be immunogenic, it may be conjugated to a carrier molecule. Some suitable carrier molecules include keyhole limpet hemocyanin and bovine serum albumin. Conjugation may be carried out by methods known in the art. One such method is to combine a cysteine residue of the fragment with a cysteine residue on the carrier molecule. The peptide fragments may be synthesized by methods known in the art. Some suitable methods are described by Stuart and Young in "Solid Phase Peptide Synthesis," Second Edition, Pierce Chemical Company (1984).

Other antibodies specific for CDH17 that are useful in the disclosed methods may be obtained from scientific or commercial sources. Alternatively, isolated native CDH17 or recombinant CDH17 may be utilized to prepare antibodies, monoclonal or polyclonal antibodies, and immunologically active fragments (e.g., a Fab or (Fab)$_2$ fragment), an antibody heavy chain, an antibody light chain, humanized antibodies, a genetically engineered single chain F$_v$ molecule (Ladne et al., U.S. Pat. No. 4,946,778), or a chimeric antibody, for example, an antibody which contains the binding specificity of a murine antibody, but in which the remaining portions are of human origin. Antibodies including monoclonal and polyclonal antibodies, fragments and chimeras, may be prepared using methods known to those skilled in the art. Preferably, antibodies used in the disclosed methods are reactive against CDH17 if they bind with a $K_a$ of greater than or equal to $10^7$ M. In a sandwich immunoassay mouse polyclonal antibodies and rabbit polyclonal antibodies are utilized.

Preferred binding epitopes may be identified from a known CDH17 gene sequence and its encoded amino acid sequence and used to generate CDH17 antibodies with high binding affinity. Also, identification of binding epitopes on CDH17 can be used in the design and construction of preferred antibodies. For example, a DNA encoding a preferred epitope on CDH17 may be recombinantly expressed and used to select an antibody which binds selectively to that epitope. The selected antibodies then are exposed to the sample under conditions sufficient to allow specific binding of the antibody to the specific binding epitope on CDH17 and the amount of complex formed then detected. Specific antibody methodologies are well understood and described in the literature. A more detailed description of their preparation can be found, for example, in Practical Immunology, Butt, W. R., ed., Marcel Dekker, New York, 1984.

Purification of the antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (Goding in, Monoclonal Antibodies: Principles and Practice, 2d ed., pp. 104-126, Orlando, Fla., Academic Press). It is preferable to use purified antibodies or purified fragments of the antibodies having at least a portion of a CDH17 binding region, including such as Fv, $F(ab')_2$, Fab fragments (Harlow and Lane, 1988, Antibody, Cold Spring Harbor Laboratory Press) for the detection of CDH17 in the fluids of liver cancer patients or those at risk, preferably in the urine or blood of liver cancer patients.

A panel of characterized monoclonal antibodies which recognize different epitopes of CDH17 has been developed. These antibodies can be used to differentiate liver tumors selectively in diagnostic assays. Monoclonal antibodies that recognize the unique truncated CDH17 (spanning domains 1 and 2 (D1-D2)) molecule secreted into the serum of HCC patients serve as a superior diagnostic reagent for HCC. Application of both the CDH17 molecule and its specific monoclonal antibodies leads to treatment of liver cancers. Monoclonal antibodies specific for CDH17 can be used in screening assays to detect the presence of this molecule in both liver tumor tissues and serum of HCC patients. The anti-CDH17 antibodies are preferably directed to the serum-secretion-specific D1-D2 epitope of the CDH17 molecule. These monoclonal antibodies can also be used as vehicles to deliver cargos, such as nucleic acid, drug or toxin, to liver tumor cells with high expression of CDH17 on cell surface or simply as CDH17 antagonists to inhibit CDH17 activity in the tumor cell. In addition, hybridoma cell lines provide unlimited source for producing monoclonal antibodies when needed. Culturing the hybridoma cells can produce large quantities of the antibodies economically. Thus, cost effective methods using monoclonal antibodies for detection/monitoring the presence of CDH17 in biological samples are provided.

III. Pharmaceutical Compositions

CDH17 inhibitors (also referred to herein as "active compounds") can be incorporated into pharmaceutical compositions suitable for administration. Such compositions typically comprise a pharmaceutically effective amount of a CDH17-inhibiting nucleic acid molecule, protein, or antibody and a pharmaceutically acceptable carrier. The term "therapeutically effective amount" as used herein, means that amount of CDH17 inhibitor alone or in combination with another agent that elicits the biological or medicinal response in cells (e.g., tissue(s)) that is being sought by a researcher, veterinarian, medical doctor or other clinician, which includes alleviation and/or prevention of the symptoms of the disease or disorder being treated. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In one embodiment, the polynucleotide CDH17 inhibitors are prepared with carriers that will protect against rapid elimination from, or degradation in, the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions (including liposomes targeted to antigen-presenting cells with monoclonal antibodies) can also be used as pharmaceutically acceptable carriers. These can be prepared according to methods known to those skilled in the art, for example, as described in U.S. Pat. No. 4,522,811. Strategies that inhibit members of the RNAse A family of enzymes or can otherwise protect polynucleotide CDH17 inhibitors from these enzymes may be utilized as described for example in U.S. Pat. No. 6,096,720 (Love et al.). A strategy for the compaction of short oligonucleotides into well-defined condensates may also be used to deliver the CDH17 inhibitory polynucleotides disclosed herein (Sarkar T. et al., *Nucleic Acids Research,* 2005, 33(1): 143-151), which is incorporated herein by reference in its entirety.

In another embodiment, the polynucleotide CDH17 inhibitors can be inserted into genetic constructs, e.g., viral vectors, retroviral vectors, expression cassettes, or plasmid viral vectors, e.g., using methods known in the art, including but not limited to those described in Xia et al., (2002), supra. Genetic constructs can be delivered to a subject by, for example, inhalation, orally, intravenous injection, local administration (see U.S. Pat. No. 5,328,470) or by stereotactic injection (see, e.g., Chen et al., *Proc. Natl. Acad. Sci.* USA 91:3054-3057 (1994)). The pharmaceutical preparation of the delivery vector can include the vector in an acceptable diluent, or can comprise a slow release matrix in which the delivery vehicle is imbedded. Alternatively, where the complete delivery vector can be produced intact from recombinant cells, e.g., retroviral vectors, the pharmaceutical preparation can include one or more cells which produce the polynucleotide delivery system.

(i) Injectable Compositions

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

(ii) Oral Compositions

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. These are not typically used for administration of polynucleotides or antibodies.

(iii) Compositions for Pulmonary Administration

For administration by inhalation, the compounds are delivered in the form of an aerosol spray from pressured container or dispenser which contains a suitable propellant, e.g., a gas such as carbon dioxide, or a nebulizer.

(iv) Compositions for Topical Administration

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

(v) Parenteral Administration

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

A method for preparing a medicament or pharmaceutical composition comprising the therapeutic agents of the invention, the pharmaceutical composition being used for therapy of hepatocellular carcinoma is also provided.

The compounds can also be prepared in the form of suppositories (e.g., with conventional suppository bases such as cocoa butter and other glycerides) or retention enemas for rectal delivery.

It is especially advantageous to formulate of compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

IV. Therapeutic Methods of Use (A) Method of Treatment/Sensitization: Suppression of Knockdown of CDH17 Expression Methods of treatment include prophylactic and therapeutic methods of treating a subject at risk of (or susceptible to) a disorder or having a disorder associated with aberrant target gene expression or activity. Alternatively, the target gene expression or activity may be normal (non-aberrant) but a decrease in target gene expression or activity would nonetheless have a beneficial effect on the subject. Such disorders include various liver cancers.

Methods of treatment also include sensitizing cells exhibiting aberrant CDH17 expression to chemotherapeutic agents, by co-administering the disclosed CDH17 inhibitors.

In one aspect, the subject is administered an agent which modulates or inhibits the target gene (CDH17) expression. Subjects at risk for a condition which is caused or contributed to by aberrant target gene expression or overexpression, such as liver cancer, can be identified by, for example, any or a combination of diagnostic or prognostic assays as is known in the art and described herein.

In a preferred embodiment, the agent inhibits one or more of the biological activities of the target gene protein. Examples of such inhibitory agents include antisense target gene nucleic acid molecules and anti-target gene antibodies. These modulatory methods can be performed in vitro (e.g., by culturing the cell with the agent) or, alternatively, in vivo (e.g., by administering the agent to a subject). As such, methods of treating an individual afflicted with a disease or disorder characterized by aberrant expression or activity of the target gene protein or nucleic acid molecule are provided. In one embodiment, the method involves administering an agent, or combination of agents that modulates (e.g., upregulates or downregulates) the target gene expression or activity. In another embodiment, the method involves administering the target gene protein or nucleic acid molecule as therapy to compensate for reduced or aberrant target gene expression or activity.

For example, in one embodiment, the method involves administering a desired drug to an individual with a cell population expressing relatively high target gene levels, and coadministering an inhibitor of the target gene expression or activity. The administration and coadministration steps can be carried out concurrently or in any order, and can be separated by a time interval sufficient to allow uptake of either compound by the cells to be eradicated. For example, an antisense pharmaceutical composition (or a cocktail composition comprising an the target gene antisense oligonucleotide in combination with one or more other antisense oligonucleotides) can be administered to the individual sufficiently in advance of administration of the drug to allow the antisense composition to permeate the individual's tissues, especially tissue comprising the transformed cells to be eradicated; to be internalized by transformed cells; and to disrupt the target gene expression and/or protein production.

Inhibition of the target gene activity is desirable in situations in which the target gene is abnormally upregulated, e.g., in HCC.

The dosage ranges for the administration of the therapeutic agents as disclosed herein are those large enough to produce the desired effect in which the symptoms of HCC are treated. The dosage should not be so large as to cause adverse side effects, such as unwanted cross-reactions, anaphylactic reactions, and the like. Generally, the dosage will vary with the age, condition, sex and extent of the symptoms in the patient and can be determined by one of skill in the art. The dosage can be adjusted by the individual physician in the event of any counterindications. The dosage amount may depend on the specific HCC which is treated and can be readily determined using known dosage adjustment techniques by a physician having ordinary skill in treatment of these disorders. The dosage amount will generally lie within an established therapeutic window for the therapeutic compound which will provide a therapeutic effect while minimizing additional morbidity and mortality. Typically, therapeutic compounds will be administered in a dosage ranging from 0.001 mg/kg to about 100 mg/kg per dose, preferably 0.1-20 mg/kg. The preferred dose of about 0.5-5 mg/kg is particularly useful for compounds containing the therapeutic agents disclosed herein, in one or more dose administrations daily, for one or several days.

In a preferred embodiment, the CDH17 molecule is used as a target for molecular therapy. For this, several approaches, such as the application of small interfering RNA (siRNA) as CDH17 antagonists targeting the CDH17 transcript, can be used to inhibit or downregulate the expression of CDH17 in liver tumor cells. In addition, suppression of the expression of CDH17 can render liver tumor cells more sensitive to current therapeutic drugs or gene therapy, improving the efficacy of the treatments.

In one embodiment of the treatment method, exon 3 of CDH17 can be targeted to silence the expression of CDH17 to inhibit the progression of liver cancer and sensitize the liver tumor cells to therapeutic drugs or gene therapy, thus improving the efficacy of these treatments.

In another embodiment of the treatment method, exon 5 of CDH17 can be targeted to silence the expression of CDH17 to inhibit the progression of liver cancer and sensitize the liver tumor cells to therapeutic drugs or gene therapy, thus improving the efficacy of these treatments.

In yet another embodiment of the treatment method, RNAi directed to the suppression of CDH17 expression is used for the therapeutic treatment of hepatocellular carcinoma.

By "inhibit", "downregulate", "knockdown" or "silence" it is meant that the expression of the gene, or level of RNAs or equivalent RNAs encoding CDH17, is reduced below that observed in the absence of the inhibitory nucleic acid molecules disclosed herein. In one embodiment, inhibition or downregulation with enzymatic nucleic acid molecule preferably is below that level observed in the presence of an enzymatically inactive or attenuated molecule that is able to bind to the same site on the target RNA, but is unable to cleave that RNA. In another embodiment, inhibition or downregulation with antisense oligonucleotides is preferably below that level observed in the presence of, for example, an oligonucleotide with scrambled sequence or with mismatches. In another embodiment, inhibition or downregulation of CDH17 with the disclosed inhibitory nucleic acid molecule is greater in the presence of the nucleic acid molecule than in its absence.

Suppression or knockdown of the expression by CDH17 antagonists/inhibitors has demonstrated a benefit in the treatment of liver cancers. Thus, suppression of CDH17 expression is useful for producing a clinical response to treatment of liver cancer, or HCC, or other cell proliferation disorders. The method comprises administering an effective amount of a CDH17 inhibitor to a subject in need thereof.

As used herein, an "effective amount" of a CDH17 inhibitor (such as an interfering RNA, an antisense oligonucleotide, or a ribozyme, which selectively interferes with expression of CDH17) is that amount effective to bring about the physiological changes desired in the cells to which the CDH17 inhibitor is administered in vitro (e.g., ex vivo) or in vivo. Preferably, suppression of CDH17 function (e.g., by reduction of CDH17 expression) results in tumor shrinkage or increased sensitivity to chemotherapy.

Reduction (suppression) of expression results in a decrease of CDH17 mRNA and/or protein. For example, in a given cell, the suppression of CDH17 mRNA by administration of a CDH17 inhibitor that reduces CDH17 function by reducing CDH17 expression (such as interfering RNA, antisense oligonucleotide, or ribozyme) results in a decrease in the quantity of CDH17 mRNA relative to an untreated cell. Suppression may be partial. Preferred degrees of suppression are at least 50%, more preferably one of at least 60%, 70%, 80%, 85%, or 90%. A level of suppression between 90% and 100% is generally considered a "silencing" of expression.

CDH17 gene expression can be determined before and/or after introduction of the CDH17 inhibitor in vitro or in vivo. Reduction in CDH17 gene expression can be detected at either the protein or mRNA level. Protein expression analysis can be performed by Western blotting, immunofluorescence, or flow cytometry and cell sorting (FACS). Reduction in CDH17 gene expression can be detected at the mRNA level by real-time RT-PCR, microarray analysis, or Northern blotting, for example. Preferably, all expression data is compared with levels of a "house keeping" gene to normalize for variable amounts of RNA in different samples.

In a further embodiment of the method of treatment, an anti-CDH17, or CDH17 antagonist, antibody is used to inhibit the symptoms of a cancer overexpressing CDH17. The CDH17 antagonist for use in treatment inhibits the activity of the overexpressed CDH17 protein.

In this embodiment, the anti-CDH17 antibody is preferably directed to an epitope spanning domains 1 and 2 (D1-D2) of CDH17, having the sequence: PLKPMTFSIYEGQEPS-QIIFQFKANPPAVTFELTGETDNIFVIEREGLLYYNR ALDRETRSTHNLQVAALDANGIIVEG-PVPITIKVKDINDNRPTFLQSKYEGS VRQNSRPGKP-FLYVNATDLDDPATPNGQLYYQIVIQLP-MINNVMYFQINN KTGAISLTREGSQELNPAKNPSYNLVISVKD MGGQSENSFSDTTSVDIIVTE NIWKAPKP (SEQ ID NO: 1).

Creation of the D1-D2 anti-CDH17 antibody permits the targeted inhibition of the overexpressed form of CDH17 occurring in HCC.

In other embodiments, the CDH17 inhibitors are polynucleotides (referred to herein as "polynucleotide CDH17 inhibitors" or "nucleic acid CDH17 inhibitors") such as the antisense, interfering RNA molecules, and ribozymes. The target of the polynucleotide CDH17 inhibitors may be any portion of the CDH17 gene or CDH17 mRNA.

The CDH17 inhibitor can be administered alone or in combination with other pharmaceutical agents. The suppression or knockdown of CDH17 presents as a reduction in size of liver tumors derived from tumor cells that exhibit an increased expression of CDH17 and renders liver tumor cells more sensitive to certain chemotherapeutic drugs, such as Taxol, Epirubicin, and Carboplatin, and p53-based gene therapy.

In one embodiment, the interfering RNA that is capable, when suitably introduced or expressed within a cell that normally expresses CDH17 mRNA, suppresses its expression by RNAi, wherein the interfering RNA is generally targeted to the CDH17 D1-D2 domains, within the human CDH17 cDNA, Preferably, the interfering RNA sequence is within the range of about 19 to 23 nucleotides. For example, in those embodiments in which an shRNA is utilized, that portion of the shRNA targeting CDH17 is preferably within the range of about 19 to 23 nucleotides. A preferred shRNA targeted sequence of CDH17 in Exon 3 is CAAGAACCGAGT-CAAATTA (SEQ ID NO: 5) or in Exon 5: CAGTCCCTAT-CACCATAGAA (SEQ ID NO: 6).

Perfect identity/complementarity between the interfering RNA used in the disclosed method and the target sequence, although preferred, is not essential. Accordingly, the interfering RNA may include a single mismatch compared to the target sequence within the CDH17 mRNA. It is expected, however, that the presence of even a single mismatch is likely to lead to reduced efficiency, so the absence of mismatches is preferred. When present, 3' overhangs may be excluded from the consideration of the number of mismatches. The term "complementarity" is not limited to conventional base pairing between nucleic acid consisting of naturally occurring ribo- and/or deoxyribonucleotides, but also includes base pairing between mRNA and inhibitory nucleic acids that include non-natural nucleotides.

In another embodiment, monoclonal antibodies specific for CDH17 can be used as a delivery vehicle for drug or toxin. Drug or toxin can be conjugated to the antibodies using a biochemical approach. Monoclonal antibodies specific for the amino-terminus of cadherin-17 can be used as a delivery vehicle for drug or toxin. This enables the transport of drug or toxin to tumor cells with high expression of CDH17.

The terms "treatment" and "therapy" are used interchangeably herein, and as used herein include both prophylactic and responsive treatment, can be either acute short-term or chronic long-term, and denote the inhibition or amelioration of hepatocellular carcinoma in a patient. "Patient" includes animals, including humans. The term "therapeutically effective" means that the amount of therapeutic agent (anti-CDH17 monoclonal antibody, CDH17-directed siRNA (described below)) used is of sufficient quantity to inhibit or ameliorate the symptoms of hepatocellular carcinoma.

siRNA Delivery for Longer-Term Expression

Synthetic siRNAs can be delivered into cells by methods known in the art, including cationic liposome transfection (LIPOFECTAMINE 2000 reagent, for example) and electroporation, for example. However, these exogenous siRNA generally show short term persistence of the silencing effect (4 to 5 days in cultured cells), which may be beneficial in certain embodiments. To obtain longer suppression of CDH17 expression and to facilitate delivery under certain circumstances, one or more siRNA duplexes, e.g., CDH17 ds siRNA, can be expressed within cells from recombinant DNA constructs (McIntyre, et al., *BMC Biotechnology*, 6:1-8 (2006)). Such methods for expressing siRNA duplexes within cells from recombinant DNA constructs to allow longer-term target gene suppression in cells are known in the art, including mammalian Pol III promoter systems (e.g., H1 or U6/snRNA promoter systems (Tuschl (2002), supra) capable of expressing functional double-stranded siRNAs. Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by an H1 or U6 snRNA promoter can be expressed in cells, and can inhibit target gene expression (Bagella, et al., *J. Cell. Physiol.*, 177:206-213 (1998); Lee, et al., (2002), supra; Miyagishi, et al., (2002), supra; Paul, et al., (2002), supra; Yu, et al., (2002), supra; Sui, et al., (2002), supra). Constructs containing siRNA sequence(s) under the control of a T7 promoter also make functional siRNAs when co-transfected into the cells with a vector expressing T7 RNA polymerase (Jacque (2002), supra). A single construct may contain multiple sequences coding for siRNAs, such as multiple regions of CDH17 mRNA, and can be driven, for example, by separate PolIII promoter sites.

Animal cells express a range of noncoding RNAs of approximately 22 nucleotides termed micro RNA (miRNAs)

which can regulate gene expression at the post transcriptional or translational level during animal development. One common feature of miRNAs is that they are all excised from an approximately 70 nucleotide precursor RNA stem-loop, probably by Dicer, an RNase III-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng (2002), supra). When expressed by DNA vectors containing polymerase III promoters, micro-RNA designed hairpins can silence gene expression (McManus (2002), supra).

Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Infection of HeLa cells by these recombinant adenoviruses allows for diminished endogenous target gene expression. Injection of the recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari et al., *Proc. Natl. Acad. Sci.* USA 99(22):14236-40 (2002)). In adult mice, efficient delivery of siRNA can be accomplished by the "high-pressure" delivery technique, a rapid injection (within 5 seconds) of a large volume of siRNA containing solution into animal via the tail vein (Liu (1999), supra; McCaffrey (2002), supra; Lewis, *Nature Genetics* 32:107-108 (2002)).

Nanoparticles, liposomes and other cationic lipid molecules can also be used to deliver siRNA into animals. It has been shown that siRNAs delivered systemically in a liposomal formulation can silence the disease target apolipoprotein B (ApoB) in non-human primates (Zimmermann, et al., *Nature*, 2006, 441:111-114). A gel-based agarose/liposome/siRNA formulation is also available (Jiamg, et al., *Oligonucleotides*, 14(4):239-48 (2004)).

Engineered RNA precursors, introduced into cells or whole organisms as described herein, will lead to the production of a desired siRNA molecule. Such an siRNA molecule will then associate with endogenous protein components of the RNAi pathway to bind to and target a specific mRNA sequence for cleavage and destruction. In this fashion, the CDH17 mRNA to be targeted by the siRNA generated from the engineered RNA precursor will be depleted from the cell or organism, leading to a decrease in the concentration of any translational product encoded by that mRNA in the cell or organism. The RNA precursors are typically nucleic acid molecules that individually encode either one strand of a dsRNA or encode the entire nucleotide sequence of an RNA hairpin loop structure.

Antisense nucleic acid molecules are typically administered to a subject (e.g., systemically or locally by direct injection at a tissue site), or generated in situ such that they hybridize with or bind to cellular mRNA and/or genomic DNA encoding the CDH17 to thereby inhibit expression of the CDH17 gene. Alternatively, antisense nucleic acid molecules can be modified to target selected cells (such as megakaryocytes and/or megakaryocyte progenitors) and then administered systemically. For systemic administration, antisense molecules can be modified such that they specifically bind to receptors or antigens (such as CD9, CD41, CD61, actin, or FVIIIRAg) expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

The CDH17 inhibitors can also be administered by transfection or infection using methods known in the art, including but not limited to the methods described in McCaffrey et al., *Nature* 418(6893):38-39 (2002) (hydrodynamic transfection); Xia et al., *Nature Biotechnol.* 20(10):1006-10 (2002) (viral-mediated delivery); or Putnam, *Am. J. Health Syst. Pharm.* 53(2):151-160 (1996), erratum at *Am. J. Health Syst. Pharm.* 53(3):325 (1996).

Polynucleotide CDH17 inhibitors can also be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in Hamajima et al., *Clin. Immunol. Immunopathol.* 88(2):205-10 (1998). Liposomes (e.g., as described in U.S. Pat. No. 6,472,375) and microencapsulation can also be used. Biodegradable targetable microparticle delivery systems can also be used (e.g., as described in U.S. Pat. No. 6,471,996).

In particular, suitable techniques for cellular administration of the polynucleotide CDH17 inhibitors, in vitro or in vivo are reviewed for example in Borkhardt, *Cancer Cell*, 2:167-8; Hannon (2002); *Nature*, 418:244-51 (2002); McManus, et al., *Nat Rev Genet.*, 3:737-47 (2002); Scherr, et al., *Curr Med. Chem.*, 10:245-56 (2003); Shuey, et al. *Drug Discov Today*, 7:1040-6 (2002); Gilmore, et al., *J. Drug Target.*, 12(6):315-340 (2004); Dykxhoorn, et al., *Annu. Rev. Med.*, 2005, 56:401-423. Systemic delivery using liposomes is disclosed for example in Lewis, et al. *Nat Genet.*, 2002, 32:107-8; Paul, et al. *Nat Biotechnol.*, 2002, 20:505-8; Song, et al. *Nat Med.*, 2003, 9:347-51; Sorensen, et al. *J Mol Biol.*, 2003, 327:761-6.

Virus mediated transfer is disclosed for example in Abbas-Terki, et al. *Hum Gene Ther.*, 2002, 13:2197-201; Barton, et al. *Proc Natl Acad Sci USA*, 2002, 99:14943-5; Devroe, et al., *BMC Biotechnol.*, 2002, 2:15; Lori, F. et al. *Am J Pharmacogenomics*, 2002, 2:245-52; Matta, H. et al. *Cancer Biol Ther.*, 2003, 2:206-10; Qin, X. F. et al. *Proc Natl Acad Sci USA*, 2003, 100:183-8; Scherr, M. et al. *Cell Cycle*, 2003, 2:251-7; Shen, C. et al. *FEBS Lett.*, 2003, 539:111-4; Lee S. K. et al., *Blood*, 2005, 106(3):818-826, epub Apr. 14, 2005. peptide delivery is disclosed in Morris, et al. *Curr Opin Biotechnol.*, 2000, 11:461-6; Simeoni, F. et al. *Nucleic Acids Res.*, 2003, 31:2717-24. Song, et al., *Nat. Biotechnol.*, 23(6):709-717, (2005) describe antibody mediated in vivo delivery of siRNAs via cell-surface receptors, which can be used to target interfering RNA molecules to the cell-surface receptors on megakaryocytes and megakaryocyte progenitors. Nanoparticles or nanocapsule delivery is disclosed in U.S. Pat. Nos. 6,649,192B and 5,843,509B. Recent technologies that may be employed for selecting, delivering, and monitoring interfering RNA molecules include Raab, et al., *Biotechnol. Bioeng.*, 88:121-132 (2004); Huppi, et al. *Mol. Cell*, 2005, 17:1-10; Spagnou, et al. *Biochemistry*, 2004, 43:13348-13356; Muratovska, et al., *FEBS Lett.*, 2004, 558:63-68; Kumar, et al. *Genome Res.*, 2003, 13:2333-2340; Chen, A. A. et al. *Nucleic Acids Res.*, 2005, 33:e190; Dykxhoorn, D. M. et al. *Gene Ther.*, 2006, epub ahead of print; Rodriguez-Lebron, E. and Paulson, H. L. *Gene Ther.*, 2005, epub ahead of print; Pai, S. I. et al. *Gene Ther.*, 2005, epub ahead of print; Raoul, C. et al. *Gene Ther.*, 2005, epub ahead of print; Manfredsson, F. P. et al. *Gene Ther.*, 2005, epub ahead of print; Downward, J. *BMJ*, 2004, 328:1245-1248.

A mixture of CDH17 antagonists of the same type or different types, may be introduced into cells in vitro or in vivo. For example, a mixture or pool of polynucleotide CDH17 antagonists such as interfering RNA molecules (e.g., 2-4 interfering molecules or more) can be introduced into cells (Oleinikov, et al., *Nucleic Acids Research*, 2005, 33(10):e92 (2005). Preferably, the interfering RNA molecules target different regions of the CDH17 mRNA. Preferably, the interfering RNA molecules have been previously validated as individually functioning to reduce CDH17 expression. The individual interfering RNAs of the mixture can be chemically synthesized (Elbashir S. M. et al., *Genes Dev.*, 2001, 15:188-200) or introduced as short DNA templates containing RNA polymerase promoter, which are transcribed within the cells in vitro or in vivo (Yu J. Y. et al., *Proc. Natl. Acad. Sci. USA*, 99:6047-6052).

Toxicity and therapeutic efficacy of compositions can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio $LD_{50}/ED_{50}$. Compositions which exhibit high therapeutic indices can be used. While compositions that exhibit toxic side effects can be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compositions generally lies within a range of circulating concentrations that include the ED50 with little or no toxicity. The dosage can vary within this range depending upon the dosage form employed and the route of administration utilized. For any composition used in the methods disclosed herein, the therapeutically effective dose can be estimated initially from cell culture assays. A dose can be formulated in animal models to achieve a circulating plasma concentration range that includes the $IC_{50}$ (i.e., the concentration of the test composition which achieves a half-maximal inhibition of symptoms) as determined in cell culture. Such information can be used to more accurately determine useful doses in humans. Levels in plasma can be measured, for example, by high performance liquid chromatography.

The CDH17 inhibitor can be administered on any appropriate schedule, e.g., from one or more times per day to one or more times per week; including once every other day, for any number of days or weeks, e.g., 1 day, 2 days, 3 days, 4 days, 5 days, 6 days, 1 week, 10 days, 2 weeks, 3 weeks, 4 weeks, 5 weeks, 6 weeks, 7 weeks, 8 weeks, 2 months, 3 months, 6 months, or more, or any variation thereon. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a CDH17 inhibitor can include a single treatment or can include a series of treatments.

The polynucleotide CDH17 inhibitors can be introduced (administered) into cells (such as mammalian cells) in vitro or in vivo using known techniques, as those described herein, to suppress gene expression. Similarly, genetic constructs (e.g., transcription vectors) containing DNA may be introduced into cells in vitro or in vivo using known techniques, as described herein, for transient or stable expression of CDH17 inhibitory RNA, to suppress gene expression. When administered to the cells in vivo, the polynucleotide CDH17 inhibitors can be administered to a subject systemically (e.g., intravenously), for example, or administered locally at the site of the cells (such as the liver).

The cells in which the polynucleotide CDH17 inhibitors are introduced may be any cell, such as a megakaryocyte or megakaryocyte progenitor, containing CDH17 mRNA. The cells can be primary cells, cultured cells, cells of cell lines, etc. In one embodiment, the cells are from liver.

CDH17 expression can also be inhibited by targeting nucleotide sequences complementary to the regulatory region of the CDH17 gene to form triple helical structures that prevent expression of CDH17 in target cells. See generally, Helene, *Anticancer Drug Des.*, 6:569-84 (1991); Helene, *Ann. N.Y. Acad. Sci.*, 660:27-36 (1992); and Maher, *Bioassays* 14:807-15 (1992). The potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

Polynucleotide Inhibitor Targets

In some embodiments, the nucleic acid target is the CDH17 domain or the amino-terminal or D1-D2 domain. In other embodiments, the nucleic acid target is a translation initiation site, 3' untranslated region, or 5' untranslated region.). In a preferred embodiment, the polynucleotide CDH17 inhibitor targets an mRNA sequence shared by all known hematopoietic CDH17 isoforms in humans. Such target sequence can be readily determined by those skilled in the art due to the extensive amount of sequence overlap between the isoforms. More preferably, the sequences in Exon 3 (SEQ ID NO: 5) and Exon 5 (SEQ ID NO: 6) which were shown to have good specificity and knockdown potential (>50%) against the human CDH17 cDNA sequence are used as target sequences.

The nucleotide sequences of mouse CDH17 (PubMed accession number: NM_019753), rat CDH17 (PubMed accession number: NM_053977) and human CDH17 (PubMed accession number: NM_004063) have been publicly available for several years. Pair-wise alignment scoring of orthologues shows high levels of homology among CDH17 sequences of humans, mice, and rats. Each sequence has seven CDH17 domains (D1 to D7) in the ectodomains and the degree of nucleotide homology of these domains between human, mouse, and rat is between 77% and 93%. In addition, the homology of D1-D2 between human, mouse, and rat ranges from 84% to 92% (Table 2).

TABLE 2

Percentage homology of CDH17 domains between human, mouse and rat

| | Percentage homology (%) | | |
|---|---|---|---|
| | Human vs Mouse | Human vs Rat | Mouse vs Rat |
| D1 | 84 | 82 | 93 |
| D2 | 85 | 86 | 91 |
| D3 | 82 | 82 | 93 |
| D4 | 79 | 77 | 89 |
| D5 | 77 | 80 | 91 |
| D6 | 77 | 77 | 91 |
| D7 | 81 | 81 | 93 |
| D1-2 | 85 | 84 | 92 |

*alignment was performed using ClustalW2

The target CDH17 sequence can be within any orthologue of CDH17, such as sequences substantially identical to human, mouse, rat, or bovine, or a portion of any of the foregoing, including but not limited to GenBank Accession Numbers (NM_004063), (NM_019753), and (NM_053977), for human, mouse, and rat, respectively.

The term "orthologue" as used herein refers to a sequence which is substantially identical to a reference sequence. The term "substantially identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain or common functional activity. For example, amino acid or nucleotide sequences that contain a common structural domain having at least about 60%, or 65% identity, likely 75% identity, more likely 85%, 90%, 91%, 92%, 93%, 94%, 95%, 96%, 97%, 98% or 99% identity are defined herein as substantially identical.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 50%, at least 60%, at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. The percent identity between two amino acid sequences can be determined using the Needleman and Wunsch (*J. Mol. Biol.* 48:444-453 (1970)) algorithm, which has been incorporated into the GAP program in the GCG software package (available at the official Accelrys web site), using either a Blossum 62 matrix or a PAM250 matrix, and a gap weight of 16, 14, 12, 10, 8, 6, or 4 and a length weight of 1, 2, 3, 4, 5, or 6. The percent identity between two nucleotide sequences can also be determined using the GAP program in the GCG software package (available at the official Accelrys web site), using a NWSgapdna.CMP matrix and a gap weight of 40, 50, 60, 70, or 80 and a length weight of 1, 2, 3, 4, 5, or 6. One set of parameters are a Blossum 62 scoring matrix with a gap penalty of 12, a gap extend penalty of 4, and a frameshift gap penalty of 5.

The percent identity between two amino acid or nucleotide sequences can further be determined using the algorithm of E. Meyers and W. Miller (*CABIOS*, 4:11-17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other orthologs, e.g., family members or related sequences. Such searches can be performed using the NBLAST and XBLAST programs (version 2.0) of Altschul, et al. *J. Mol. Biol.* 215:403-10 (1990). BLAST nucleotide searches can be performed with the NBLAST program, score=100, word length=12, to obtain nucleotide sequences homologous to known CDH17 nucleic acid sequences. BLAST protein searches can be performed with the XBLAST program, score=50, word length=3, to obtain amino acid sequences homologous to known polypeptide products of the CDH17 gene. To obtain gapped alignments for comparison purposes, Gapped BLAST can be utilized as described in Altschul et al., *Nucleic Acids Res.* 25:3389-3402 (1997). When utilizing BLAST and Gapped BLAST programs, the default parameters of the respective programs (e.g., XBLAST and NBLAST) can be used (see the National Center for Biotechnology Information web site of the National Institutes of Health).

Orthologs can also be identified using any other routine method known in the art, such as screening a cDNA library, e.g., a human cDNA library, using a probe designed to identify sequences which are substantially identical to a reference sequence.

V. Methods for Monitoring, Diagnosing or Prognosing of Liver Cancer

Methods useful in predictive medicine, including diagnostic assays, prognostic assays, pharmacogenomics, and monitoring clinical trials are used for prognostic (predictive) purposes to thereby treat an individual prophylactically are disclosed. Accordingly, diagnostic assays for determining the target gene protein and/or nucleic acid expression as well as the target gene activity, in a biological sample (e.g., blood, serum, cells, tissue) to thereby determine whether an individual is afflicted with a disease or disorder, or is at risk of developing a disorder, associated with aberrant target gene expression or activity (e.g., altered drug resistance) are provided. Also provided are prognostic (or predictive) assays for determining whether an individual is at risk of developing a disorder associated with the target gene protein, nucleic acid expression or activity (e.g., altered drug resistance). For example, mutations in the target gene can be assayed in a biological sample. Such assays can be used for prognostic or predictive purpose to thereby prophylactically treat an individual prior to the onset of a disorder characterized by or associated with the target gene protein, nucleic acid expression or activity. For example, because HCC is associated with instances where the CDH17 is expressed at a higher level in cells than normal, expression of the CDH17 target gene can be used as an indicator of HCC.

Methods for assessing expression, especially undesirable expression, of a cellular target gene are used in diagnostic assays. Undesirable (e.g., excessive) expression may indicate the presence, persistence or reappearance of HCC. More generally, aberrant expression may indicate the occurrence of a deleterious or disease-associated phenotype contributed to by the target gene. An exemplary method for detecting the presence or absence of the target gene in a biological sample involves obtaining a biological sample (preferably from a body site implicated in a possible diagnosis of diseased or malignant tissue) from a test subject and contacting the biological sample with a compound or an agent capable of detecting the target gene protein or nucleic acid (e.g., mRNA, genomic DNA) that encodes the target gene protein such that the presence of the target gene is detected in the biological sample. The presence and/or relative abundance of the target gene indicates aberrant or undesirable expression of a cellular the target gene, and correlates with the occurrence in situ of HCC.

A preferred agent for detecting the target gene mRNA or genomic DNA is a labeled nucleic acid probe capable of hybridizing to the target gene mRNA or genomic DNA. The nucleic acid probe can be, for example, a full-length the target gene nucleic acid, or a portion thereof, such as an oligonucleotide of at least 15, 30, 50, 100, 250 or 500 nucleotides in length and sufficient to specifically hybridize under stringent conditions to the target gene mRNA or genomic DNA. Other suitable probes for use in the diagnostic assays are described herein.

A preferred agent for detecting the target gene protein is an antibody capable of binding to the target gene protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method disclosed herein can be used to detect the target gene mRNA, protein, or genomic DNA in a biological sample in vitro as well as in vivo. For example, in vitro techniques for detection of the target gene mRNA include Northern hybridizations and in situ hybridizations. In vitro techniques for detection of the target gene protein include enzyme linked immunosorbent assays (ELISAs), Western blots, immunoprecipitations and immunofluorescence. In vitro techniques for detection of the target gene genomic DNA include Southern hybridizations.

In one embodiment, the biological sample contains protein molecules from the test subject. Alternatively, the biological sample can contain mRNA molecules from the test subject or genomic DNA molecules from the test subject. A preferred biological sample is a human serum isolated by conventional means from a subject.

In another embodiment, the methods further involve obtaining a control biological sample from a control subject, contacting the control sample with a compound or agent capable of detecting the target gene protein, mRNA, or genomic DNA, such that the presence of the target gene protein, mRNA or genomic DNA is detected in the biological sample, and comparing the presence of the target gene protein, mRNA or genomic DNA in the control sample with the presence of the target gene protein, mRNA or genomic DNA in the test sample.

Methods for monitoring, diagnosing, or for the prognosis of cancer, such as liver cancer, in a subject involve detecting CDH17 in a biological sample from the subject. The methods may be used for the detection of either an over- or an underabundance of CDH17 relative to a non-disorder state or the presence of a modified (e.g., less than full length) CDH17 which correlates with a disorder state (e.g., liver cancer), or a progression toward a disorder state, using an agent which is capable of detecting CDH17. The methods may be used to evaluate the probability of the presence of malignant or pre-malignant cells. Such methods can be used to detect tumors, quantitate their growth, and assist in the diagnosis and prognosis of liver cancer. The methods can be used to detect the presence of cancer metastasis, as well as confirm the absence or removal of all tumor tissue following surgery, cancer chemotherapy, and/or radiation therapy. They can further be used to monitor cancer chemotherapy and tumor reappearance. The methods are particularly useful in the diagnosis of early stage liver cancer (e.g., when the subject is asymptomatic) and for the prognosis of liver cancer disease progression and mortality. As illustrated herein, increased levels of CDH17 detected in a sample (e.g., urine, serum, plasma, whole blood, ascites) compared to a standard (e.g., levels for normal or benign disorders) are indicative of advanced disease stage, serous histological type, suboptimal debulking, large residual tumor, and/or increased risk of disease progression and mortality.

In some embodiments, a subject with the relevant condition or disease (e.g., liver cancer) is identified or a patient at risk for the condition or disease is identified prior to administration of the CDH17 inhibitor. A patient may be someone who has not been diagnosed with the disease or condition (diagnosis, prognosis, and/or staging) or someone diagnosed with the disease or condition (diagnosis, prognosis, monitoring, and/or staging), including someone treated for the disease or condition (prognosis, staging, and/or monitoring). Alternatively, the person may not have been diagnosed with the disease or condition but suspected of having the disease or condition based either on patient history or family history, or the exhibition or observation of characteristic symptoms.

Agents that are capable of detecting CDH17 in the biological samples of subjects are those that interact or bind with the CDH17 polypeptide or the nucleic acid molecule encoding CDH17. Examples of such agents (also referred to herein as binding agents) include, but are not limited to, CDH17 antibodies or fragments thereof that bind CDH17, CDH17 binding partners, and nucleic acid molecules that hybridize to the nucleic acid molecules encoding CDH17 polypeptides. Preferably, the binding agent is labeled with a detectable substance (e.g., a detectable moiety). The binding agent may itself function as a label.

The disclosed methods can include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an siRNA as disclosed herein into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

In one embodiment, the method for detecting/diagnosing liver cancer in a subject comprises contacting the sample with an antibody specific for CDH17 which is directly or indirectly labeled with a detectable substance, and detecting the detectable substance.

The method steps involve (a) contacting a biological sample from a subject with an antibody specific for CDH17 which is directly or indirectly labeled with an enzyme; (b) adding a substrate for the enzyme wherein the substrate is selected so that the substrate, or a reaction product of the enzyme and substrate, forms fluorescent complexes; (c) quantitating CDH17 in the sample by measuring fluorescence of the fluorescent complexes; and (d) comparing the quantitated levels to that of a standard.

A preferred embodiment comprises the following steps:

(a) incubating a biological sample with a first antibody specific for CDH17 which is directly or indirectly labeled with a detectable substance, and a second antibody specific for CDH17 which is immobilized;

(b) separating the first antibody from the second antibody to provide a first antibody phase and a second antibody phase;

(c) detecting the detectable substance in the first or second antibody phase thereby quantitating CDH17 in the biological sample; and (d) comparing the quantitated CDH17 with a standard.

A standard may correspond to CDH17 levels obtained for samples from healthy control subjects, from subjects with benign disease (e.g., benign liver disease), subjects with early stage liver cancer, or from other samples of the subject. Increased levels of CDH17 as compared to the standard may be indicative of cancer, such as early or late stage liver cancer.

In some embodiments the method described herein is adapted for diagnosing and monitoring liver cancer by quantitating CDH17 in biological samples from a subject. Preferably, the amount of CDH17 quantitated in a sample from a subject being tested is compared to levels quantitated for another sample or an earlier sample from the subject, or levels quantitated for a control sample. Levels for control samples from healthy subjects may be established by prospective and/or retrospective statistical studies. Healthy subjects who have no clinically evident disease or abnormalities may be selected for statistical studies. Diagnosis may be made by a finding of statistically different levels of CDH17 compared to a control sample or previous levels quantitated for the same subject.

In another embodiment of the detection/diagnosing method, a sandwich enzyme-linked immunosorbent assay (ELISA) can be developed using monoclonal antibodies specific for CDH17. This assay can be used to detect the presence of CDH17 in suspect tissues or in the serum of patients. An ELISA developed for detection of CDH17 is simple to use. It has high degrees of specificity and sensitivity, low intra- and inter-assay coefficients of variation, and uses chemicals that pose a low risk to human health and are easily disposed of. Thus it has a low cost to benefit ratio. It is flexible in its sample handling and can be used to process either low or high numbers of samples. This embodiment meets a longfelt but unmet need for a method for detection of human serum CDH17 protein expression in a large number of samples at a low cost and with simplicity and accuracy.

A description of the ELISA technique is found in Chapter 22 of the 4$^{th}$ Edition of Basic and Clinical Immunology by D. P. Sites et al., 1982, published by Lange Medical Publications of Los Altos, Calif. and in U.S. Pat. Nos. 3,654,090; 3,850,752; and 4,016,043, the disclosures of which are herein incorporated by reference. ELISA is an assay that can be used to quantitate the amount of antigen, proteins, or other molecules of interest in a sample. In particular, ELISA can be carried out by attaching on a solid support (e.g., polyvinylchloride) an antibody specific for an antigen or protein of interest. Cell extract or other sample of interest such as urine or blood can be added for formation of an antibody-antigen complex, and the extra, unbound sample is washed away. An enzyme-linked antibody, specific for a different site on the antigen is added. The support is washed to remove the unbound enzyme-linked second antibody. The enzyme-linked antibody can include, but is not limited to, alkaline phosphatase. The enzyme on the second antibody can convert an added colorless substrate into a colored product or can convert a non-fluorescent substrate into a fluorescent product. The ELISA-based assay method provided herein can be conducted in a single chamber or on an array of chambers and can be adapted for automated processes.

The antibodies can be labeled with pairs of FRET dyes, bioluminescence resonance energy transfer (BRET) protein, fluorescent dye-quencher dye combinations, and beta gal complementation assays protein fragments. The antibodies may participate in FRET, BRET, and fluorescence quenching or beta-gal complementation to generate fluorescence, colorimetric or enhanced chemiluminescence (ECL) signals, for example. These methods are routinely employed in the detection of antigen-specific antibody responses, and are well described in general immunology text books such as Immunology by Ivan Roitt, Jonathan Brostoff and David Male (London: Mosby, c1998. 5th ed. and Immunobiology: Immune System in Health and Disease/Charles A. Janeway and Paul Travers. Oxford: Blackwell Sci. Pub., 1994), the contents of which are herein incorporated by reference.

The terms "sample" and "biological sample", refer to a material known to or suspected of expressing or containing CDH17, such as urine. The test sample can be used directly as obtained from the source or following a pretreatment to modify the character of the sample. The sample can be derived from any biological source, such as tissues or extracts, including cells (e.g., tumor cells) and physiological fluids, such as, for example, whole blood, plasma, serum, peritoneal fluid, ascites, and the like. The sample can be obtained from animals, preferably mammals, most preferably humans. The sample can be pretreated by any method and/or can be prepared in any convenient medium that does not interfere with the assay. The sample can be treated prior to use, such as preparing plasma from blood, diluting viscous fluids, applying one or more protease inhibitors to samples such as urine (e.g., 4-(2 aminoethyl)-benzene sulfonyl fluoride, EDTA, leupeptin, and/or pepstatin), and the like. Sample treatment can involve filtration, distillation, extraction, concentration, inactivation of interfering components, the addition of reagents, and the like.

The presence of CDH17 may be detected in a variety of biological samples, including tissues or extracts thereof. Preferably, CDH17 is detected in human serum or plasma.

Antibodies specifically reactive with CDH17, or derivatives, such as enzyme conjugates or labeled derivatives, may be used to detect CDH17 in various biological samples, for example they may be used in any known immunoassays which rely on the binding interaction between an antigenic determinant of a protein and the antibodies. Examples of such assays are radioimmunoassays, enzyme immunoassay (e.g., ELISA), immunofluorescence, immunoprecipitation, latex agglutination, hemagglutination, and histochemical tests.

An antibody specific for CDH17 can be labeled with a detectable substance and localized in biological samples based upon the presence of the detectable substance. Examples of detectable substances include, but are not limited to, the following radioisotopes (e.g., $^3H$, $^{14}C$, $^{35}S$, $^{125}I$, $^{131}I$), fluorescent labels (e.g., FITC rhodamine, lanthanide phosphors), luminescent labels such as luminol; enzymatic labels (e.g., horseradish peroxidase, beta-galactosidase, luciferase, alkalline phosphatase, acetylcholinestease), biotinyl groups (which can be detected by marked avidin, e.g., streptavidin containing a fluorescent marker or enzymatic activity that can be detected by optical or calorimetric methods), predetermined polypeptide epitopes recognized by a secondary reporter (e.g., leucine zipper pair sequences, binding sites for secondary antibodies, metal binding domains, epitope tags). Indirect methods may also be employed in which the primary antigen-antibody reaction is amplified by the introduction of a second antibody, having specificity for the antibody reactive against CDH17. By way of example, if the antibody having specificity against CDH17 is a rabbit IgG antibody, the second antibody may be goat anti-rabbit gamma-globulin labeled with a detectable substance as described herein.

Methods for conjugating or labeling the antibodies discussed above may be readily accomplished by one of ordinary skill in the art. (See, for example, Imman, Methods In Enzymology, Vol. 34, Affinity Techniques, Enzyme Purification: Part B, Jakoby and Wichek (eds.), Academic Press, New York, p. 30, 1974; and Wilchek and Bayer, *Anal. Biochem.* 171:1-32, (1988)).

Time-resolved fluorometry may be used to detect a signal. For example, the method described in Christopoulos T. K. and Diamandis E. P., *Anal. Chem.*, 1992:64:342-346 may be used with a conventional time-resolved fluorometer.

In one embodiment, a method is provided wherein a CDH17 antibody is labeled with an enzyme, a substrate for the enzyme is added wherein the substrate is selected so that the substrate, or a reaction product of the enzyme and substrate, forms fluorescent complexes with a lanthanide metal. A lanthanide metal is added and CDH17 is quantitated in the sample by measuring fluorescence of the fluorescent complexes. The antibodies specific for CDH17 may be directly or indirectly labeled with an enzyme. Enzymes are selected based on the ability of a substrate of the enzyme, or a reaction product of the enzyme and substrate, to complex with lanthanide metals such as europium and terbium. Examples of suitable enzymes include alkalline phosphatase and beta-galactosidase. Preferably, the enzyme is alkaline phosphatase. The CDH17 antibodies may also be indirectly labeled with an enzyme. For example, the antibodies may be conjugated to one partner of a ligand binding pair, and the enzyme may be coupled to the other partner of the ligand binding pair. Representative examples include avidin-biotin, and riboflavin-riboflavin binding protein. Preferably the antibodies are biotinylated, and the enzyme is coupled to streptavidin.

The substrate is selected so that in the presence of a lanthanide metal (e.g., europium, terbium, samarium, and dysprosium, preferably europium and terbium), the substrate or a reaction product of the enzyme and substrate, forms a fluorescent complex with the lanthanide metal. Examples of enzymes and substrates for enzymes that provide such fluorescent complexes are described in U.S. Pat. No. 5,3112,922 to Diamandis. Exemplary substrates for an enzyme labeled with alkalline phosphatase is 4-methylumbeliferyl phosphate, or 5-fluorpsalicyl phosphate. The fluorescence intensity of the complexes is typically measured using a time-resolved fluorometer, e.g., a CyberFluor 615 Immoanalyzer (Nordion International, Kanata Ontario).

The sample, antibody specific for CDH17, or CDH17, may be immobilized on a carrier. Examples of suitable carriers are agarose, cellulose, dextran, Sephadex, Sepharose, liposomes, carboxymethyl cellulose polystyrene, filter paper, ion-exchange resin, plastic film, plastic tube, glass beads, polyamine-methyl vinyl ether-maleic acid copolymer, amino acid copolymer, ethylene-maleic acid copolymer, nylon, silk, etc. The carrier may be in the shape of, for example, a tube, test plate, well, beads, disc, sphere, etc. The immobilized antibody may be prepared by reacting the material with a suitable insoluble carrier using known chemical or physical methods, for example, cyanogen bromide coupling.

In accordance with an embodiment, a method is provided for detecting CDH17 in an appropriate sample such as urine or blood, preferably serum or plasma, by measuring CDH17 by immunoassay. It will be evident to a skilled artisan that a variety of immunoassay methods can be used to measure CDH17. In general, a CDH17 immunoassay method may be competitive or noncompetitive. Competitive methods typically employ an immobilized or immobilizable antibody to CDH17 (anti-CDH17) and a labeled form of CDH17. Sample CDH17 and labeled CDH17 compete for binding to anti-CDH17. After separation of the resulting labeled CDH17 that has become bound to anti-CDH17 (bound fraction) from that which has remained unbound (unbound fraction), the amount of the label in either bound or unbound fraction is measured and may be correlated with the amount of CDH17 in the biological sample in any conventional manner, e.g., by comparison to a standard curve.

Preferably, a noncompetitive method is used for the determination of CDH17, with the most common method being the "sandwich" method. In this assay, two anti-CDH17 antibodies are employed. One of the anti-CDH17 antibodies is directly or indirectly labeled (also referred to as the "detection antibody") and the other is immobilized or immobilizable (also referred to as the "capture antibody"). The capture and detection antibodies can be contacted simultaneously or sequentially with the biological sample. Sequential methods can be accomplished by incubating the capture antibody with the sample, and adding the detection antibody at a predetermined time thereafter (sometimes referred to as the "forward" method); or the detection antibody can be incubated with the sample first and then the capture antibody added (sometimes referred to as the "reverse" method). After the necessary incubation(s) have occurred, to complete the assay, the capture antibody is separated from the liquid test mixture, and the label is measured in at least a portion of the separated capture antibody phase or the remainder of the liquid test mixture. Generally, it is measured in the capture antibody phase since it comprises CDH17 bound by ("sandwiched" between) the capture and detection antibodies.

In a typical two-site immunometric assay for CDH17, one or both of the capture and detection antibodies are polyclonal antibodies. The label used in the detection antibody can be selected from any of those known conventionally in the art. As with other embodiments of the protein detection assay, the label can be an enzyme or a chemiluminescent moiety, for example, or a radioactive isotope, a fluorophore, a detectable ligand (e.g., detectable by a secondary binding by a labeled binding partner for the ligand), and the like. Preferably, the antibody is labeled with an enzyme that is detected by adding a substrate that is selected so that a reaction product of the enzyme and substrate forms fluorescent complexes. The capture antibody is selected so that it provides a mode for being separated from the remainder of the test mixture. Accordingly, the capture antibody can be introduced to the assay in an already immobilized or insoluble form, or can be in an immobilizable form, that is, a form which enables immobilization to be accomplished subsequent to introduction of the capture antibody to the assay. An immobilized capture antibody can comprise an antibody covalently or noncovalently attached to a solid phase such as a magnetic particle, a latex particle, a microtiter multi-well plate, a bead, a cuvette, or other reaction vessel. An example of an immobilizable capture antibody is an antibody that has been chemically modified with a ligand moiety, e.g., a hapten, biotin, or the like, and that can be subsequently immobilized by contact with an immobilized form of a binding partner for the ligand, e.g., an antibody, avidin, or the like. In an embodiment, the capture antibody can be immobilized using a species specific antibody for the capture antibody that is bound to the solid phase.

In other embodiments a sandwich immunoassay method employs two antibodies reactive against CDH17, a second antibody having specificity against an antibody reactive against CDH17 labeled with an enzymatic label, and a fluorogenic substrate for the enzyme. In an embodiment, the enzyme is alkaline phosphatase (ALP) and the substrate is 5-fluorosalicyl phosphate. ALP cleaves phosphate out of the fluorogenic substrate, 5-fluorosalicyl phosphate, to produce 5-fluorosalicylic acid (FSA). 5-Fluorosalicylic acid can then form a highly fluorescent ternary complex of the form FSA-Tb(3+)-EDTA, which can be quantified by measuring the $Tb^{3+}$ fluorescence in a time-resolved mode. Fluorescence intensity is typically measured using a time-resolved fluorometry as described herein.

The above-described immunoassay methods and formats are intended to be exemplary and are not limiting since, in general, it will be understood that any immunoassay method or format can be used in the disclosed methods.

The protein detection methods, devices, and kits can utilize nanowire sensor technology (Zhen et al., *Nature Biotechnology*, 2005, 23(10):1294-1301; Lieber et al., *Anal. Chem.*, 2006, 78(13):4260-4269, which are incorporated herein by reference) or microcantilever technology (Lee et al., *Biosens. Bioelectron*, 2005, 20(10):2157-2162; Wee et al., *Biosens. Bioelectron.*, 2005, 20(10):1932-1938; Campbell and Mutharasan, *Biosens. Bioelectron.*, 2005, 21(3):462-473; Campbell and Mutharasan, *Biosens. Bioelectron.*, 2005, 21(4):597-607; Hwang et al., *Lab Chip*, 2004, 4(6):547-552; Mukhopadhyay et al., *Nano. Lett.*, 2005, 5(12):2835-2388, which are incorporated herein by reference) for detection of CDH17 in samples. In addition, Huang et al. describe a prostate specific antigen immunoassay on a commercially available surface plasmon resonance biosensor (*Biosens. Bioelectron.*, 2005, 21(3):483-490, which is incorporated herein by reference) which may be adapted for detection of CDH17. High-sensitivity miniaturized immunoassays may also be utilized for detection of CDH17 (Cesaro-Tadic et al., *Lab Chip*, 2004, 4(6):563-569; Zimmerman et al., *Biomed. Microdevices*, 2005, 7(2):99-110, which are incorporated herein by reference).

In a preferred embodiment, the methods of detecting CDH17 nucleic acid in biological fluids of liver cancer patients or those at risk thereof, preferably blood of liver cancer patients or those at risk thereof, include Northern blot analysis, dot blotting, Southern blot analysis, FISH, and PCR.

Nucleic acids including naturally occurring nucleic acids, oligonucleotides, antisense oligonucleotides, and synthetic oligonucleotides that hybridize to the nucleic acid encoding CDH17, are useful as agents to detect the presence of CDH17 in the biological samples of liver cancer patients or those at risk of liver cancer, preferably in the urine of liver cancer patients or those at risk of liver cancer. Useful nucleic acid sequences are those corresponding to the coding sequence of CDH17 and to the complementary sequence thereof, as well as sequences complementary to the CDH17 transcript sequences occurring further upstream or downstream from the coding sequence (e.g., sequences contained in, or extending into, the 5' and 3' untranslated regions). The CDH17 encoding nucleic acid molecules conceivably may be found in the biological fluids inside a Bcl-positive cancer cell that is being shed or released in the fluid under investigation. Oligonucleotide pairs in polymerase chain reactions (PCR) may also be used to detect the expression of CDH17 in biological samples. The oligonucleotide pairs include a forward CDH17 primer and a reverse CDH17 primer.

The preferred oligonucleotides for detecting the presence of CDH17 in biological samples are those that are complementary to at least part of the cDNA sequence encoding CDH17. These complementary sequences are also known in the art as "antisense" sequences. These oligonucleotides may be oligoribonucleotides or oligodeoxyribonucleotides. In addition, oligonucleotides may be natural oligomers composed of the biologically significant nucleotides, i.e., A (adenine), dA (deoxyadenine), G (guanine), dG (deoxyguanine), C (cytosine), dC (deoxycytosine), T (thymine) and U (uracil), or modified oligonucleotide species, substituting, for example, a methyl group or a sulfur atom for a phosphate oxygen in the inter-nucleotide phosohodiester linkage. Additionally, these nucleotides themselves, and/or the ribose moieties may be modified.

The oligonucleotides may be synthesized chemically, using any of the known chemical oligonucleotide synthesis methods well described in the art. For example, the oligonucleotides can be prepared by using any of the commercially available, automated nucleic acid synthesizers. Alternatively, the oligonucleotides may be created by standard recombinant DNA techniques, for example, inducing transcription of the noncoding strand. The DNA sequence encoding CDH17 may be inverted in a recombinant DNA system, e.g., inserted in reverse orientation downstream of a suitable promoter, such that the noncoding strand now is transcribed.

Although any length oligonucleotide may be utilized to hybridize to a nucleic acid encoding CDH17, oligonucleotides typically within the range of 8-100 nucleotides are preferred. Most preferable oligonucleotides for use in detecting CDH17 in urine or blood samples are those within the range of 15-50 nucleotides.

The oligonucleotide selected for hybridizing to the CDH17 nucleic acid molecule, whether synthesized chemically or by recombinant DNA technology, is then isolated and purified using standard techniques, and then preferably labeled with a radioactive label (e.g., with $^{35}S$ or $^{32}P$), a fluorescent label, an enzyme, a chemiluminescent tag, a colorimetric tag or other labels or tags using standard labeling protocols.

The presence of CDH17 in a sample from a patient may be determined by techniques utilizing nucleic acid hybridization, such as but not limited to Northern blot analysis, dot blotting, Southern blot analysis, fluorescence in situ hybridization (FISH), and PCR. Chromatography, preferably HPLC, and other known assays may also be used to determine messenger RNA levels of CDH17 in a sample.

For Northern blot analysis the first step of the analysis involves separating a sample containing CDH17 nucleic acid by gel electrophoresis. The dispersed nucleic acids are then transferred to a nitrocellulose filter or another filter. Subsequently, the labeled oligonucleotide is exposed to the filter under suitable hybridizing conditions, e.g., 50% formamide, 5×SSPE, 2×Denhardt's solution, 0.1% SDS at 42° C., as described in Molecular Cloning: A Laboratory Manual, Maniatis et al. (1982, CSH Laboratory). Other useful procedures known in the art include solution hybridization, dot and slot RNA hybridization, and probe based microarrays. Measuring the radioactivity of hybridized fragments, using standard procedures known in the art quantitates the amount of CDH17 nucleic acid present in the biological fluid of a patient.

Dot blotting involves applying samples containing the nucleic acid of interest to a membrane. The nucleic acid can be denatured before or after application to the membrane. The membrane is incubated with a labeled probe. Dot blot procedures are well known to the skilled artisan and are described more fully in U.S. Pat. Nos. 4,582,789 and 4,617,261, the disclosures of which are incorporated herein by reference.

Polymerase chain reaction (PCR) is a process for amplifying one or more specific nucleic acid sequences present in a nucleic acid sample using primers and agents for polymerization and then detecting the amplified sequence. The extension product of one primer when hybridized to the other becomes a template for the production of the desired specific nucleic acid sequence, and vice versa, and the process is repeated as often as is necessary to produce the desired amount of the sequence. PCR is routinely used in the art to T detect the presence of desired sequence (U.S. Pat. No. 4,683, 195). A specific example of PCR that is routinely performed by the skilled artisan to detect desired sequences is reverse transcript PCR (RT-PCR; Saiki et al., *Science*, 1985, 230: 1350; Scharf et al., *Science*, 1986, 233:1076). RT-PCR involves isolating total RNA from biological fluid, denaturing the RNA in the presence of primers that recognize the desired nucleic acid sequence, using the primers to generate a cDNA copy of the RNA by reverse transcription, amplifying the cDNA by PCR using specific primers, and detecting the amplified cDNA by electrophoresis or other methods known to the skilled artisan.

The methods, devices, and kits described herein can be used in conjunction with one or more additional markers ("biomarkers") for cancer. Therefore, a method for analyzing a biological sample for the presence of CDH17 and analyzing the same sample, or another biological sample from the same subject, for other markers that are specific indicators of a cancer is disclosed. The one or more additional markers may be detected before, during, and/or after detection of CDH17 is carried out. The methods, devices, and kits described herein may be modified by including agents to detect the additional markers, or nucleic acids encoding the markers.

Cancer markers that may be used in conjunction with the disclosed methods include, but are not limited to: alpha fetoprotein (AFP), e.g., for pancreatic, kidney, liver, cervical, and testicular cancers; carcinogenic embryonic antigen (CEA), e.g., for lung, pancreatic, kidney, breast, uterine, liver, gastric, and colorectal cancers; carbohydrate antigen 15-3 (CA15-3), e.g., for lung, pancreatic, breast, and liver cancers; carbohydrate antigen 19-9 (CA19-9), e.g., for lung, uterine, liver, gastric, colorectal, and bile duct cancers; cancer antigen 125 (CA125), e.g., for lung, pancreas, breast, liver, cervical, uterine, gastric, and colorectal cancers; free prostate specific antigen and prostate specific antigen-alpha(1) (PSA), for prostate cancer; free prostate specific antigen (PSAF), for prostate and colorectal cancers; prostate specific antigen-alpha(1)antichymotrypsin complex (PSAC), for prostate cancer; prostatic acid phosphatase (PAP), for prostate cancer; human thyroglobulin (hTG), for thyroid cancer or Wilm's tumor; human chorionic gonadaotropin beta (hCGb), e.g., for lung, pancreatic, kidney, liver, uterine, testicular, colorectal, bladder, and brain cancers; ferritin (Ferr), e.g., for lung cancer, testicular cancer, cancer of the larynx, Burkitt's lymphoma, neuroblastoma, and leukemia; neuron specific enolase (NSE), for lung cancer, thyroid cancer, Wilm's tumor, and neuroblastoma; interleukin 2 (IL-2), for kidney cancer and multiple myeloma; interleukin 6 (IL-6), for kidney cancer, breast cancer, liver cancer, and multiple myeloma; beta 2 microglobulin (B2M), for kidney cancer, liver cancer, prostate cancer, leukemia, multiple myeloma, and lymphoma; and alpha 2 microglobulin (A2M), for prostate cancer. The selection of biological sample (such as blood or urine) in which the aforementioned cancer markers are diagnostic and/or prognostic can be readily determined by those skilled in the art.

The disclosed methods can be carried out on a solid support. A contacting step in the method can involve contacting, combining, or mixing the biological sample and the solid support, such as a reaction vessel, microvessel, tube, microtube, well, multi-well plate, or other solid support.

The solid supports used may be those which are conventional for the purpose of assaying an analyte in a biological sample, and are typically constructed of materials such as cellulose, polysaccharide such as Sephadex, and the like, and may be partially surrounded by a housing for protection and/or handling of the solid support. The solid support can be rigid, semi-rigid, flexible, elastic (having shape-memory), etc., depending upon the desired application. CDH17 can be detected in a sample in vivo or in vitro (ex vivo). When, the amount of CDH17 in a sample is to be determined without removing the sample from the body (i.e., in vivo), the support should be one which is harmless to the subject and may be in any form convenient for insertion into an appropriate part of the body. For example, the support may be a probe made of polytetrafluoroethylene, polystyrene or other rigid non-harmful plastic material and having a size and shape to enable it to be introduced into a subject. The selection of an appropriate inert support is within the competence of those skilled in the art, as are its dimensions for the intended purpose.

Samples and/or CDH17-specific binding agents may be arrayed on the solid support, or multiple supports can be utilized, for multiplex detection or analysis. "Arraying" refers to the act of organizing or arranging members of a library (e.g., an array of different samples or an array of devices that target the same target molecules or different target molecules), or other collection, into a logical or physical array. Thus, an "array" refers to a physical or logical arrangement of, e.g., biological samples. A physical array can be any "spatial format" or "physically gridded format" in which physical manifestations of corresponding library members are arranged in an ordered manner, lending itself to combinatorial screening. For example, samples corresponding to individual or pooled members of a sample library can be arranged in a series of numbered rows and columns, e.g., on a multi-well plate. Similarly, binding agents can be plated or otherwise deposited in microtitered, e.g., 96-well, 384-well, or 1536-well plates (or trays). Optionally, CDH17-specific binding agents may be immobilized on the solid support.

In some embodiments, the support has a fixed organizational support matrix that preferably functions as an organization matrix, such as a microtiter tray. Solid support materials include, but are not limited to, cellulose, polysaccharide such as Sephadex, glass, polyacryloylmorpholide, silica, controlled pore glass (CPG), polystyrene, polystyrene/latex, polyethylene such as ultra high molecular weight polyethylene (UPE), polyamide, polyvinylidine fluoride (PVDF), polytetrafluoroethylene (PTFE; TEFLON), carboxyl modified teflon, nylon, nitrocellulose, and metals and alloys such as gold, platinum and palladium. The solid support can be biological, non-biological, organic, inorganic, or a combination of any of these, existing as particles, strands, precipitates, gels, sheets, pads, cards, strips, dipsticks, test strips, tubing, spheres, containers, capillaries, pads, slices, films, plates, slides, etc., depending upon the particular application. Preferably, the solid support is planar in shape, to facilitate contact with a biological sample such as urine, whole blood, plasma, serum, peritoneal fluid, or ascites fluid. Other suitable solid support materials will be readily apparent to those of skill in the art. The solid support can be a membrane, with or without a backing (e.g., polystyrene or polyester card backing), such as those available from Millipore Corp. (Bedford, Mass.), e.g., Hi-Flow™ Plus membrane cards. The surface of the solid support may contain reactive groups, such as carboxyl, amino, hydroxyl, thiol, or the like for the attachment of nucleic acids, proteins, etc. Surfaces on the solid support will sometimes, though not always, be composed of the same material as the support. Thus, the surface can be composed of any of a wide variety of materials, such as polymers, plastics, resins, polysaccharides, silica or silica-based materials, carbon, metals, inorganic glasses, membranes, or any of the aforementioned support materials (e.g., as a layer or coating).

As demonstrated in the Examples, CDH17-specific monoclonal antibodies can be immobilized on magnetic beads (more specifically, Dynabeads M280 Tosylactivated) for capture of target protein(s) in a large volume, which is usually limited in the microwell or array platforms. Thereby, in certain embodiments, the CDH17-magnetic capture assay is believed to enhance detection sensitivity.

A diagnostic device useful in carrying out the disclosed methods can be constructed in any form adapted for the intended use. In one embodiment, the device can be constructed as a disposable or reusable test strip or stick to be contacted with a biological sample such as urine or blood for which CDH17 level is to be determined. In another embodiment, the device can be constructed using art recognized micro-scale manufacturing techniques to produce needle-like embodiments capable of being implanted or injected into an anatomical site, such as the peritoneal cavity, for indwelling diagnostic applications. In other embodiments, devices intended for repeated laboratory use can be constructed in the form of an elongated probe.

In preferred embodiments, the disclosed devices comprise a solid support (such as a strip or dipstick), with a surface that functions as a lateral flow matrix defining a flow path for a biological sample such as urine, whole blood, serum, plasma, peritoneal fluid, or ascites. The solid support is adapted for immunochromatographic assay of CDH17

Immunochromatographic assays, also known as lateral flow test strips or simply strip tests, for detecting various analytes of interest, are known in the art. The benefits of lateral flow tests include a user-friendly format, rapid results, long-term stability over a wide range of climates, and relatively low cost to manufacture. These features make lateral flow tests ideal for applications involving home testing, rapid point of care testing, and testing in the field for various analytes. The principle behind the test is straightforward. Essentially, any ligand that can be bound to a visually detectable solid support, such as dyed microspheres, can be tested for, qualitatively, and in many cases even semi-quantitatively.

Immunochromatographic assays known in the art may be adapted for detection of CDH17 in biological samples. For example, a one-step lateral flow immunostrip for the detection of free and total prostate specific antigen in serum is described in Fernandez-Sanchez et al. *J. Immuno. Methods*, 307(1-2):1-12 (2005), which is incorporated herein by reference. Some of the more common immunochromatographic assays currently on the market are tests for pregnancy (as an over-the-counter (OTC) test kit), Strep throat, and Chlamydia. Many new tests for well-known antigens have been recently developed using the immunochromatographic assay method. For instance, the antigen for the most common cause of community acquired pneumonia has been known since 1917, but a simple assay was developed only recently, and this was done using this simple test strip method (Murdoch, D. R. et al. *J Clin Microbiol*, 2001, 39:3495-3498). Human immunodeficiency virus (HIV) has been detected rapidly in pooled blood using a similar assay (Soroka, S. D. et al. *J Clin Virol*, 2003, 27:90-96). A nitrocellulose membrane card has also been used to diagnose schistosomiasis by detecting the movement and binding of nanoparticles of carbon (van Dam, G. J. et al. *J Clin Microbiol*, 2004, 42:5458-5461).

The two common approaches to the immunochromatographic assay are the non-competitive (or direct) and competitive (or competitive inhibition) reaction schemes (TechNote #303, Rev. #001, 1999, Bangs Laboratories, Inc., Fishers, Ind.). The direct (double antibody sandwich) format is typically used when testing for larger analytes with multiple antigenic sites such as luteinizing hormone (LH), human chorionic gonadotropin (hCG), and HIV. In this instance, less than an excess of sample analyte is desired, so that some of the microspheres will not be captured at the capture line, and will continue to flow toward the second line of immobilized antibodies, the control zone. This control line uses species-specific anti-immunoglobulin antibodies, specific for the conjugate antibodies on the microspheres. Free antigen, if present, is introduced onto the device by adding sample (urine, serum, etc.) onto a sample addition pad. Free antigen then binds to antibody-microsphere complexes. Antibody 1, specific for epitope 1 of sample antigen, is coupled to dye microspheres and dried onto the device. When sample is added, microsphere-antibody complex is rehydrated and carried to a capture zone and control lines by liquid. Antibody 2, specific for a second antigenic site (epitope 2) of sample antigen, is dried onto a membrane at the capture line. Antibody 3, a species-specific, anti-immunoglobulin antibody that will react with antibody 1, is dried onto the membrane at the control line. If antigen is present in the sample (i.e., a positive test), it will bind by its two antigenic sites, to both antibody 1 (conjugated to microspheres) and antibody 2 (dried onto membrane at the capture line). Antibody 1-coated microspheres are bound by antibody 3 at the control line, whether antigen is present or not. If antigen is not present in the sample (a negative test), microspheres pass the capture line without being trapped, but are caught by the control line.

The competitive reaction scheme is typically used when testing for small molecules with single antigenic determinants, which cannot bond to two antibodies simultaneously. As with double antibody sandwich assay, free antigen, if present is introduced onto the device by adding sample onto a sample pad. Free antigen present in the sample binds to an antibody-microsphere complex. Antibody 1 is specific for sample antigen and couple to dyed microspheres. An antigen-carrier molecule (typically BSA) conjugate is dried onto a membrane at the capture line. Antibody 2 (Ab2) is dried onto the membrane at the control line, and is a species-specific anti-immunoglobulin that will capture the reagent particles and confirm that the test is complete. If antigen is present in the sample (a positive test), antibody on microspheres (Ab1) is already saturated with antigen from sample and, therefore, antigen conjugate bound at the capture line does not bind to it. Any microspheres not caught by the antigen carrier molecule can be caught by Ab2 on the control line. If antigen is not present in the sample (a negative test), antibody-coated dyed microspheres are allowed to be captured by antigen conjugate bound at the capture line.

Normally, the membranes used to hold the antibodies in place on these devices are made of primary hydrophobic materials, such as nitrocellulose. Both the microspheres used as the solid phase supports and the conjugate antibodies are hydrophobic, and their interaction with the membrane allows them to be effectively dried onto the membrane.

Samples and/or CDH17-specific binding agents may be arrayed on the solid support, or multiple supports can be utilized, for multiplex detection or analysis. "Arraying" refers to the act of organizing or arranging members of a library (e.g., an array of different samples or an array of devices that target the same target molecules or different target molecules), or other collection, into a logical or physical array. Thus, an "array" refers to a physical or logical arrangement of, e.g., biological samples. A physical array can be any "spatial format" or physically gridded format" in which physical manifestations of corresponding library members are arranged in an ordered manner, lending itself to combinatorial screening. For example, samples corresponding to individual or pooled members of a sample library can be arranged in a series of numbered rows and columns, e.g., on a multi-well plate. Similarly, binding agents can be plated or otherwise deposited in microtitered, e.g., 96-well, 384-well, or 1536-well plates (or trays). Optionally, CDH17-specific binding agents may be immobilized on the solid support.

Detection of CDH17 and cancer biomarkers, and other assays that are to be carried out on samples, can be carried out simultaneously or sequentially with the detection of other target molecules, and may be carried out in an automated fashion, in a high-throughput format.

The CDH17-specific binding agents can be deposited but "free" (non-immobilized) in the conjugate zone, and be immobilized in the capture zone of a solid support. The CDH17-specific binding agents may be immobilized by non-specific adsorption onto the support or by covalent bonding to the support, for example. Techniques for immobilizing binding agents on supports are known in the art and are described for example in U.S. Pat. Nos. 4,399,217, 4,381,291, 4,357,311, 4,343,312 and 4,260,678, which are incorporated herein by reference. Such techniques can be used to immobilize the CDH17 binding agents. When the solid support is polytetrafluoroethylene, it is possible to couple antibodies onto the support by activating the support using sodium and ammonia to aminate it and covalently bonding the antibody to the activated support by means of a carbodiimide reaction (yon Klitzing, Schultek, Strasburger, Fricke and Wood in "Radioimmunoassay and Related Procedures in Medicine 1982", International Atomic Energy Agency, Vienna (1982), pages 57-62.).

In one embodiment, the device uses lateral flow strip (LFS) technology, which has been applied to a number of other rapid strip assay systems, such as over-the-counter early pregnancy test strips based on antibodies to human chorionic gonadotropin (hCG). As with many other diagnostic devices, the device utilizes a binding agent to bind the target molecule (CDH17). The device has an application zone for receiving a biological sample such as blood or urine, a labeling zone containing label which binds to CDH17 in the sample, a detection zone where CDH17 label is retained, and optionally, a reference zone. Migration of sample from the application zone to the detection zone will generally be assisted by a wick downstream of the detection zone to aid capillary movement. This wick is typically formed from absorbent material such as blotting or chromatography paper.

The labeling zone, and the detection zone contain a binding agent for CDH17. Where the binding agent in the labeling zone and the detection zone are both antibodies, they will typically recognize different epitopes on the target molecule (CDH17 protein). This allows the formation of a "sandwich" comprising antibody-CDH17-antibody.

In a preferred embodiment, the detection, reference and control zones are preferably formed on a nitrocellulose support.

The device can be produced simply and cheaply, conveniently in the form of a dipstick. Furthermore, it can be used very easily, for instance by the home user, therefore, providing a device which can be used at home as a screen for cancer, such as liver cancer.

The application zone in the device is suitable for receiving the biological sample to be assayed. It is typically formed from absorbent material such as blotting paper.

The labeling zone contains binding agent that binds to any CDH17 in the sample. The binding agent may be an antibody for example, a monoclonal antibody, polyclonal antibody, or an antibody fragment. For ease of detection, the binding agent is preferably in association with a label that provides a signal that is visible to the naked eye, e.g., it is tagged with a fluorescent tag or a colored tag such as conjugated colloidal gold, which is visible as a pink color.

The detection zone is downstream of the application zone, with the labelling zone typically located between the two. The detection zone retains CDH17 to which the binding agent has bound. This will typically be achieved using an immobilized binding agent such as an immobilized antibody. A sample will thus migrate from the application zone into the labeling zone, where any CDH17 in the sample binds to the label.

CDH17-binding agent complexes continue to migrate into the detection zone together with excess binding agent. When the CDH17-binding agent complex encounters the capture reagent, the complex is retained whilst the sample and excess binding agent continue to migrate. As CDH17 levels in the sample increase, the amount of binding agent (in the form of CDH17-binding agent complex) retained in the detection zone increases proportionally.

Binding agent retained in the detection zone gives a signal, and the signal differs depending on whether CDH17 levels in the biological sample are lower than, equal to, or greater than a given threshold concentration. For example, in the case of serum CDH17 for the detection of liver cancer, the threshold concentration may be between 0 ng/ml and 2.0 ng/ml. In another embodiment, in the case of serum CDH17 for the detection of liver cancer, the threshold concentration is 1.8 ng/ml. A sample from a subject having a CDH17 level equal to or greater than the given reference CDH17 concentration can be referred to as a "threshold level", "threshold amount", or "threshold sample".

In preferred embodiments, the device has the ability to distinguish between samples according to the threshold concentration. This can be achieved in various ways.

In some embodiments the devise includes a reference zone which contains a signal of fixed intensity against which the amount of binding agent retained in the detection zone can be compared; when the signal in the detection zone equals the signal in the reference zone, the sample is a threshold sample; when the signal in the detection zone is less intense than the reference zone, the sample contains less CDH17 than a threshold sample; when the signal in the detection zone is more intense than the reference zone, the sample contains more CDH17 than a threshold sample. A suitable reference zone can be prepared and calibrated without difficulty. For this type of device, the binding agent will generally be present in excess to CDH17 in the sample, and the reference zone may be upstream or, preferably, downstream of the detection zone. The signal in the reference zone will be of the same type as the signal in the detection zone, i.e., they will typically both be visible to the naked eye, e.g., they will use the same tag. A preferred reference zone in a device of this type comprises immobilized protein (e.g., bovine serum albumin) which is tagged with colloidal gold.

In other embodiments of the device including a reference zone, the reference zone is downstream of the detection zone and includes a reagent which captures binding agent (e.g., an immobilised anti-binding agent antibody). Binding agent that flows through the device is not present in excess, but is at a concentration such that 50% of it is bound by a sample having CDH17 at the threshold concentration. In a threshold sample, therefore, 50% of the binding agent will be retained in the detection zone and 50% in the reference zone. If the CDH17 level in the sample is greater than in a threshold sample, less than 50% of the binding agent will reach the reference zone and the detection zone will give a more intense signal than the reference zone; conversely, if the CDH17 level in the sample is less than in a threshold sample, less than 50% of the binding agent will be retained in the detection zone and the reference zone will give a more intense signal than the detection zone.

In still other embodiments of the device including a reference zone (which operates according to similar principles), the reference zone is downstream of the detection zone and includes a limiting amount of a reagent which captures binding agent (e.g., an immobilised anti-binding agent antibody). The reagent is present at a level such that it retains the same amount of label which would bind to the detection zone for a threshold sample, with excess label continuing to migrate beyond the reference zone.

In these three types of device, therefore, a comparison between the detection zone and the reference zone is used to compare the sample with the threshold concentration. The detection:reference binding ratio can preferably be determined by eye. Close juxtaposition of the detection and reference zones is preferred in order to facilitate visual comparison of the signal intensities in the two zones.

In some embodiments of the device, no reference zone is needed, but the detection zone is configured such that it gives an essentially on/off response, e.g., no signal is given below the threshold concentration but, at or above the threshold, signal is given.

In other embodiment of the device, no reference zone is needed, but an external reference is used which corresponds to the threshold concentration. This can take various forms, e.g., a printed card against which the signal in the detection zone can be compared, or a machine reader which compares an absolute value measured in the detection zone (e.g., a calorimetric signal) against a reference value stored in the machine.

In still another embodiment of the device, the device includes a control zone downstream of the detection zone. This will generally be used to capture excess binding agent that passes through the detection and/or reference zones (e.g., using immobilized anti-binding agent antibody). When binding agent is retained at the control zone, this confirms that mobilization of the binding agent and migration through the device have both occurred. It will be appreciated that this function may be achieved by the reference zone.

In still other devices, using electromagnetic sensor, the detection sensitivity can be greatly enhanced, and can also increase the speed of the assay.

Kits for detecting the presence of the target gene in a biological sample are provided. Such kits can be used to determine if a subject is suffering from or is at increased risk of developing a disorder associated with aberrant expression of the target gene (e.g., the presence of a drug resistance cancer). For example, the kit can comprise a labeled compound or agent capable of detecting the target gene protein or mRNA in a biological sample and means for determining the amount of the target gene in the sample (e.g., an anti-target gene antibody or an oligonucleotide probe which binds to DNA encoding the target gene). Kits may also include instruction for observing that the tested subject is suffering from or is at risk of developing a disorder associated with aberrant expression of the target gene if the amount of the target gene protein or mRNA is above or below a normal level.

Kits for diagnosing or monitoring liver cancer are provided. In one embodiment includes kits comprising the required elements for diagnosing or monitoring cancer. Preferably, the kits comprise a container for collecting biological fluid from a patient and an agent for detecting the presence of CDH17 or its encoding nucleic acid in the fluid. The components of the kits can be packaged either in aqueous medium or in lyophilized form.

The detection/diagnostic methods disclosed herein can be carried out using a diagnostic kit for qualitatively or quantitatively detecting CDH17 in a sample such as blood or urine. Thus, the kits include reagents for use in the methods described herein, in one or more containers. The kits may include primers, specific internal controls, and/or probes, buffers, and/or excipients, separately or in combination. Each reagent can be supplied in a solid form or liquid buffer that is suitable for inventory storage. Kits may also include means for obtaining a sample from a host organism or an environmental sample.

For antibody-based kits, the kit may comprise, for example: (1) a first antibody (e.g., attached to a solid support) which binds to the target gene protein; and, optionally, (2) a second, different antibody which binds to the target gene protein or the first antibody and is conjugated to a detectable agent.

For oligonucleotide-based kits, the kit may comprise, for example: (1) a oligonucleotide, e.g., a detectably labelled oligonucleotide, which hybridizes to the target gene nucleic acid sequence or (2) a pair of primers useful for amplifying the target gene nucleic acid molecule.

The kit may also comprise, e.g., a buffering agent, a preservative, or a protein stabilizing agent. The kit may also comprise components necessary for detecting the detectable agent (e.g., an enzyme or a substrate). The kit may also contain a control sample or a series of control samples which can be assayed and compared to the test sample contained. Each component of the kit is usually enclosed within an individual container and all of the various containers are within a single package along with instructions for observing whether the tested subject is suffering from or is at risk of developing a disorder associated with aberrant expression of the target gene.

By way of example, the kit can contain binding agents (e.g., antibodies) specific for CDH17, antibodies against the antibodies labeled with an enzyme; and a substrate for the enzyme. The kit can also contain a solid support such as microtiter multi-well plates, standards, assay diluent, wash buffer, adhesive plate covers, and/or instructions for carrying out a method as disclosed herein, using the kit. In one embodiment, the kit includes one or protease inhibitors (e.g., a protease inhibitor cocktail) to be applied to the biological sample to be assayed (such as blood or urine).

In some embodiments kits containing one or more agents that detect the CDH17 protein, such as but not limited to CDH17 antibodies, fragments thereof, or CDH17 binding partners, can be prepared. The agent(s) can be packaged with a container for collecting the biological fluid from a patient. When the antibodies or binding partner are used in the kits in the form of conjugates in which a label is attached, such as a radioactive metal ion or a moiety, the components of such conjugates can be supplied either in fully conjugated form, in the form of intermediates or as separate moieties to be conjugated by the user of the kit.

In other embodiments, kits containing one or more agents that detect CDH17 nucleic acid, such as but not limited to the full length CDH17 nucleic acid, CDH17 oligonucleotides, and pairs of CDH17 primers can also be prepared. The agent(s) can be packaged with a container for collecting biological samples from a patient. The nucleic acid can be in the labeled form or to be labeled form.

Other components of the kit may include but are not limited to, means for collecting biological samples, means for labeling the detecting agent (binding agent), membranes for immobilizing the CDH17 protein or CDH17 nucleic acid in the biological sample, means for applying the biological sample to a membrane, means for binding the agent to CDH17 in the biological sample of a subject, a second antibody, a means for isolating total RNA from a biological fluid of a subject, means for performing gel electrophoresis, means for generating cDNA from isolated total RNA, means for performing hybridization assays, and means for performing PCR, etc.

The kits may optionally be provided in suitable packaging. As used herein, "packaging" refers to a solid matrix or material customarily used in a system and capable of holding within fixed limits one or more of the reagent components for use in the disclosed diagnostic/detection method. Such materials include glass and plastic (e.g., polyethylene, polypropylene, and polycarbonate) bottles, vials, paper, plastic, and plastic-foil laminated envelopes and the like. Preferably, the solid matrix is a structure having a surface that can be derivatized to anchor an oligonucleotide probe, primer, molecular beacon, specific internal control, etc. Preferably, the solid matrix is a planar material such as the side of a microtiter well or the side of a dipstick. In certain embodiments, the kit includes a microtiter tray with two or more wells and with reagents including primers, probes, specific internal controls, and/or molecular beacons in the wells.

The kits may optionally include a set of instructions in printed or electronic (e.g., magnetic or optical disk) form, relating information regarding the components of the kits and/or how to make various determinations (e.g., CDH17 levels, comparison to control standards, etc.). The kit may also be commercialized as part of a larger package that includes instrumentation for measuring other biochemical components.

VI. Screening Assays for CDH17 Antagonists

A method for identifying (also referred to herein as a "screening assay") CDH17 inhibitors, i.e., candidate or test compounds or agents (e.g., peptides, peptidomimetics, small molecules or other drugs) that bind to the CDH17 protein or have a stimulatory or inhibitory effect on, for example, the CDH17 gene expression or CDH17 gene activity. Such identified compounds may be useful for the modulation of drug resistance. The test compounds can be obtained using any of the numerous approaches in combinatorial library methods known in the art, including: biological libraries; natural products libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. *Proc. Natl. Acad. Sci. USA*, 1993, 90:6909; Erb et al. *Proc. Natl. Acad. Sci. USA*, 1994, 91:11422; Zuckermann et al. *J. Med. Chem.*, 1994, 37:2678; Cho et al. *Science*, 1993, 261:1303; Carrell et al. *Angew. Chem. Int. Ed. Engl.*, 1994, 33:2059; Carell et al. *Angew. Chem. Int. Ed. Engl.*, 1994, 33:2061; and Gallop et al. *J. Med. Chem.*, 1994, 37:1233.

Libraries of compounds may be presented in solution (e.g., Houghten *Bio/Techniques*, 1992, 13:412-421), or on beads (Lam *Nature*, 1991, 354:82-84), chips (Fodor *Nature*, 1993, 364:555-556), bacteria (U.S. Pat. No. 5,223,409), spores (U.S. Pat. Nos. 5,571,698; 5,403,484; and 5,223,409), plasmids (Cull et al. *Proc. Natl. Acad. Sci. USA*, 1992, 89:1865-1869) or on phage (Scott and Smith *Science*, 1990, 249:386-390; Devlin *Science*, 1990, 249:404-406; Cwirla et al. *Proc. Natl. Acad. Sci.*, 1990, 87:6378-6382; and Felici *J. Mol: Biol.*, 1991, 222:301-310).

In one embodiment, an assay is a cell-based assay in which a cell which expresses the target gene protein, or a biologically active portion thereof, is contacted with a test compound and the ability of the test compound to bind to the target gene protein is determined. The cell, for example, can be a yeast cell or a cell of mammalian origin. Determining the ability of the test compound to bind to the target gene protein can be accomplished, for example, by coupling the test compound with a radioisotope or enzymatic label such that binding of the test compound to the target gene protein or biologically active portion thereof can be determined by detecting the labeled compound in a complex. For example, test compounds can be labeled with $^{125}I$, $^{35}S$, $^{14}C$, or $^3H$, either directly or indirectly, and the radioisotope detected by direct counting of radioemission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a preferred embodiment, the assay comprises contacting a cell which expresses the target gene protein, or a biologically active portion thereof, with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the test compound to preferentially bind to the target gene or a biologically active portion thereof as compared to the known compound.

In another embodiment, an assay is a cell-based assay comprising contacting a cell expressing the target gene protein, or a biologically active portion thereof, with a test compound and determining the ability of the test compound to modulate (e.g., stimulate or inhibit) the activity of the target gene protein or biologically active portion thereof. Determining the ability of the test compound to modulate the activity of the target gene or a biologically active portion thereof can be accomplished, for example, by determining the ability of the target gene protein to bind to or interact with the target gene target molecule. As used herein, a "target molecule" is a molecule with which the target gene protein binds or interacts in nature, for example, a molecule in the nucleus or cytoplasm of a cell which expresses the target gene protein. The target gene target molecule can be a non-target gene molecule or the target gene protein or polypeptide. The target, for example, can be a second intracellular protein which has catalytic activity, a protein which naturally binds to the target gene, or a protein which facilitates the association of DNA with the target gene.

Determining the ability of the target gene protein to bind to or interact with the target gene target molecule can be accomplished by one of the methods described above for determining direct binding. In a preferred embodiment, determining the ability of the target gene protein to bind to or interact with the target gene target molecule can be accomplished by determining the activity of the target molecule or detecting a cellular response, for example, cell survival or cell proliferation in the presence of a chemotherapeutic drug.

In yet another embodiment, an assay method is a cell-free assay comprising contacting the target gene protein or biologically active portion thereof with a test compound and determining the ability of the test compound to bind to the target gene protein or biologically active portion thereof. Binding of the test compound to the target gene protein can be determined either directly or indirectly as described above. In a preferred embodiment, the assay includes contacting the target gene protein or biologically active portion thereof with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the test compound to preferentially bind to the target gene or biologically active portion thereof as compared to the known compound.

In another embodiment, an assay is a cell-free assay comprising contacting the target gene protein or biologically active portion thereof with a test compound and determining the ability of the test compound to modulate (e.g., stimulate or inhibit) the activity of the target gene protein or biologically active portion thereof. Determining the ability of the test compound to modulate the activity of the target gene can be accomplished, for example, by determining the ability of the target gene protein to bind to the target gene target molecule by one of the methods described above for determining direct binding. In an alternative embodiment, determining the ability of the test compound to modulate the activity of the target gene can be accomplished by determining the ability of the target gene protein further modulate the target gene target molecule. For example, the catalytic/enzymatic activity of the target molecule on an appropriate substrate can be determined as previously described.

In yet another embodiment, the cell-free assay comprises contacting the target gene protein or biologically active portion thereof with a known compound which binds the target gene to form an assay mixture, contacting the assay mixture with a test compound, and determining the ability of the test compound to interact with the target gene protein, wherein determining the ability of the test compound to interact with the target gene protein comprises determining the ability of the target gene protein to preferentially bind to or modulate the activity of the target gene target molecule.

The disclosed cell-free assays are amenable to use of both native and variant forms (e.g., peptide fragments and fusion proteins) of the target gene. In the case of cell-free assays comprising a hydrophobic form of the target gene, it may be desirable to utilize a solubilizing agent such that the hydrophobic form of the target gene is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In some embodiments, it may be desirable to immobilize either the target gene or its target molecule to facilitate separation of complexed from uncomplexed forms of one or both of the proteins, as well as to accommodate automation of the assay. Binding of a test compound to the target gene, or interaction of the target gene with a target molecule in the presence and absence of a candidate compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the proteins to be bound to a matrix. For example, glutathione-S-transferase/target gene fusion proteins or glutathione-S-transferase/target fusion proteins can be adsorbed onto glutathione sepharose beads (Sigma Chemical; St. Louis, Mo.) or glutathione derivatized microtitre plates, which are then combined with the test compound or the test compound and either the non-adsorbed target protein or the target gene protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of the target gene binding or activity determined using standard techniques.

Other techniques for immobilizing proteins on matrices can also be used in the screening assays. For example, either the target gene or its target molecule can be immobilized utilizing conjugation of biotin and streptavidin. Biotinylated target gene or target molecules can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with the target gene or target molecules but which do not interfere with binding of the target gene protein to its target molecule can be derivatized to the wells of the plate, and unbound target or the target gene trapped in the wells by antibody conjugation. Methods for detecting such complexes, in addition to those described above for the GST-immobilized complexes, include immunodetection of complexes using antibodies reactive with the target gene or target molecule, as well as enzyme-linked assays which rely on detecting an enzymatic activity associated with the target gene or target molecule.

In another embodiment, modulators of the target gene expression are identified in a method in which a cell is contacted with a candidate compound and the expression of the target gene (mRNA or protein, or the copy number of the target gene) in the cell is determined. The level of expression of the target gene in the presence of the candidate compound is compared to the level of expression of the target gene in the absence of the candidate compound. The candidate compound can then be identified as a modulator of the target gene expression based on this comparison. For example, when expression of the target gene mRNA or protein is greater (statistically significantly greater) in the presence of the candidate compound than in its absence, the candidate compound is identified as a stimulator of the target gene mRNA or protein expression. Alternatively, when expression of the target gene mRNA or protein is less (statistically significantly less) in the presence of the candidate compound than in its absence, the candidate compound is identified as an inhibitor of the target gene mRNA or protein expression. The level of the target gene mRNA or protein expression in the cells, or the number of the target gene copies per cell can be determined by methods described herein for detecting the target gene genomic DNA, mRNA, or protein.

Target gene proteins can be used as "bait proteins" in a two-hybrid assay or three hybrid assay (see, e.g., U.S. Pat. No. 5,283,317; Zervos et al. *Cell*, 1993, 72:223-232; Madura et al. *J. Biol. Chem.*, 1993, 268:12046-12054; Bartel et al. *Bio/Techniques*, 1993, 14:920-924; Iwabuchi et al. *Oncogene*, 1993, 8:1693-1696; and WO94/10300), to identify other proteins, which bind to or interact with the target gene ("target gene-binding proteins" or "target gene-bp") and modulate the target gene activity.

The two-hybrid system is based on the modular nature of most transcription factors, which consist of separable DNA-binding and activation domains. Briefly, the assay utilizes two different DNA constructs. In one construct, the gene that codes for the target gene is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming the target gene-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the target gene.

Thus novel agents identified by the above-described screening assays and uses thereof for treatments as described herein are also provided.

VII. Pharmacogenomics

Another aspect provides methods for determining the target gene protein, nucleic acid expression or the target gene activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent).

Agents, or modulators which have a stimulatory or inhibitory effect on the target gene activity (e.g., CDH17) as identified by a screening assay can be administered to individuals to treat (prophylactically or therapeutically) disorders (e.g., anemias) associated with aberrant target gene activity. In conjunction with such treatment, the pharmacogenomics (i.e., the study of the relation CDH17 between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of the target gene protein, expression of the target gene nucleic acid, or mutation content of the target genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder, *Clin. Chem.*, 1997, 43(2): 254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

Thus, the activity of the target gene product (CDH17), expression of the target gene nucleic acid, or mutation content of the target genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with the target gene modulator, such as a modulator identified by one of the exemplary screening assays described herein.

VIII. Monitoring of Effects During Clinical Trials

Monitoring the influence of agents (e.g., drugs, compounds) on the expression or activity of the target gene (e.g., the ability to modulate the CDH17 phenotype of a cell) can be applied not only in basic drug screening, but also in clinical trials. For example, the effectiveness of an agent determined by a screening assay to decrease the target gene expression, protein levels, or downregulate the target gene activity, can be monitored in clinical trails of subjects exhibiting increased target gene expression, protein levels, or upregulated target gene activity.

Alternatively, the effectiveness of an agent determined by a screening assay to increase the target gene expression, protein levels, or upregulate target gene activity (e.g., to decrease megakaryocyte production), can be monitored in clinical trials of compounds designed to increase the target gene expression, protein levels, or upregulate target gene activity. In such clinical trials, the expression or activity of the target gene and, preferably, other genes that have been implicated in, for example, a cellular proliferation disorder, can be used as a "read out" or markers of the drug resistance of a particular cell.

For example, and not by way of limitation, genes, including the target gene, that are modulated in cells by treatment with an agent (e.g., compound, drug or small molecule) which modulates the target gene activity (e.g., identified in a screening assay) can be identified. Thus, to study the effect of agents on cellular proliferation disorders, for example, in a clinical trial, cells can be isolated and RNA prepared and analyzed for the levels of expression of the target gene and other genes implicated in the disorder. The levels of gene expression (i.e., a gene expression pattern) can be quantified by Northern blot analysis or RT-PCR, or as is otherwise known in the art, or alternatively by measuring the amount of protein produced, by one of the methods as described herein, or by measuring the levels of activity of the target gene or other genes. In this way, the gene expression pattern can serve as a marker, indicative of the physiological response of the cells to the agent. Accordingly, this response state may be determined before, and at various points during, treatment of the individual with the agent.

In a preferred embodiment, a method for monitoring the effectiveness of treatment of a subject with an agent (e.g., an agonist, antagonist, peptidomimetic, protein, peptide, nucleic acid, small molecule, or other drug candidate identified by the screening assays described herein) comprises the steps of (i) obtaining a pre-administration sample from a subject prior to administration of the agent; (ii) detecting the level of expression of the target gene protein, mRNA, or genomic DNA in the preadministration sample; (iii) obtaining one or more post-administration samples from the subject; (iv) detecting the level of expression or activity of the target gene protein, mRNA, or genomic DNA in the post-administration samples; (v) comparing the level of expression or activity of the target gene protein, mRNA, or genomic DNA in the pre-administration sample with the target gene protein, mRNA, or genomic DNA in the post administration sample or samples; and (vi) altering the administration of the agent to the subject accordingly. For example, increased administration of the agent may be desirable to decrease the expression or activity of the target gene to lower levels than detected, i.e., to increase the effectiveness of the agent.

Unless defined otherwise, all technical and scientific terms have the same meaning as commonly understood by one of ordinary skill in the art to which this invention belongs. Although any methods and materials similar or equivalent to those described herein can be used in the practice or testing of the present invention, the preferred methods and materials are now described.

All publications and patent applications mentioned herein are incorporated by reference to disclose and describe the methods and/or materials in connection with which the publications are cited. All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting.

EXAMPLES

Example 1

CDH17 mRNA Levels in Human HCC Cell Lines and Cancer Patients

Materials and Methods

The CDH17 mRNA level in a panel of human HCC cell lines with different metastatic potential was measured using qPCR analysis. The control cell line MIHA was an immortalized normal human hepatocyte, which expressed very little or undetectable CDH17. Primary HCC cell lines expressed some CDH17 transcript while strong expression was seen in their metastatic counterparts (e.g. MHCC97-H, MHCC97-L and H2-M).

These cell line data were supported by results from 46 pairs of tumor and adjacent liver tissues from HCC patients who received curative surgery. Table 3 below was prepared based on the correlation analysis performed in a total of 46 HCC patients with defined clinical data. mRNA was extracted in clinical samples using standard protocol and reverse transcribed to cDNA for determining the expression of CDH17 transcript using quantitative polymerase chain reaction (qPCR). Categorical parameters of clinical samples were compared using $\chi^2$ test.

Results

Correlating the qPCR data with the clinical parameters revealed an association of CDH17 overexpression with late tumor stage (III-IV) and presence of venous infiltration, whereas no significant correlation was found for other parameters. Overexpression of CDH17 was strongly associated with advanced tumor stages (pTNM III and IV) (p=0.022) and tumor venous invasion (p=0.022). No significant correlation was found for other clinicopathologic Parameters. Most strikingly, copy number variation analysis revealed genomic amplification of the CDH17 gene in the tumor compared with adjacent non-tumor tissues in 49% of HCC cases that were analyzed (n=231) (data not shown). Taken together, these results suggest that CDH17 is a candidate target for intervening in the initiation and metastasis of HCC.

TABLE 3

Statistical correlation between the expression of CDH17 and the clinicopathological parameters of HCC patients (n = 46).

| Clinicopathological parameters | Frequency (%) | CDH17 Over-expression | | P value |
|---|---|---|---|---|
| | | − | + | |
| Gender | | | | 0.116 |
| Male | 37 (80.4) | 19 | 18 | |
| Female | 9 (19.6) | 2 | 7 | |
| Age | | | | 0.305 |
| <60 | 34 (73.9) | 14 | 20 | |
| ≥60 | 12 (26.1) | 7 | 5 | |
| Tumor size (cm) | | | | 0.786 |
| <5 | 8 (17.4) | 4 | 4 | |
| ≥5 | 38 (82.6) | 17 | 21 | |
| Alpha fetoprotein (AFP) (ng/ml) | | | | 0.226 |
| <250 | 24 (52.2) | 13 | 11 | |
| ≥250 | 22 (47.8) | 8 | 14 | |
| HBsAg | | | | 0.126 |

TABLE 3-continued

Statistical correlation between the expression of CDH17 and the clinicopathological parameters of HCC patients (n = 46).

| Clinicopathological parameters | Frequency (%) | CDH17 Over-expression | | P value |
|---|---|---|---|---|
| | | − | + | |
| Negative | 6 (1.0) | 1 | 5 | |
| Positive | 40 (87.0) | 20 | 20 | |
| Histological differentiation | | | | 0.261 |
| Well | 26 (61.9) | 9 | 7 | |
| Moderately, Poorly | 16 (38.1) | 10 | 16 | |
| TNM stage | | | | 0.022* |
| Early (I, II) | 18 (39.1) | 12 | 6 | |
| Late (III, IV) | 28 (60.9) | 9 | 19 | |
| Venous infiltration | | | | 0.022* |
| Absent | 18 (39.1) | 12 | 6 | |
| Present | 28 (60.9) | 9 | 19 | |
| Recurrence | | | | 0.161 |
| Absent | 35 (76.1) | 18 | 17 | |
| Present | 11 (23.9) | 3 | 8 | |
| Cirrhosis | | | | 0.375 |
| Negative | 23 (50.0) | 9 | 14 | |
| Positive | 23 (50.0) | 12 | 11 | |

*statistically significant (p < 0.05)

Example 2

CDH17 Levels Predict Microvascular Invasion and Disease Prognosis in Cancer Patients The data above was further confirmed by Ding, et al., *Cancer*, 115 July, 2009, the contents of which are incorporated herein by reference. Ding, et al., evaluated CDH17 expression in three HBV-positive HCC cell lines and in tissued samples from HCC cancer patients. Western blot and immunofluresence analysis showed a significant increase in CDH17 protein levels in high-invasive HCCLM3 cells compared to low-invasive Hep3B and PLC/PRF/5 cells. The effect of CDH17 expression on cell migration (a characteristic of metastasis) was investigated in the high-invasive cell line using a wound healing migration assay. Using SiRNA-mediated inhibition, Ding, et al., *showed that CDH17* inhibition resulted in a significant delay in wound closure in the HCCLM3-SiRNA-treated cells, when compared to the control cells, confirming the involvement of CDH17 in cancer cell migration. In a Matrigel invasion assay, Ding, et al. also showed that SiRNA-mediated inhibition of CDH17 resulted in a 57% reduction in invaded cells in the HCCLM3-SiRNA-treated cells compared to the control cells.

Immunohistochemical analysis of 50 pairs of HCC and adjacent nontumor tissue was used to confirm the relationship between CDH17 and microvascular metastasis in patients with HBV-related HCC. Of the 50 HCC patient samples tested, 36 (72%) showed overexpression of CDH17, which was associated with vascular invasion. Since Microvascular invasion is a predictor of tumor recurrence or poor prognosis in HCC patients undergoing curative resection, Ding, et al. studied the correlation between CDH17 overexpression and prognosis in HBV-positive HCC using the Kaplan-Meier Survival test. The results showed that patients with positive CDH17 expression had a poorer prognosis that those without CDH17 expression.

Example 3

Reduction in Size of Tumor Xenograft after Silencing the Expression of CDH17 in MHCC97-H (97H) in Liver Tumor Cells Materials and Methods 97H cells are derived from liver tumor cells with high metastatic potentials. These cells were transfected stably with either vector alone (Mock) or short hairpin-RNA (shRNA) (see SEQ ID NO: 2) targeting exon 3 (SEQ ID NO: 5) of CDH17 (shCDH17). 97H cells with (Mock or shCDH17) or without (97H) transfection were inoculated in nude mice for a period of up to 8 weeks. Changes in tumor volume were quantified and represented in the chart.

Results

The results are shown in FIG. 1. Growth of subcutaneous tumors was observed visually and using a fluorescent imaging technique four weeks after cell inoculation. Appearance and size of the subcutaneous tumors were shown after dissecting the tumors from mice on 8-week after cell inoculation. A significant reduction in size of the tumor xenografts was observed when the expression of CDH17 was suppressed.

In similar experiments in which the 97H tumor cells were transplanted subcutaneously or injected systemically, all control animals (Mock group) developed metastasis in the lungs as shown by the presence of GFP-positive tumor cells at 8 weeks regardless of whether the 97H tumor cells were transplanted subcutaneously or injected systemically. By contrast, no lung metastasis was observed in animals from the CDH17 shRNAmir treatment group. Thus knockdown of CDH17 not only reduced tumor growth but also diminished the metastatic potential of hepatic carcinoma. This has a great clinical implication since most of the HCC patients die from tumor recurrence due to intra- or extra-hepatic metastasis.

Example 4

Figure 2A:
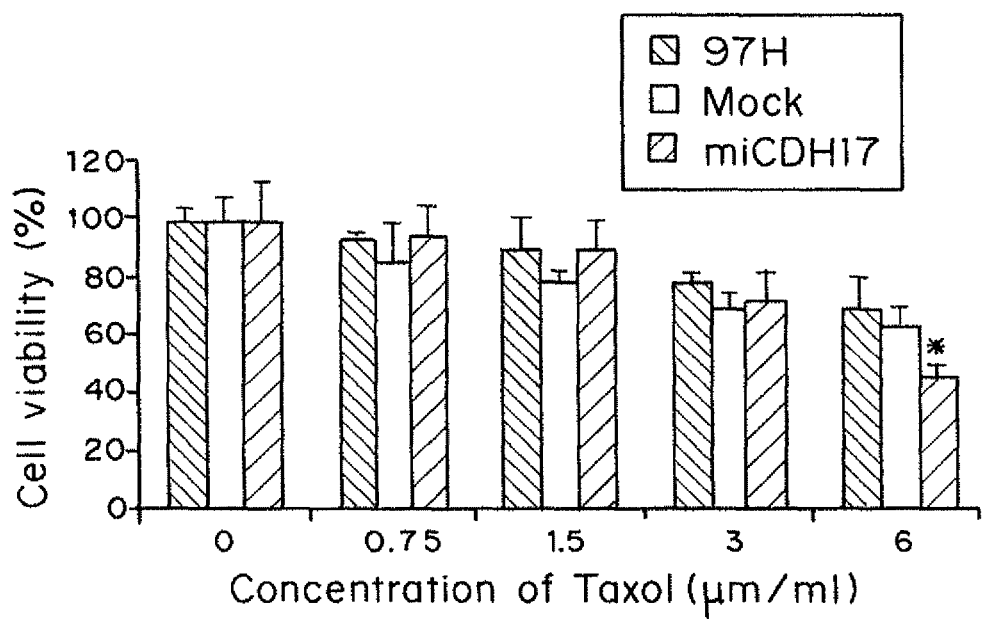
FIGS. 2A, 2B, 2C and 2D are bar graphs showing the sensitization of MHCC97-H (97H) liver tumor cells to Taxol (FIG. 2A, µm/ml), Carboplatin (FIG. 2B, mg/ml), Epirubicin (FIG. 2C, µg/ml) and gene therapy (2D, viral titre rAd-p53, $\times 10^7$) after silencing the expression of CDH17, plotting percent cell viability to drug concentration.
Figure 2B:
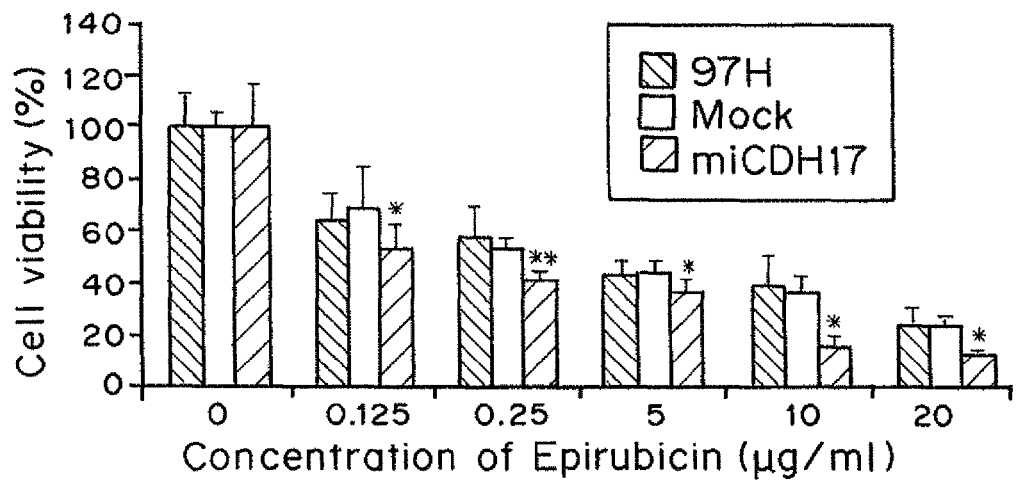
Figure 2C:
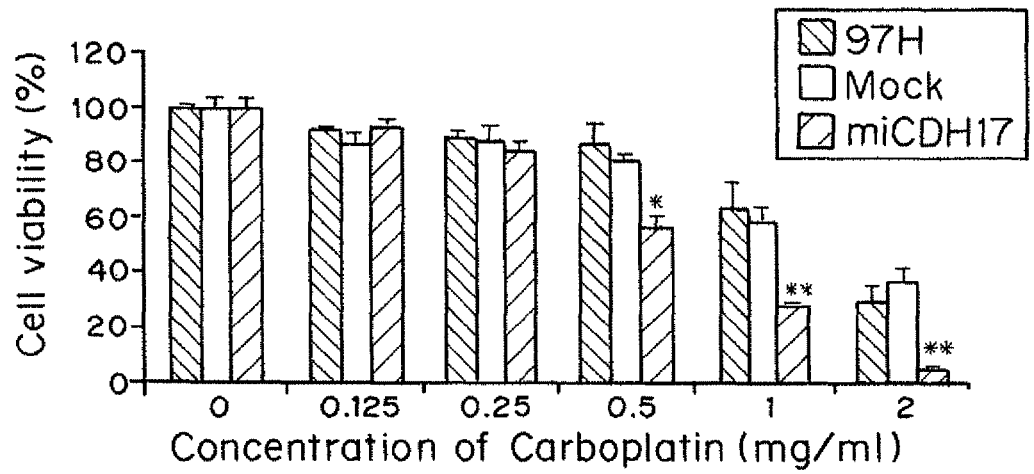
Figure 2D:
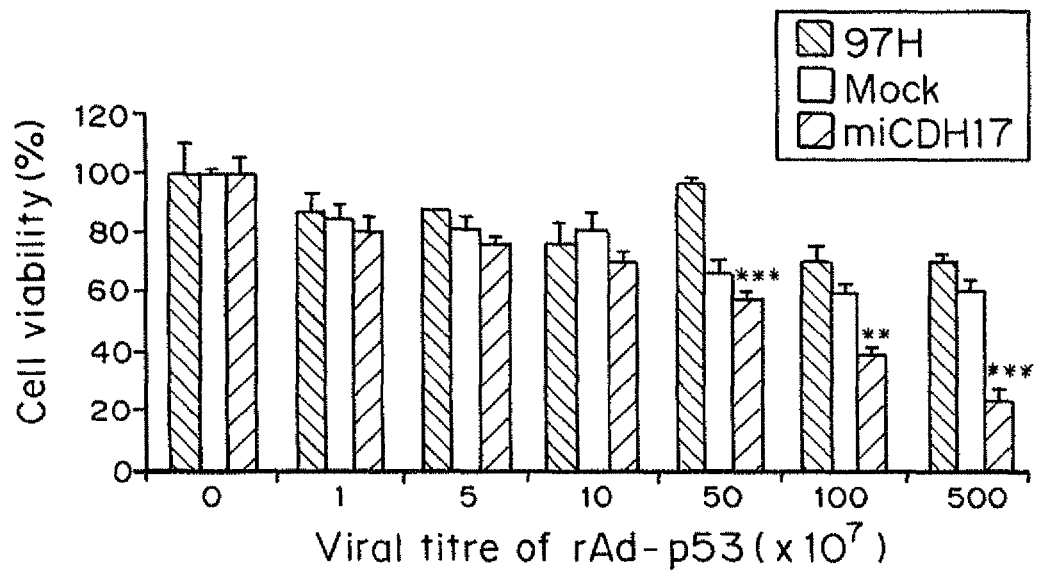

MHCC97-H (97H) Liver Tumor Cells are Sensitized to Drug and Gene Therapy after RNAi-Mediated Silencing of CDH17 Expression Materials and Methods 97H cells are derived from liver tumor cells with high metastatic potentials. These cells were transfected stably with either vector alone (Mock) or short hairpin-RNA (shRNA) (see SEQ ID NO: 2) targeting exon 3 (SEQ ID NO: 5) of CDH17 (miCDH17). 97H cells (97H, Mock, and miCDH17) were treated with different concentrations of chemotherapeutic drugs, such as Taxol (FIG. 2A), Carboplatin (FIG. 2C), and Epirubicin (FIG. 2B). In addition, 97H cells of different groups were transfected with p53, a tumor suppressor, using adenovirus-mediated approach (rAd-p53) (FIG. 2D). Cell viability of different treatment groups was assessed by MTT assay.

Results

The administration of a CDH17 inhibitor, a shRNA, sensitizes tumor cells to treatment with other chemotherapeutic agents including drugs such as taxol, carboplatin and epirubicin, as well as a p53 tumor suppressor administered in an adeno-viral vector. 97H tumor cells were sensitized to treatments of chemotherapy and gene therapy.

Figure 3A:
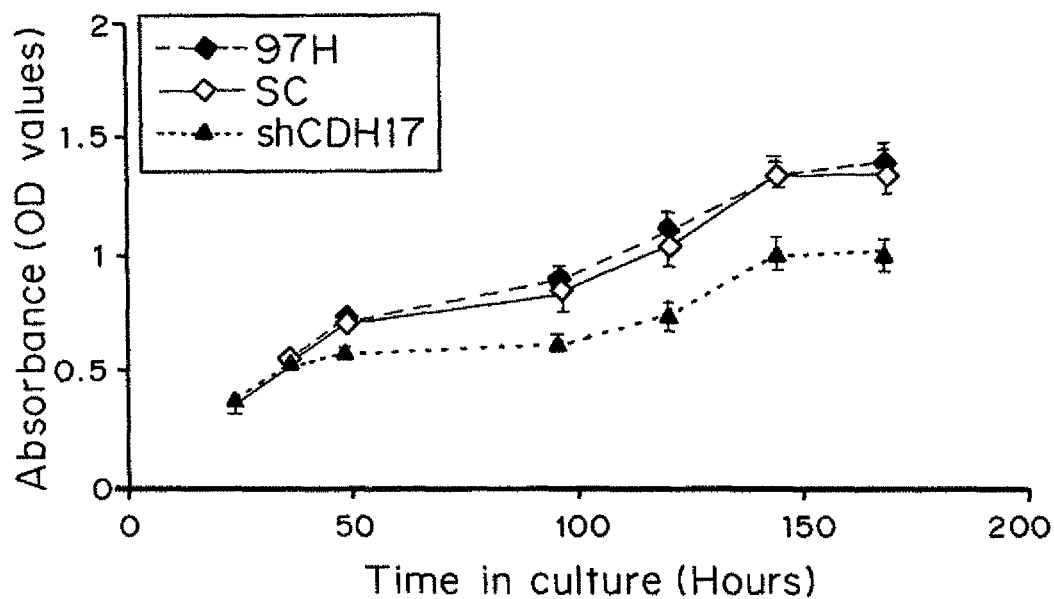
FIGS. 3A, 3B, 3C, and 3D are graphs comparing the effects of transfecting 97H cells with shRNA targeting the CDH17 exon 5 with the effects of 97H and scramble (SC) on CDH17 protein level (FIG. 3A, absorbance versus time, hours), cell proliferation (FIG. 3B, cell concentration), cell invasion (FIG. 3C, absorbance versus collagen concentration µg/ml), colony formation (FIG. 3D, number of colonies).
Figure 3B:
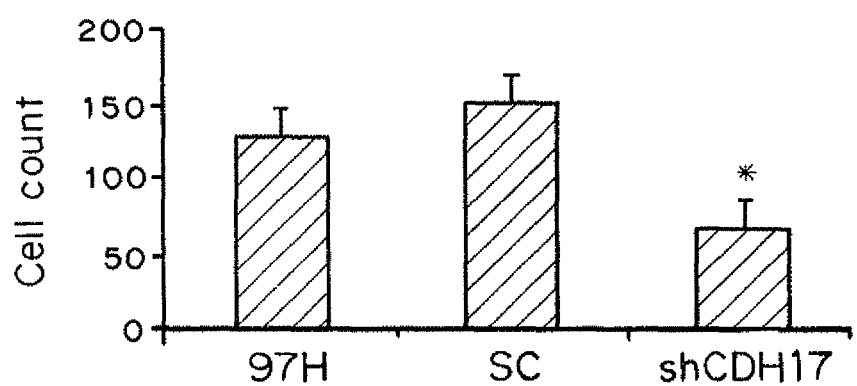
Figure 3C:
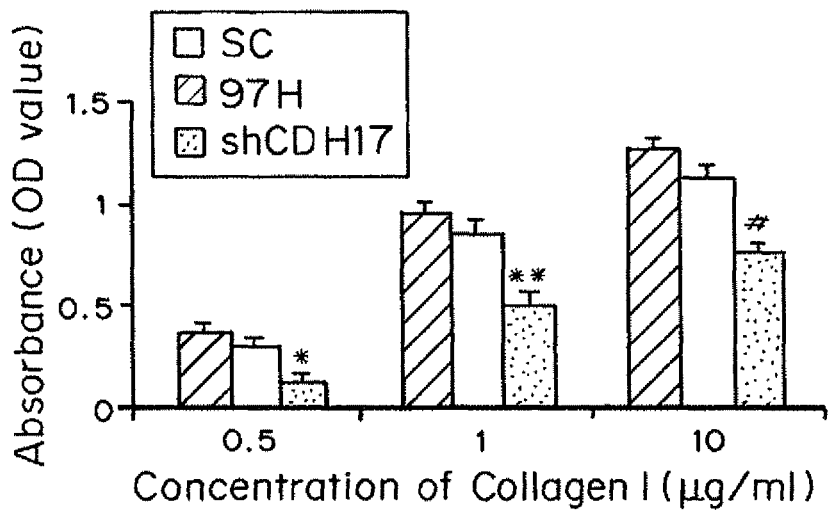
Figure 3D:
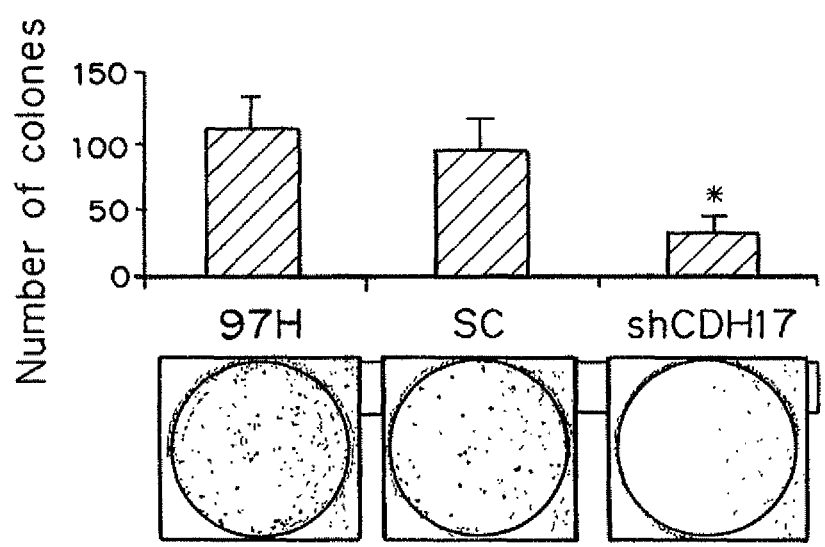

FIGS. 3A, 3B, 3C, and 3D, compare the effects of transfecting 97H cells with shRNA targeting the CDH17 exon 5 with the effects of 97H and scramble (SC) on CDH17 protein level (FIG. 3A, absorbance versus time, hours), cell proliferation (FIG. 3B, cell concentration), cell invasion (FIG. 3C, absorbance versus collagen concentration μg/ml), colony formation (FIG. 3D, number of colonies). Tumor cells with reduced expressions of CDH17 were rendered to be less "tumorigenic".

Example 5

Characterization of Two Monoclonal Antibodies Against CDH17 and the Use of these Antibodies for Establishing an ELISA for Detection of CDH17 in Human Serum Materials and Methods Two monoclonal antibodies (Lic3 and Lic5) against CDH17 were synthesized and selected using an established protocol in the laboratory. Isotypes of these antibodies were determined using IsoStrip Mouse Monoclonal Antibody Isotyping Kit (Roche). The isotypes of Lic3 and Lic5 are IgG2a and IgG2b, respectively.

The hybridoma having the American Type Culture Collection (ATCC®) accession number PTA-122082 and producing the Lic3 monoclonal antibody, as well as the hybridoma having the ATCC® accession number PTA-122081 and producing the Lic5 monoclonal antibody, were deposited on Mar. 27, 2015, at the ATCC®, 10801 University Boulevard, Manassas, Va. 20110, U.S.A.

Results

Based on the preliminary data, the truncated form of CDH17 spanning domains 1 and 2 of CDH17 (D1-D2) was detected in serum of HCC patients. It was postulated that detection of D1-D2 in human serum serves as a marker to indicate incidence of HCC. Recombinant D1-D2 (SEQ ID NO: 1), having a molecular weight of 85 kDa, was synthesized using established protocols and western blots were performed to examine the specificity of Lic3 and Lic5 in detecting this recombinant protein. Lic3 and Lic5 were found to detect synthesized D1-D2. The recombinant protein was synthesized with several tags, such as Nus tag, His tag, and S tag. The apparent molecular weight of this protein was ~147 kDa (on a polyacrylamide gel).

An ELISA was performed based on different concentration of D1-D2, Lic3, and Lic5. The results of the characterization of the two monoclonal antibodies against recombinant CDH17, representing the D1-D2 epitope, established the antibodies could be used in an ELISA for detection of CDH17 in human serum.

Example 6

Reduction in Tumor Size after Silencing Expression of CDH17 in MHCC97-H Cells by shRNA Targeting Exon 5

Materials and Methods shRNA construct targeting exon 5 of human CDH17 was designed. The shRNA forward (sh_e5F: 5'-GAT CCC GCC AGT CCC TAT CAC CAT AGA GAA GCT TGT CTA TGG TGA TAG GGA CTG GTT TTT T-3') (SEQ ID NO: 3) and reverse (sh_e5R: 5'-CTA GAA AAA ACC AGT CCC TAT CAC CAT AGA CAA GCT TCT CTA TGG TGA TAG GGA CTG GCG G-3') (SEQ ID NO: 4) inserts for cloning into shRNA expression vectors were designed as described on the Sigma-Aldrich website. These two inserts were linked by a loop sequence described in the GeneEraser™. shRNA Mammalian Expression Vector Kit (Stratagene, La Jolla, Calif.). This construct was transfected into liver cancer cells (MHCC97-H cells) using lipofectamine (Invitrogen, Carlsbad, Calif.) to suppress the expression of CDH17. Stable transfectants were selected using G418 sulfate (Calbiochem, San Diego, Calif.) at a concentration of 1 mg/ml. A scramble experiment was also included to assess the specificity of the transfection experiment.

Results

Figure 4:
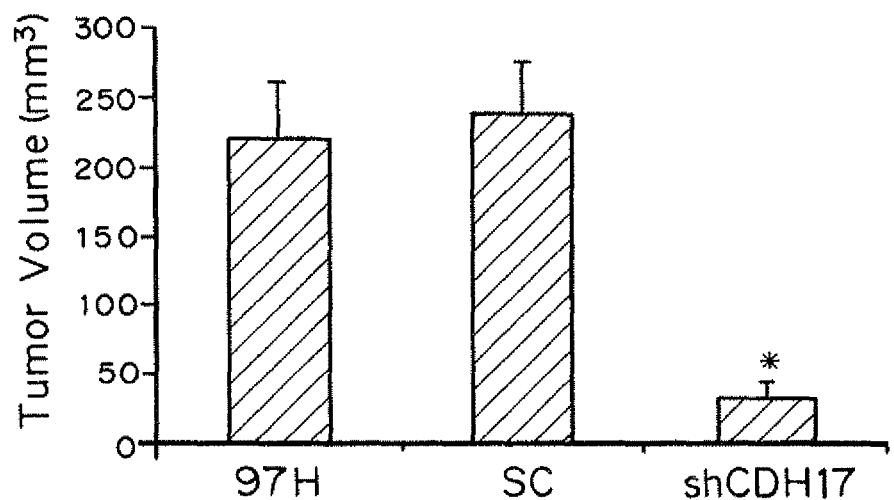
FIG. 4 is a bar graph showing reduction of tumor volume ($mm^3$) when knockdown shCDH17 cells (MHCC97-H) were transplanted into nude mice for developing tumor xenografts, controls were 97H and SC.

The protein level of CDH17 was diminished in one of the selected transfectants (shCDH17) when assessed by western blot analysis. A significant reduction in cell proliferation, cell invasion, colony formation, and cell adhesion was observed in shCDH17 cells. In a tumor xenograft model, knockdown of CDH17 in MHCC97-H cells was performed as described above before these cells were transplanted subcutaneously in nude mice for developing tumor xenografts. A reduction in size and volume of the subcutaneous tumor were observed when shCDH17 cells were used to transplant into the nude mice (FIG. 4). [abbreviations: MHCC97-H, 97H; Scramble Control, SC]

Example 6

Figure 5:
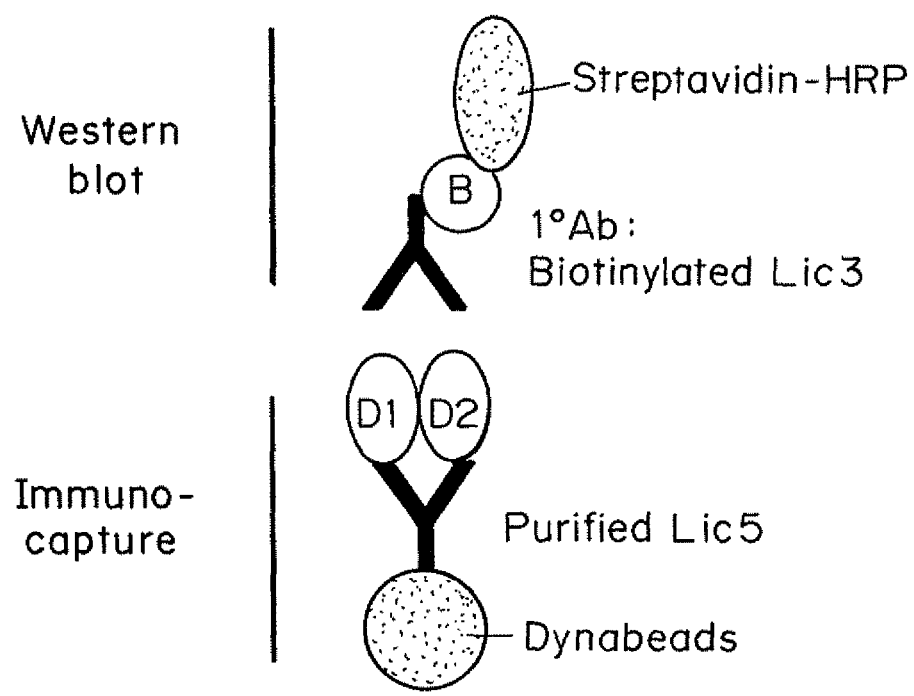
FIG. 5 is a schematic diagram illustrating the experimental immuno-capture of D1D2 by Dynabeads to immuno-capture recombinant D1D2. Two different Dynabeads were used (Dynabeads Protein G and Dynabeads M-280 Tosylactivated). For the immuno-capture using Dynabeads Protein G, different concentrations of D1D2 were incubated with purified Lic5 before mixing with the Dynabeads Protein G. For the immuno-capture using Dynabeads M-280 Tosylactivated, purified Lic5 was first coupled to the beads before mixing with different concentrations of D1D2. This was followed by Lic5-D1D2 immunocomplex being eluted from the beads using SDS sample buffer and subsequently subjected to western blot analysis. Western blot is used with biotinylated Lic3 to detect D1D2 and a horseradish peroxidase (HRP)-conjugated streptavidin is used to react with the biotinylated Lic3.

Methods of Extracting Recombinant D1-D2 of CDH17 (SEQ ID: 1) Using Immunomagnetic Bead Capture Assay As shown in FIG. 5, two ways to selectively extract the recombinant D1-D2 of CDH17 (D1-D2) using an immunomagnetic bead capture assay were used. Two different Dynabeads were used (Dynabeads Protein G and Dynabeads M-280 Tosylactivated). For the immuno-capture using Dynabeads Protein G, different concentrations of D1-D2 were incubated with purified Lic5 before mixing with the Dynabeads Protein G. For the immuno-capture using Dynabeads M-280 Tosylactivated, purified Lic5 was first coupled to the beads before mixing with different concentrations of D1-D2. This was followed by Lic5-D1-D2 immunocomplex being eluted from the beads using SDS sample buffer and subsequently subjected to western blot analysis. Western blot is used with biotinylated Lic3 to detect D1-D2 and a horseradish peroxidase (HRP)-conjugated streptavidin is used to react with the biotinylated Lic3.

For the first approach, purified anti-CDH17 Lic3 monoclonal antibody was coupled to Dynabeads M-250 Tosylactivated beads (Invitrogen), according to the manufacturer's protocol. The anti-CDH17-beads were then allowed to bind to D1-D2. After that, sample buffer was added to the beads to elute the Lic3-D1-D2 complex. After separation of the beads using a magnet, the supernatant was used to run a western blot or to determine the antigen by standard ELISA or mass spectrometry methods. A titration experiment was performed to optimize the concentration of coating purified Lic3 monoclonal antibody for conjugation to the magnet beads. For the second approach, purified Lic3 monoclonal antibody was allowed to bind to pre-washed Dynabeads Protein G (Invitrogen), followed by incubating the beads with D1-D2. After that, sample buffer was added to the beads to elute the Lic3-D1-D2 complex from the beads. After separation of the beads using a magnet, the supernatant was used to run a western blot. The abilities of using Dynabeads to extract D1-D2 by enzyme-linked immunosorbent assay (ELISA) were also analyzed and used to determine the amount of D1-D2.

We claim:

1. A monoclonal antibody specific for the secreted form of cadherin-17 (CDH17) wherein the antibody is the antibody Lic3 produced by the hybridoma having the ATCC accession number PTA-122082 or the antibody Lic5 produced by the hybridoma having the ATCC accession number PTA-122081.

2. A monoclonal antibody binding to the same epitope recognized by the antibody Lic3 produced by the hybridoma having the ATCC accession number PTA-122082 or the antibody Lic5 produced by the hybridoma having the ATCC accession number PTA-122081.

3. A kit comprising either or both of the antibodies of claim 1.

4. The antibody of claim 2 selected from the group consisting of monoclonal antibodies, recombinant antibodies, chimeric antibodies, single chain antibodies, and antigen-binding fragments thereof.

5. A kit comprising either or both of the antibodies of claim 2.

6. A method of diagnosing a liver cancer characterized by the overexpression and/or upregulation of cadherin-17 (CDH17) comprising the steps of: (i) determining the level of expression of CDH17 in a serum sample from a patient; (ii) comparing the levels of CDH17 expression to a normal serum sample; and (iii) increased level of CDH17 expression in the serum sample from the patient relative to the normal sample indicates that the patient has liver cancer associated with the overexpression and/or upregulation of CDH17, wherein the determination of the level of expression of CDH17 is made with the antibody Lic3 produced by the hybridoma having the ATCC accession number PTA-122082, the antibody Lic5 produced by the hybridoma having the ATCC accession number PTA-122081, or a combination thereof.

7. The method of claim 6, wherein the cancer is hepatocellular carcinoma.

8. The method of claim 6 wherein the serum sample from the patient is extracted from the patient.

* * * * *